US012790623B2

(12) United States Patent
Strings-Ufombah et al.

(10) Patent No.: US 12,790,623 B2
(45) Date of Patent: Nov. 10, 2026

(54) COMPOSITIONS AND METHODS FOR TREATING OCULOPHARYNGEAL MUSCULAR DYSTROPHY (OPMD)

(71) Applicant: Benitec IP Holdings Inc., Wilmington, DE (US)

(72) Inventors: Vanessa Strings-Ufombah, Wilmington, DE (US); David Suhy, Wilmington, DE (US); Shih-Chu Kao, Wilmington, DE (US); Petrus W. Roelvink, Wilmington, DE (US)

(73) Assignee: Benitec IP Holdings Inc., Wilmington, DE (US)

( * ) Notice: Subject to any disclaimer, the term of this patent is extended or adjusted under 35 U.S.C. 154(b) by 1302 days.

(21) Appl. No.: 17/434,666

(22) PCT Filed: Feb. 28, 2020

(86) PCT No.: PCT/AU2020/050182

§ 371 (c)(1),
(2) Date: Aug. 27, 2021

(87) PCT Pub. No.: WO2020/172720

PCT Pub. Date: Sep. 3, 2020

(65) Prior Publication Data

US 2022/0098614 A1 Mar. 31, 2022

Related U.S. Application Data

(60) Provisional application No. 62/812,187, filed on Feb. 28, 2019.

(51) Int. Cl.

| | |
|---|---|
| ***C12N 15/86*** | (2006.01) |
| ***A61K 48/00*** | (2006.01) |
| ***A61P 21/00*** | (2006.01) |
| ***C12N 15/113*** | (2010.01) |

(52) U.S. Cl.

CPC .......... *C12N 15/86* (2013.01); *A61K 48/0075* (2013.01); *A61P 21/00* (2018.01); *C12N 15/113* (2013.01)

(58) Field of Classification Search

None

See application file for complete search history.

(56) References Cited

FOREIGN PATENT DOCUMENTS

| | | | |
|---|---|---|---|
| WO | 2018/107228 | A1 | 6/2018 |
| WO | 2019/043630 | A1 | 3/2019 |
| WO | 2020172720 | A1 | 9/2020 |

OTHER PUBLICATIONS

BB-301: A Single "Silence and Replace" AAV-Based Vector for the Treatment of Oculopharyngeal Muscular Dystrophy (OPMD) The 21st Annual Meeting of the American Society of Gene and Cell Therapy (ASGCT), Chicago, retrieved on-line Apr. 17, 2025, benitec.com/our-programs/presentations-and-publications, 19 pages (Year: 2018).*

Towards Development of a 'Silence and Replace' Based Approach for the Treatment of Oculopharyngeal Muscular Dystrophy. Joint 10th AGCST and ASSCR Scientific Meeting, Sydney May 25, 2017, retrieved onlineApr. 17, 2025, 25 pages,benitec.com/our-programs/presentations-and-publications (Year: 2017).*

Malerba et al. Nature Communications, 8, 14848, Supplementary Information pp. 1-11 (Year: 2017).*

International Search Report for PCT/AU2020/050182, mailed on Apr. 28, 2020, 5 pages.

Written Opinion of the International Searching Authority for PCT/AU2020/050182, mailed on Apr. 28, 2020, 8 pages.

Malerba, A., et al., "PABPNI gene therapy for oculopharyngeal muscular dystrophy", Nature Communications. 2017, vol. 8, article No. 14848 Abstract; p. 2, right col., para 3, lines 1-15; Fig 1.

Abu-Baker, A.,. et al., 'RNA-Based Therapy Utilizing Oculopharyngeal Muscular Dystrophy Transcript Knockdown and Replacement', Molecular Therapy Nucleic Acids. Apr. 15, 2019, vol. 15, pp. 12-25.

Urabe, M. et al., Scalable generation of high-titer recombinant adeno-associated virus type 5 in insect cells, Journal of virology. 2006, vol. 80, No. 4 pp. 1874-1885.

* cited by examiner

*Primary Examiner* — Brian Whiteman

(74) *Attorney, Agent, or Firm* — Goodwin Procter LLP

(57) ABSTRACT

The present disclosure relates to modified adeno-associated virus (AAV) delivery vectors comprising 'silence and replace' DNA constructs, compositions comprising same, and the use of the modified AAV and compositions to treat oculopharyngeal muscular dystrophy (OPMD) in individuals suffering from OPMD or which are predisposed thereto. In particular, the disclosure relates to AAV having a capsid protein with a modified subunit 1 (VP1) and comprising a 'silence and replace' DNA construct, wherein the 'silence and replace' DNA construct comprises (i) a DNA-directed RNAi (ddRNAi) construct encoding short hairpin microRNA (shmiR) targeting PABPN1 causative of OPMD and (ii) a PABPN1 construct encoding functional PABPN1 protein having a mRNA transcript which is not targeted by the shmiRs at (i). The present disclosure also relates to the methods of treating OPMD comprising direct injection of an AAV of the disclosure to a subject's pharyngeal muscles.

26 Claims, 23 Drawing Sheets

Specification includes a Sequence Listing.

COMPOSITIONS AND METHODS FOR TREATING OCULOPHARYNGEAL MUSCULAR DYSTROPHY (OPMD)

CROSS-REFERENCE TO RELATED APPLICATIONS

This application is a national phase 371 application which claim priority to PCT/AU2020/050182, filed on Feb. 28, 2020, which claims the right of priority to U.S. Provisional No. 62/812,187, filed 28 Feb. 2019, the complete contents of which is incorporated by reference herein in its entirety.

SEQUENCE LISTING

Reference to a Sequence Listing Submitted Electronically via EFS-Web

This application includes a Sequence Listing submitted electronically via EFS-Web (name: FBB-032WOUS_SL.txt; size: 55,600 bytes; and created on: Aug. 27, 2021), which is hereby incorporated by reference in its entirety.

TECHNICAL FIELD

The present disclosure relates to modified adeno-associated virus (AAV) delivery vectors comprising 'silence and replace' DNA constructs, compositions comprising same, and the use of the modified AAV and compositions to treat oculopharyngeal muscular dystrophy (OPMD) in individuals suffering from OPMD or which are predisposed thereto.

BACKGROUND

OPMD is an autosomal dominant inherited, slow progressing, late-onset degenerative muscle disorder. The disease is mainly characterised by progressive eyelid drooping (ptosis) and swallowing difficulties (dysphagia). The pharyngeal and cricopharyngeal muscles are specific targets in OPMD. Proximal limb weakness tends to follow at a later stage of disease progression. The mutation that causes the disease is an abnormal expansion of a (GCN)n trinucleotide repeat in the coding region of the poly(A) binding protein nuclear 1 (PABPN1) gene. This expansion leads to an expanded polyalanine tract at the N-terminal of the PABPN1 protein: 10 alanines are present in the normal protein, expanded to 11 to 18 alanines in the mutant form (expPABPN1). The main pathological hallmark of the disease is nuclear aggregates of expPABPN1. A misfolding of expanded PABPN1 results in the accumulation of insoluble polymeric fibrillar aggregates inside nuclei of affected cells. PABPN1 is an aggregation prone protein and mutant alanine-expanded PABPN1 in OPMD has a higher aggregation rate than that of the wild type normal protein. However, it is still unclear whether the nuclear aggregates in OPMD have a pathological function or a protective role as a consequence of a cellular defence mechanism.

No approved treatment, pharmacological or otherwise, is presently available for OPMD. Symptomatic surgical interventions can partly correct ptosis and improve swallowing in moderate to severely affected individuals. For example, the cricopharyngeal myotomy is at present the only possible treatment available to improve swallowing in these patients. However, this does not correct the progressive degradation of the pharyngeal musculature, which often leads to death following swallowing difficulties and choking.

Accordingly, there remains a need for therapeutic agents to treat OPMD in patients suffering therefrom and/or who are predisposed thereto.

SUMMARY

The present disclosure is based, in part, on the recognition by the inventors that no approved therapeutic agents currently exist for the treatment of OPMD. The present disclosure therefore provides a therapeutic agent for treatment of OPMD which is based on a modified adeno-associated virus (AAV) delivery vector comprising a 'silence and replace' construct comprising (i) one or more RNAi agents targeting regions of the PABPN1 mRNA transcript which is causative of OPMD, and (ii) a PABPN1 replacement construct for expression of wild-type (functional) human PABPN1 protein having a mRNA transcript which is not targeted by the RNAi agents of the disclosure. The present disclosure also provides methods of treating OPMD using the AAV delivery vectors and compositions comprising same.

According to one example, the present disclosure provides an adeno-associated virus (AAV) comprising:

(a) a viral capsid protein from AAV9 comprising a modified subunit 1 (VP1) sequence wherein the amino acids at positions 1, 26, 40, 43, and 44 are modified relative to a corresponding wildtype AAV9 VP1 sequence set forth in SEQ ID NO: 87; and (b) a polynucleotide sequence comprising (i) a DNA-directed RNAi (ddRNAi) construct comprising a nucleic acid comprising a sequence which encodes a short hairpin micro-RNA (shmiR); and (ii) a PABPN1 construct comprising a nucleic acid comprising a sequence encoding a functional PABPN1 protein having a mRNA transcript which is not targeted by the shmiR(s) encoded by the ddRNAi construct.

In one example, the modified AAV9 VP1 sequence comprises a serine at position 1, a glutamic acid at position 26, an arginine at position 40, an aspartic acid at position 43, and a serine at position 44 relative to the AAV9 VP1 sequence set forth in SEQ ID NO: 87. For example, the modified AAV9 VP1 sequence may comprise the following modifications A1S, A26E, Q40R, K43D, and A44S relative to the sequence set forth in SEQ ID NO: 87. In one example, the modified AAV9 VP1 sequence comprises the sequence set forth in SEQ ID NO: 88.

In one example, the viral capsid protein comprises mutations A42S, A67E, Q81R, K84D and A85S with respect to the full length wild-type AAV serotype 9 capsid sequence set forth in SEQ ID NO: 89. In one example, the viral capsid protein comprises the amino acid sequence set forth in SEQ ID NO: 90.

The present disclosure also provides an AAV comprising:

(a) a viral capsid protein from AAV8 comprising a modified subunit 1 (VP1) sequence wherein the amino acids at positions 1, 26, 40, 43, 44 and 64 are modified relative to a corresponding wildtype AAV8 VP1 sequence set forth in SEQ ID NO: 91; and (b) a polynucleotide sequence comprising (i) a ddRNAi construct comprising a nucleic acid comprising a sequence which encodes a shmiR; and (ii) a PABPN1 construct comprising a nucleic acid comprising a sequence encoding a functional PABPN1 protein having a mRNA transcript which is not targeted by the shmiR(s) encoded by the ddRNAi construct.

In one example, the modified AAV8 VP1 sequence comprises a serine at position 1, a glutamic acid at position 26, an arginine at position 40, an aspartic acid at position 43, a serine at position 44 and a lysine at position 64 relative to the AAV8 VP1 sequence set forth in SEQ ID NO: 91. For example, the modified AAV8 VP1 sequence may comprise the following modifications A1S, A26E, Q40R, K43D, A44S and Q64K relative to the sequence set forth in SEQ ID NO: 91. In one example, the modified AAV8 VP1 sequence comprises the sequence set forth in SEQ ID NO: 92.

In one example, the viral capsid protein comprises mutations A42S, A67E, Q81R, K84D, A85S and Q105K with respect to the full length wild-type AAV serotype 8 capsid sequence set forth in SEQ ID NO: 93. In one example, the viral capsid protein comprises the amino acid sequence set forth in SEQ ID NO: 94.

In each of the foregoing examples, the modified viral capsid protein is a delivery vector for the polynucleotide comprising the ddRNAi construct and the PABPN1 construct. In one example, the polynucleotide sequence comprises, in a 5' to 3' direction, the ddRNAi construct and the PABPN1 construct. In another example, the polynucleotide sequence comprises, in a 5' to 3' direction, the PABPN1 construct and the ddRNAi construct.

The polynucleotide may further comprises inverted terminal repeats (ITRs) from an AAV serotype. For example, the ITRs may flank the sequence comprising the ddRNAi construct and PABPN1 construct. In some examples, the ITRs are from an AAV2 serotype (e.g., SEQ ID NO: 95 and/or SEQ ID NO: 96).

In one example, the sequence encoding the functional PABPN1 protein is codon optimised such that its mRNA transcript is not targeted by the shmiRs of the ddRNAi construct. For example, the sequence encoding the functional PABPN1 protein may be the sequence set forth in SEQ ID NO: 73.

In one example, the ddRNAi construct and the sequence encoding the functional PABPN1 protein are operably-linked to a promoter positioned upstream of the ddRNAi construct and the sequence encoding the functional PABPN1 protein. In some examples, the promoter is a muscle-specific promoter.

In one example, the or each shmiR encoded by the ddRNAi construct comprises:

an effector sequence of at least 17 nucleotides in length;
an effector complement sequence;
a stemloop sequence; and
a primary micro RNA (pri-miRNA) backbone;

wherein the effector sequence is substantially complementary to a region of corresponding length in an RNA transcript set forth in any one of SEQ ID NOs: 1-13.

In one example, at least one shmiR encoded by the ddRNAi construct is selected from the group consisting of:

a shmiR comprising an effector sequence set forth in SEQ ID NO: 15 and an effector complement sequence set forth in SEQ ID NO: 14;
a shmiR comprising an effector sequence set forth in SEQ ID NO: 17 and an effector complement sequence set forth in SEQ ID NO: 16;
a shmiR comprising an effector sequence set forth in SEQ ID NO: 19 and an effector complement sequence set forth in SEQ ID NO: 18;
a shmiR comprising an effector sequence set forth in SEQ ID NO: 21 and an effector complement sequence set forth in SEQ ID NO: 20;
a shmiR comprising an effector sequence set forth in SEQ ID NO: 23 and an effector complement sequence set forth in SEQ ID NO: 22;
a shmiR comprising an effector sequence set forth in SEQ ID NO: 25 and an effector complement sequence set forth in SEQ ID NO: 24;
a shmiR comprising an effector sequence set forth in SEQ ID NO: 27 and an effector complement sequence set forth in SEQ ID NO: 26;
a shmiR comprising an effector sequence set forth in SEQ ID NO: 29 and an effector complement sequence set forth in SEQ ID NO: 28;
a shmiR comprising an effector sequence set forth in SEQ ID NO: 31 and an effector complement sequence set forth in SEQ ID NO: 30;
a shmiR comprising an effector sequence set forth in SEQ ID NO: 33 and an effector complement sequence set forth in SEQ ID NO: 32;
a shmiR comprising an effector sequence set forth in SEQ ID NO: 35 and an effector complement sequence set forth in SEQ ID NO: 34;
a shmiR comprising an effector sequence set forth in SEQ ID NO: 37 and an effector complement sequence set forth in SEQ ID NO: 36; and
a shmiR comprising an effector sequence set forth in SEQ ID NO: 39 and an effector complement sequence set forth in SEQ ID NO: 38.

In one particular example, the ddRNAi construct encodes a shmiR comprising an effector sequence set forth in SEQ ID NO: 31 and an effector complement sequence set forth in SEQ ID NO: 30; and a shmiR comprising an effector sequence set forth in SEQ ID NO: 39 and an effector complement sequence set forth in SEQ ID NO: 38. For example, the ddRNAi construct may encode a shmiR designated shmiR13 as described herein and a shmiR designated shmiR17 as described herein.

In one example, the or each shmiR comprises, in a 5' to 3' direction:

a 5' flanking sequence of the pri-miRNA backbone;
the effector complement sequence;
the stemloop sequence;
the effector sequence; and
a 3' flanking sequence of the pri-miRNA backbone.

In another example, the or each shmiR comprises, in a 5' to 3' direction:

a 5' flanking sequence of the pri-miRNA backbone;
the effector sequence;
the stemloop sequence;
the effector complement sequence; and
a 3' flanking sequence of the pri-miRNA backbone.

In one example, the stemloop sequence is the sequence set forth in SEQ ID NO: 40.

In one example, the pri-miRNA backbone is a pri-miR-30a backbone. For example, the 5' flanking sequence of the pri-miRNA backbone may be the sequence set forth in SEQ ID NO: 41 and the 3' flanking sequence of the pri-miRNA backbone may be the sequence set forth in SEQ ID NO: 42.

In one example, the ddRNAi construct comprises at least two nucleic acids each encoding a shmiR, wherein each shmiR comprises an effector sequence which is substantially complementary to a RNA transcript corresponding to a PABPN1 protein which is causative of OPMD, and wherein each shmiR comprises a different effector sequence.

In one example, each of the at least two nucleic acids within the ddRNAi construct may encode a shmiR comprising an effector sequence which is substantially complementary to a region of corresponding length in an RNA transcript set forth in one of SEQ ID NOs: 1, 2, 4, 7, 9, 10 and 13. For example, the at least two nucleic acids within the ddRNAi construct are selected from the group consisting of:

- a nucleic acid comprising or consisting of a DNA sequence encoding a shmiR comprising an effector sequence set forth in SEQ ID NO: 15 and an effector complement sequence set forth in SEQ ID NO: 14 (shmiR2);
- a nucleic acid comprising or consisting of a DNA sequence encoding a shmiR comprising an effector sequence set forth in SEQ ID NO: 17 and an effector complement sequence set forth in SEQ ID NO: 16 (shmiR3);
- a nucleic acid comprising or consisting of a DNA sequence encoding a shmiR comprising an effector sequence set forth in SEQ ID NO: 21 and an effector complement sequence set forth in SEQ ID NO: 20 (shmiR5);
- a nucleic acid comprising or consisting of a DNA sequence encoding a shmiR comprising an effector sequence set forth in SEQ ID NO: 27 and an effector complement sequence set forth in SEQ ID NO: 26 (shmiR9);
- a nucleic acid comprising or consisting of a DNA sequence encoding a shmiR comprising an effector sequence set forth in SEQ ID NO: 31 and an effector complement sequence set forth in SEQ ID NO: 30 (shmiR13);
- a nucleic acid comprising or consisting of a DNA sequence encoding a shmiR comprising an effector sequence set forth in SEQ ID NO: 33 and an effector complement sequence set forth in SEQ ID NO: 32 (shmiR14); and
- a nucleic acid comprising or consisting of a DNA sequence encoding a shmiR comprising an effector sequence set forth in SEQ ID NO: 39 and an effector complement sequence set forth in SEQ ID NO: 38 (shmiR17).

For example, the at least two nucleic acids within the ddRNAi construct may be selected from the group consisting of: a nucleic acid comprising or consisting of a DNA sequence set forth in SEQ ID NO: 56 (shmiR2); a nucleic acid comprising or consisting of a DNA sequence set forth in SEQ ID NO: 57 (shmiR3); a nucleic acid comprising or consisting of a DNA sequence set forth in SEQ ID NO: 59 (shmiR5); a nucleic acid comprising or consisting of a DNA sequence set forth in SEQ ID NO: 62 (shmiR9); a nucleic acid comprising or consisting of a DNA sequence set forth in SEQ ID NO: 64 (shmiR13); a nucleic acid comprising or consisting of a DNA sequence set forth in SEQ ID NO: 65 (shmiR14); and a nucleic acid comprising or consisting of a DNA sequence set forth in SEQ ID NO: 68 (shmiR17).

In one example, each of the at least two nucleic acids within the ddRNAi construct encode a shmiR comprising an effector sequence which is substantially complementary to a region of corresponding length in an RNA transcript set forth in one of SEQ ID NOs: 2, 9, 10 and 13. For example, the at least two nucleic acids within the ddRNAi construct may be selected from the group consisting of:

- a nucleic acid comprising or consisting of a DNA sequence encoding a shmiR comprising an effector sequence set forth in SEQ ID NO: 17 and an effector complement sequence set forth in SEQ ID NO: 16 (shmiR3);
- a nucleic acid comprising or consisting of a DNA sequence encoding a shmiR comprising an effector sequence set forth in SEQ ID NO: 31 and an effector complement sequence set forth in SEQ ID NO: 30 (shmiR13);
- a nucleic acid comprising or consisting of a DNA sequence encoding a shmiR comprising an effector sequence set forth in SEQ ID NO: 33 and an effector complement sequence set forth in SEQ ID NO: 32 (shmiR14); and
- a nucleic acid comprising or consisting of a DNA sequence encoding a shmiR comprising an effector sequence set forth in SEQ ID NO: 39 and an effector complement sequence set forth in SEQ ID NO: 38 (shmiR17).

For example, the at least two nucleic acids within the ddRNAi construct may be selected from the group consisting of: a nucleic acid comprising or consisting of a DNA sequence set forth in SEQ ID NO: 57 (shmiR3); a nucleic acid comprising or consisting of a DNA sequence set forth in SEQ ID NO: 64 (shmiR13); a nucleic acid comprising or consisting of a DNA sequence set forth in SEQ ID NO: 65 (shmiR14); and a nucleic acid comprising or consisting of a DNA sequence set forth in SEQ ID NO: 68 (shmiR17).

In one particular example, the at least two nucleic acids are selected from a nucleic acid comprising or consisting of a DNA sequence encoding a shmiR comprising an effector sequence set forth in SEQ ID NO: 31 and an effector complement sequence set forth in SEQ ID NO: 30 (shmiR13); and a nucleic acid comprising or consisting of a DNA sequence encoding a shmiR comprising an effector sequence set forth in SEQ ID NO: 39 and an effector complement sequence set forth in SEQ ID NO: 38 (shmiR17). For example, the at least two nucleic acids may be a nucleic acid comprising or consisting of a DNA sequence set forth in SEQ ID NO: 64 (shmiR13); and a nucleic acid comprising or consisting of a DNA sequence set forth in SEQ ID NO: 68 (shmiR17).

In any one of the foregoing examples, the ddRNAi construct and the PABPN1 construct may be operably linked to a promoter. In one example, the ddRNAi construct and the PABPN1 construct are operably linked to the same promoter e.g., a muscle-specific promoter. Also provided are compositions comprising the AAV of the disclosure and one or more pharmaceutically acceptable carriers.

The present disclosure also provides a plurality of baculovirus vectors for producing AAVs of the disclosure in insect cells. In one example, the plurality of baculovirus vectors comprise:

(a) a first baculovirus vector comprising a nucleic acid molecule encoding an AAV viral capsid protein with the modified VP1 sequence as described herein; and (b) a second baculovirus vector comprising a polynucleotide encoding the ddRNAi construct and PABPN1 construct as described herein, flanked by AAV inverted terminal repeat (ITR) sequences.

In one example, the first baculovirus vector comprises a nucleic acid molecule encoding a viral capsid protein from AAV9 comprising a modified VP1 sequence wherein the amino acids at positions 1, 26, 40, 43, and 44 are modified relative to a corresponding wildtype AAV9 VP1 sequence set forth in SEQ ID NO: 87, and the second baculovirus vector comprises a polynucleotide sequence comprising (i) a ddRNAi construct encoding a shmiR and (ii) a PABPN1 construct encoding a functional PABPN1 protein having a mRNA transcript which is not targeted by the shmiR(s) encoded by the ddRNAi construct.

In one example, the modified AAV9 VP1 sequence comprises a serine at position 1, a glutamic acid at position 26, an arginine at position 40, an aspartic acid at position 43, and a serine at position 44 relative to the AAV9 VP1 sequence set forth in SEQ ID NO: 87. For example, the modified AAV9 VP1 sequence may comprise the following modifications A1S, A26E, Q40R, K43D, and A44S relative to the sequence set forth in SEQ ID NO: 87. In one example, the modified AAV9 VP1 sequence comprises the sequence set forth in SEQ ID NO: 88.

In one example, the viral capsid protein comprises mutations A42S, A67E, Q81R, K84D and A85S with respect to the full length wild-type AAV serotype 9 capsid sequence set forth in SEQ ID NO: 89. In one example, the viral capsid protein comprises the amino acid sequence set forth in SEQ ID NO: 90.

In another example, the first baculovirus vector comprises a nucleic acid molecule encoding a viral capsid protein from AAV8 comprising a modified VP1 sequence wherein the amino acids at positions 1, 26, 40, 43, 44 and 64 are modified relative to a corresponding wildtype AAV8 VP1 sequence set forth in SEQ ID NO: 91, and the second baculovirus vector comprises a polynucleotide sequence comprising (i) a ddRNAi construct encoding a shmiR and (ii) a PABPN1 construct encoding a functional PABPN1 protein having a mRNA transcript which is not targeted by the shmiR(s) encoded by the ddRNAi construct.

In one example, the modified AAV8 VP1 sequence comprises a serine at position 1, a glutamic acid at position 26, an arginine at position 40, an aspartic acid at position 43, a serine at position 44 and a lysine at position 64 relative to the AAV8 VP1 sequence set forth in SEQ ID NO: 91. For example, the modified AAV8 VP1 sequence may comprise the following modifications A1S, A26E, Q40R, K43D, A44S and Q64K relative to the sequence set forth in SEQ ID NO: 91. In one example, the modified AAV8 VP1 sequence comprises the sequence set forth in SEQ ID NO: 92.

In one example, the viral capsid protein comprises mutations A42S, A67E, Q81R, K84D, A85S and Q105K with respect to the full length wild-type AAV serotype 8 capsid sequence set forth in SEQ ID NO: 93. In one example, the viral capsid protein comprises the amino acid sequence set forth in SEQ ID NO: 94.

In each of the foregoing examples, the AAV ITR sequences may be from the same serotype as the viral capsid protein encoded by the nucleic acid molecule within the first baculovirus vector. In another example, the AAV ITR sequences are from another AAV serotype e.g., AAV2. In some examples, the ITR sequences are from AAV serotype 2 and comprise the sequences set forth in SEQ ID NO: 95 and/or SEQ ID NO: 96.

As described herein, the second baculovirus vector comprises a ddRNAi construct encoding one or more shmiRs targeting PABPN1. Exemplary ddRNAi constructs encoding shmiRs, including combinations of shmiRs, targeting PABPN1 are described herein. In one example, the second baculovirus vector may comprise comprises a ddRNAi construct encoding shmiR13 and shmiR17, and a polynucleotide construct comprising a sequence encoding the functional PABPN1 protein that is codon optimised such that its mRNA transcript is not targeted by the shmiRs of the ddRNAi construct (e.g., a sequence set forth in SEQ ID NO: 73). For example, the second baculovirus vector may comprise a ddRNAi construct comprising or consisting of a DNA sequence encoding a shmiR comprising an effector sequence set forth in SEQ ID NO: 31 and an effector complement sequence which is substantially complementary to the sequence set forth in SEQ ID NO: 31 e.g., an effector complement sequence set forth in SEQ ID NO: 30 (shmiR13), and a nucleic acid comprising or consisting of a DNA sequence encoding a shmiR comprising an effector sequence set forth in SEQ ID NO: 39 and an effector complement sequence which is substantially complementary to the sequence set forth in SEQ ID NO: 39 e.g., an effector complement sequence set forth in SEQ ID NO: 38 (shmiR17). For example, the second baculovirus vector may comprise a ddRNAi construct comprising a nucleic acid comprising or consisting of the DNA sequence set forth in SEQ ID NO: 64 (shmiR13), and a nucleic acid comprising or consisting of the DNA sequence set forth in SEQ ID NO: 68 (shmiR17).

In accordance with an example in which the first baculovirus vector does not encode AAV Rep proteins, the plurality of baculovirus vectors may further comprise:

(c) a third baculovirus vector comprising a polynucleotide sequence encoding at least one large AAV Rep protein selected from Rep78 and Rep68 and at least one small AAV Rep protein selected from Rep52 and Rep40.

At least one of the baculovirus vectors in the plurality may comprise a polynucleotide encoding the assembly-activating protein (AAP). In one example, the baculovirus vector encoding the capsid protein comprises a polynucleotide encoding an AAP. In alternative example, the baculovirus encoding the Rep proteins and/or the baculovirus encoding the ddRNAi construct and PABPN1 construct, comprises a polynucleotide encoding an AAP.

The present disclosure also provides a method for producing an AAV as described herein in an insect cell, said method comprising:

(i) culturing an insect cell comprising a plurality of baculovirus vectors as described herein in culture media under conditions sufficient for the cells to produce an AAV; and optionally (ii) recovering the AAV from the culture media and/or cells.

In one example, the method comprises co-infecting the insect cell with the baculovirus vectors.

In one example, the method of producing the AAV comprises recovering the AAV from the culture media and/or cells. In another example, the method of producing the AAV comprises recovering the AAV from the culture media and/or cells and then purifying the AAV. In one example, the AAV are recovered from the cells. In one example, the AAV are recovered from the culture media. In one example, the AAV are recovered from the cell and culture media.

The present disclosure also provides an AAV produced by the method described herein.

The present disclosure also provides methods for treating a subject suffering from oculopharyngeal muscular dystrophy (OPMD) comprising administering to said subject the AAV of the disclosure or a composition comprising same; wherein the AAV or composition is administered by direct injection to a pharyngeal muscle of the subject. In one example, the AAV of the disclosure or composition comprising same is administered by direct injection to a pharyngeal muscle of the subject. For example, the pharyngeal muscle comprises one or more of an inferior constrictor muscle, a middle constrictor muscle, a superior constrictor muscle, a palatopharyngeus muscle, a salpingopharyngeus muscle, a stylopharyngeus muscle, or any combination thereof. In one example, the AAV of the disclosure or composition comprising same is administered by direct injection to a muscle of the tongue in the subject.

KEY TO THE SEQUENCE LISTING

Figure 1:
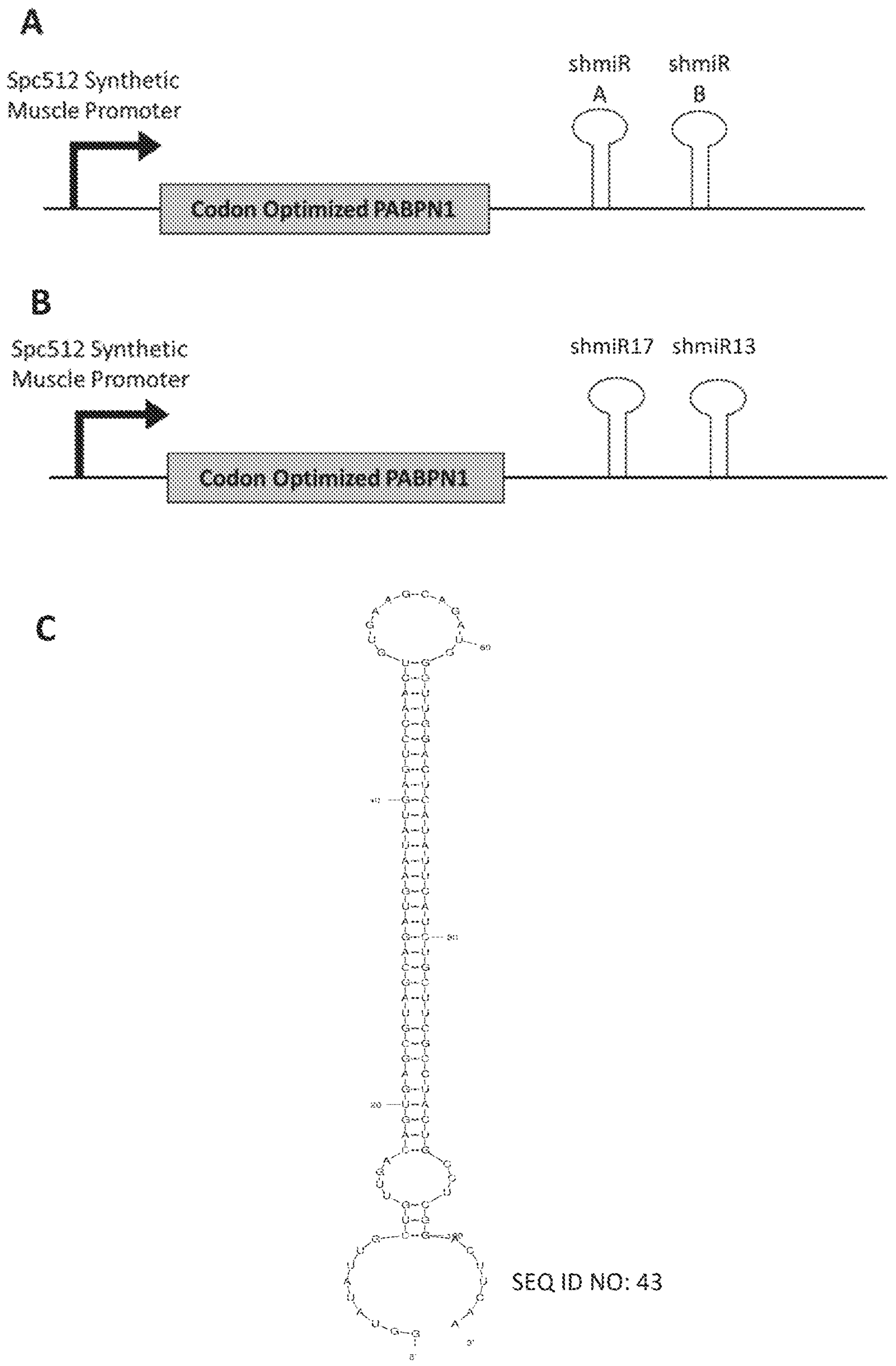
FIG. 1A is a schematic illustrating a construct for simultaneous gene silencing of endogenous PABPN1 and replacement with codon optimised PABPN1 generated by subcloning two shmiRs targeting wtPABPN1 into the 3' untranslated region of the codon optimized PABPN1 transcript in between the two pAAV2 ITRs (ITRs not shown in schematic).
FIG. 1B is a schematic illustrating the 'silence and replace' construct (SR-construct) designed for simultaneous gene silencing of endogenous PABPN1 and replacement with codon optimised PABPN1 generated by subcloning two shmiRs targeting wtPABPN1 (shmiR17 and shmiR13) into the 3' untranslated region of the codon optimized PABPN1 transcript in the pAAV2 vector backbone.
FIG. 1C illustrates the predicted secondary structure of a representative shmiR construct comprising a 5' flanking region, a siRNA sense strand; a stem/loop junction sequence, an siRNA anti-sense strand, and a 3' flanking region.

SEQ ID NO: 1: RNA sequence for region within mRNA transcript corresponding to PABPN1 protein designated PABPN1 mRNA Region 2.

SEQ ID NO: 2: RNA sequence for region within mRNA transcript corresponding to PABPN1 protein designated PABPN1 mRNA Region 3.

SEQ ID NO: 3: RNA sequence for region within mRNA transcript corresponding to PABPN1 protein designated PABPN1 mRNA Region 4.

SEQ ID NO: 4: RNA sequence for region within mRNA transcript corresponding to PABPN1 protein designated PABPN1 mRNA Region 5.

SEQ ID NO: 5: RNA sequence for region within mRNA transcript corresponding to PABPN1 protein designated PABPN1 mRNA Region 6.

SEQ ID NO: 6: RNA sequence for region within mRNA transcript corresponding to PABPN1 protein designated PABPN1 mRNA Region 7.

SEQ ID NO: 7: RNA sequence for region within mRNA transcript corresponding to PABPN1 protein designated PABPN1 mRNA Region 9.

SEQ ID NO: 8: RNA sequence for region within mRNA transcript corresponding to PABPN1 protein designated PABPN1 mRNA Region 11.

SEQ ID NO: 9: RNA sequence for region within mRNA transcript corresponding to PABPN1 protein designated PABPN1 mRNA Region 13.

SEQ ID NO: 10: RNA sequence for region within mRNA transcript corresponding to PABPN1 protein designated PABPN1 mRNA Region 14.

SEQ ID NO: 11: RNA sequence for region within mRNA transcript corresponding to PABPN1 protein designated PABPN1 mRNA Region 15.

SEQ ID NO: 12: RNA sequence for region within mRNA transcript corresponding to PABPN1 protein designated PABPN1 mRNA Region 16.

SEQ ID NO: 13: RNA sequence for region within mRNA transcript corresponding to PABPN1 protein designated PABPN1 mRNA Region 17.

SEQ ID NO: 14: RNA effector complement sequence for shmiR designated shmiR2.

SEQ ID NO: 15: RNA effector sequence for shmiR designated shmiR2.

SEQ ID NO: 16: RNA effector complement sequence for shmiR designated shmiR3.

SEQ ID NO: 17: RNA effector sequence for shmiR designated shmiR3.

SEQ ID NO: 18: RNA effector complement sequence for shmiR designated shmiR4.

SEQ ID NO: 19: RNA effector sequence for shmiR designated shmiR4.

SEQ ID NO: 20: RNA effector complement sequence for shmiR designated shmiR5.

SEQ ID NO: 21: RNA effector sequence for shmiR designated shmiR5.

SEQ ID NO: 22: RNA effector complement sequence for shmiR designated shmiR6.

SEQ ID NO: 23: RNA effector sequence for shmiR designated shmiR6.

SEQ ID NO: 24: RNA effector complement sequence for shmiR designated shmiR7.

SEQ ID NO: 25: RNA effector sequence for shmiR designated shmiR7.

SEQ ID NO: 26: RNA effector complement sequence for shmiR designated shmiR9.

SEQ ID NO: 27: RNA effector sequence for shmiR designated shmiR9.

SEQ ID NO: 28: RNA effector complement sequence for shmiR designated shmiR11.

SEQ ID NO: 29: RNA effector sequence for shmiR designated shmiR11.

SEQ ID NO: 30: RNA effector complement sequence for shmiR designated shmiR13.

SEQ ID NO: 31: RNA effector sequence for shmiR designated shmiR13.

SEQ ID NO: 32: RNA effector complement sequence for shmiR designated shmiR14.

SEQ ID NO: 33: RNA effector sequence for shmiR designated shmiR14.

SEQ ID NO: 34: RNA effector complement sequence for shmiR designated shmiR15.

SEQ ID NO: 35: RNA effector sequence for shmiR designated shmiR15.

SEQ ID NO: 36: RNA effector complement sequence for shmiR designated shmiR16.

SEQ ID NO: 37: RNA effector sequence for shmiR designated shmiR16.

SEQ ID NO: 38: RNA effector complement sequence for shmiR designated shmiR17.

SEQ ID NO: 39: RNA effector sequence for shmiR designated shmiR17.

SEQ ID NO: 40: RNA stem loop sequence for shmiRs

SEQ ID NO: 41: 5' flanking sequence of the pri-miRNA backbone.

SEQ ID NO: 42: 3' flanking sequence of the pri-miRNA backbone

SEQ ID NO: 43: RNA sequence for shmiR designated shmiR2.

SEQ ID NO: 44: RNA sequence for shmiR designated shmiR3.

SEQ ID NO: 45: RNA sequence for shmiR designated shmiR4.

SEQ ID NO: 46: RNA sequence for shmiR designated shmiR5.

SEQ ID NO: 47: RNA sequence for shmiR designated shmiR6.

SEQ ID NO: 48: RNA sequence for shmiR designated shmiR7.

SEQ ID NO: 49: RNA sequence for shmiR designated shmiR9.

SEQ ID NO: 50: RNA sequence for shmiR designated shmiR11.

SEQ ID NO: 51: RNA sequence for shmiR designated shmiR13.

SEQ ID NO: 52: RNA sequence for shmiR designated shmiR14.

SEQ ID NO: 53: RNA sequence for shmiR designated shmiR15.

SEQ ID NO: 54: RNA sequence for shmiR designated shmiR16.

SEQ ID NO: 55: RNA sequence for shmiR designated shmiR17.

SEQ ID NO: 56: DNA sequence coding for shmiR designated shmiR2.

SEQ ID NO: 57: DNA sequence coding for shmiR designated shmiR3.

SEQ ID NO: 58: DNA sequence coding for shmiR designated shmiR4.

SEQ ID NO: 59: DNA sequence coding for shmiR designated shmiR5.
SEQ ID NO: 60: DNA sequence coding for shmiR designated shmiR6.
SEQ ID NO: 61: DNA sequence coding for shmiR designated shmiR7.
SEQ ID NO: 62: DNA sequence coding for shmiR designated shmiR9.
SEQ ID NO: 63: DNA sequence coding for shmiR designated shmiR11.
SEQ ID NO: 64: DNA sequence coding for shmiR designated shmiR13.
SEQ ID NO: 65: DNA sequence coding for shmiR designated shmiR14.
SEQ ID NO: 66: DNA sequence coding for shmiR designated shmiR15.
SEQ ID NO: 67: DNA sequence coding for shmiR designated shmiR16.
SEQ ID NO: 68: DNA sequence coding for shmiR designated shmiR17.
SEQ ID NO: 69: DNA sequence for double construct version 1 coding for shmiR3 and shmiR14 under control of the muscle specific CK8 promoter and codon optimized PABPN1 under control of Spc512
SEQ ID NO: 70: DNA sequence for double construct version 1 coding for shmiR17 and shmiR13 under control of the muscle specific CK8 promoter and codon optimized PABPN1 under control of Spc512
SEQ ID NO: 71: DNA sequence for double construct version 2 coding for coPABPN1 and shmiRs designated shmiR3 and shmiR14, under control of Spc512.
SEQ ID NO: 72: DNA sequence for double construct version 2 coding for coPABPN1 and shmiRs designated shmiR17 and shmiR13 under control of Spc512.
SEQ ID NO: 73 DNA sequence for Human codon-optimized PABPN1 cDNA sequence.
SEQ ID NO: 74 Amino acid sequence for codon-optimised human PABPN1 protein.
SEQ ID NO: 75 Amino acid sequence for wildtype human PABPN1 protein with FLAG-tag.
SEQ ID NO: 76 Amino acid sequence for codon-optimised human PABPN1 protein with FLAG-tag.
SEQ ID NO: 77 DNA sequence for primer designated wtPABPN1-Fwd.
SEQ ID NO: 78 DNA sequence for primer designated wtPABPN1-Rev
SEQ ID NO: 79 DNA sequence for probe designated wtPABPN1-Probe
SEQ ID NO: 80 DNA sequence for primer designated optPABPN1-Fwd
SEQ ID NO: 81 DNA sequence for primer designated optPABPN1-Rev
SEQ ID NO: 82 DNA sequence for probe designated optPABPN1-Probe
SEQ ID NO: 83 DNA sequence for primer designated shmiR3-FWD
SEQ ID NO: 84 DNA sequence for primer designated shmiR13-FWD
SEQ ID NO: 85 DNA sequence for primer designated shmiR14-FWD
SEQ ID NO: 86 DNA sequence for primer designated shmiR17-FWD
SEQ ID NO: 87 Wildtype VP1 subsequence for AAV serotype 9, comprising the PLA2 domain and flanking sequence.
SEQ ID NO: 88 Modified VP1 subsequence for AAV serotype 9, comprising the PLA2 domain and flanking sequence.
SEQ ID NO: 89 Full-length wild-type AAV serotype 9 capsid.
SEQ ID NO: 90 Full-length modified AAV serotype 9 capsid.
SEQ ID NO: 91 Wildtype VP1 subsequence for AAV serotype 8, comprising the PLA2 domain and flanking sequence.
SEQ ID NO: 92 Modified VP1 subsequence for AAV serotype 8, comprising the PLA2 domain and flanking sequence.
SEQ ID NO: 93 Full-length wild-type AAV serotype 8 capsid.
SEQ ID NO: 94 Full-length modified AAV serotype 8 capsid.
SEQ ID NO: 95 AAV2 5' ITR Sequence.
SEQ ID NO: 96 AAV2 3' ITR Sequence.
SEQ ID NO: 97 Full-length wild-type AAV serotype 2 capsid.
SEQ ID NO: 98 RNA sequence encoding wildtype human PABPN1 protein.

DETAILED DESCRIPTION

General

Throughout this specification, unless specifically stated otherwise or the context requires otherwise, reference to a single step, feature, composition of matter, group of steps or group of features or compositions of matter shall be taken to encompass one and a plurality (i.e. one or more) of those steps, features, compositions of matter, groups of steps or groups of features or compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant DNA, recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbor Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbor Laboratory, (1988), and J. E. Coligan et al. (editors) Current Protocols in Immunology, John Wiley & Sons (including all updates until present).

Throughout this specification, unless the context requires otherwise, the word "comprise", or variations such as "comprises" or "comprising", is understood to imply the inclusion of a stated step or element or integer or group of steps or elements or integers but not the exclusion of any other step or element or integer or group of elements or integers.

The term "and/or", e.g., "X and/or Y" shall be understood to mean either "X and Y" or "X or Y" and shall be taken to provide explicit support for both meanings or for either meaning.

Selected Definitions

By "RNA" is meant a molecule comprising at least one ribonucleotide residue. By "ribonucleotide" is meant a nucleotide with a hydroxyl group at the 2' position of a β-D-ribo-furanose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siRNA or internally, for example at one or more nucleotides of the RNA. Nucleotides in the RNA molecules of the instant disclosure can also comprise non-standard nucleotides, such as non-naturally occurring nucleotides or chemically synthesized nucleotides or deoxynucleotides. These altered RNAs can be referred to as analogs or analogs of naturally-occurring RNA.

The term "RNA interference" or "RNAi" refers generally to RNA-dependent silencing of gene expression initiated by double stranded RNA (dsRNA) molecules in a cell's cytoplasm. The dsRNA molecule reduces or inhibits transcription products of a target nucleic acid sequence, thereby silencing the gene or reducing expression of that gene.

As used herein, the term "double stranded RNA" or "dsRNA" refers to a RNA molecule having a duplex structure and comprising an effector sequence and an effector complement sequence which are of similar length to one another. The effector sequence and the effector complement sequence can be in a single RNA strand or in separate RNA strands. The "effector sequence" (often referred to as a "guide strand") is substantially complementary to a target sequence, which in the present case, is a region of a PABPN1 mRNA transcript. The "effector sequence" can also be referred to as the "antisense sequence". The "effector complement sequence" will be of sufficient complementary to the effector sequence such that it can anneal to the effector sequence to form a duplex. In this regard, the effector complement sequence will be substantially homologous to a region of target sequence. As will be apparent to the skilled person, the term "effector complement sequence" can also be referred to as the "complement of the effector sequence" or the sense sequence.

As used herein, the term "duplex" refers to regions in two complementary or substantially complementary nucleic acids (e.g., RNAs), or in two complementary or substantially complementary regions of a single-stranded nucleic acid (e.g., RNA), that form base pairs with one another, either by Watson-Crick base pairing or any other manner that allows for a stabilized duplex between the nucleotide sequences that are complementary or substantially complementary. It will be understood by the skilled person that within a duplex region, 100% complementarity is not required; substantial complementarity is allowable. Substantial complementarity includes may include 79% or greater complementarity. For example, a single mismatch in a duplex region consisting of 19 base pairs (i.e., 18 base pairs and one mismatch) results in 94.7% complementarity, rendering the duplex region substantially complementary. In another example, two mismatches in a duplex region consisting of 19 base pairs (i.e., 17 base pairs and two mismatches) results in 89.5% complementarity, rendering the duplex region substantially complementary. In yet another example, three mismatches in a duplex region consisting of 19 base pairs (i.e., 16 base pairs and three mismatches) results in 84.2% complementarity, rendering the duplex region substantially complementary, and so on.

The dsRNA may be provided as a hairpin or stem loop structure, with a duplex region comprised of an effector sequence and effector complement sequence linked by at least 2 nucleotide sequence which is termed a stem loop. When a dsRNA is provided as a hairpin or stem loop structure it can be referred to as a "hairpin RNA" or "short hairpin RNAi agent" or "shRNA". Other dsRNA molecules provided in, or which give rise to, a hairpin or stem loop structure include primary miRNA transcripts (pri-miRNA) and precursor microRNA (pre-miRNA). Pre-miRNA shRNAs can be naturally produced from pri-miRNA by the action of the enzymes Drosha and Pasha which recognize and release regions of the primary miRNA transcript which form a stem-loop structure. Alternatively, the pri-miRNA transcript can be engineered to replace the natural stem-loop structure with an artificial/recombinant stem-loop structure. That is, an artificial/recombinant stem-loop structure may be inserted or cloned into a pri-miRNA backbone sequence which lacks its natural stem-loop structure. In the case of stemloop sequences engineered to be expressed as part of a pri-miRNA molecule, Drosha and Pasha recognize and release the artificial shRNA. dsRNA molecules produced using this approach are known as "shmiRNAs", "shmiRs" or "microRNA framework shRNAs".

As used herein, the term "complementary" with regard to a sequence refers to a complement of the sequence by Watson-Crick base pairing, whereby guanine (G) pairs with cytosine (C), and adenine (A) pairs with either uracil (U) or thymine (T). A sequence may be complementary to the entire length of another sequence, or it may be complementary to a specified portion or length of another sequence. One of skill in the art will recognize that U may be present in RNA, and that T may be present in DNA. Therefore, an A within either of a RNA or DNA sequence may pair with a U in a RNA sequence or T in a DNA sequence. A person of skill in the art will also recognise that a G present in RNA may pair with C or U in RNA.

As used herein, the term "substantially complementary" is used to indicate a sufficient degree of complementarity or precise pairing such that stable and specific binding occurs between nucleic acid sequences e.g., between the effector sequence and the effector complement sequence or between the effector sequence and the target sequence. It is understood that the sequence of a nucleic acid need not be 100% complementary to that of its target or complement. The term encompasses a sequence complementary to another sequence with the exception of an overhang. In some cases, the sequence is complementary to the other sequence with the exception of 1-2 mismatches. In some cases, the sequences are complementary except for 1 mismatch. In some cases, the sequences are complementary except for 2 mismatches. In other cases, the sequences are complementary except for 3 mismatches. In yet other cases, the sequences are complementary except for 4 mismatches.

The term "encoded", as used in the context of a shRNA or shmiR of the disclosure, shall be understood to mean a shRNA or shmiR which is capable of being transcribed from a DNA template. Accordingly, a nucleic acid that encodes, or codes for, a shRNA or shmiR of the disclosure will comprise a DNA sequence which serves as a template for transcription of the respective shRNA or shmiR.

The term "DNA-directed RNAi construct" or "ddRNAi construct" refers to a nucleic acid comprising DNA sequence which, when transcribed produces a shRNA or shmiR molecule (preferably a shmiR) which elicits RNAi. The ddRNAi construct may comprise a nucleic acid which is transcribed as a single RNA that is capable of self-annealing into a hairpin structure with a duplex region linked by a stem loop of at least 2 nucleotides i.e., shRNA or shmiR, or as a single RNA with multiple shRNAs or shmiRs, or as multiple RNA transcripts each capable of folding as a single shRNA or shmiR respectively. The ddRNAi construct may be provided within a larger "DNA construct" comprising one or more additional DNA sequences. For example, the ddRNAi construct may be provided in a DNA construct comprising a further DNA sequence coding for functional PABPN1 protein which has been codon optimised such that its mRNA transcript is not targeted by shmiRs of the ddRNAi construct. The ddRNAi construct and/or the DNA construct comprising same may be within an expression vector e.g., operably linked to a promoter.

As used herein, the term "operably-linked" or "operable linkage" (or similar) means that a coding nucleic acid sequence is linked to, or in association with, a regulatory sequence, e.g., a promoter, in a manner which facilitates expression of the coding sequence. Regulatory sequences include promoters, enhancers, and other expression control elements that are art-recognized and are selected to direct expression of the coding sequence.

As used herein, the term "inverted terminal repeat" or "ITR", in the plural or singular, refers to sequence located at one end of a vector that can form a hairpin structure when used in combination with a complementary sequence that is located at the opposing end of the vector. The pair of inverted terminal repeats is involved in rescue of AAV DNA, replication and packaging in the host genome. The ITRs are also used for efficient encapsidation of the AAV DNA and generation of fully assembled AAV particles.

A "vector" will be understood to mean a vehicle for introducing a nucleic acid into a cell. Vectors include, but are not limited to, plasmids, phagemids, viruses, bacteria, and vehicles derived from viral or bacterial sources. A "plasmid" is a circular, double-stranded DNA molecule. A useful type of vector for use in accordance with the present disclosure is a viral vector, wherein heterologous DNA sequences are inserted into a viral genome that can be modified to delete one or more viral genes or parts thereof. Certain vectors are capable of autonomous replication in a host cell (e.g., vectors having an origin of replication that functions in the host cell). Other vectors can be stably integrated into the genome of a host cell, and are thereby replicated along with the host genome. As used herein, the term "expression vector" will be understood to mean a vector capable of expressing a RNA molecule of the disclosure.

A "functional PABPN1 protein" shall be understood to mean a PABPN1 protein having the functional properties of a wild-type PABPN1 protein e.g., an ability to control site of mRNA polyadenylation and/or intron splicing in a mammalian cell. Accordingly, a "functional PABPN1 protein" will be understood to be a PABPN1 protein which is not causative of OPMD when expressed or present in a subject. In one example, a reference herein to "functional PABPN1 protein" is a reference to human wild-type PABPN1 protein. The sequence of human wild-type PABPN1 protein is set forth in NCBI RefSeq NP_004634. Accordingly, a functional human PABPN1 protein may have the functional properties in vivo of the human PABPN1 protein set forth in NCBI RefSeq NP_004634.

As used herein, the terms "treating", "treat" or "treatment" and variations thereof, refer to clinical intervention designed to alter the natural course of the individual or cell being treated during the course of clinical pathology. Desirable effects of treatment include decreasing the rate of disease progression, ameliorating or palliating the disease state, and remission or improved prognosis. It follows that treatment of OPMD includes reducing or inhibiting expression of a PABPN1 protein which is causative of OPMD in the subject and/or expressing in the subject a PABPN1 protein having the normal length of polyalanine residues. Preferably, treatment of OPMD includes reducing or inhibiting expression of the PABPN1 protein which is causative of OPMD in the subject and expressing in the subject a PABPN1 protein having the normal length of polyalanine residues. An individual is successfully "treated", for example, if one or more of the above treatment outcomes is achieved.

A "therapeutically effective amount" is at least the minimum concentration or amount required to effect a measurable improvement in the OPMD condition, such as a measurable improvement in in one or more symptoms of OPMD e.g., including but not limited to ptosis, dysphagia and muscle weakness in the subject. A therapeutically effective amount herein may vary according to factors such as the disease state, age, sex, and weight of the patient, and the ability of the shmiR, nucleic acid encoding same, ddRNAi construct, DNA construct, expression vector, or composition comprising same, to elicit a desired response in the individual and/or the ability of the expression vector to express functional PABPN1 protein in the subject. A therapeutically effective amount is also one in which any toxic or detrimental effects of the shmiR, nucleic acid encoding same, ddRNAi construct, DNA construct, expression vector, or composition comprising same, are outweighed by the therapeutically beneficial effects of the shmiR, nucleic acid encoding same, ddRNAi construct, DNA construct, expression vector, or composition comprising same, to inhibit, suppress or reduce expression of PABPN1 protein causative of OPMD considered alone or in combination with the therapeutically beneficial effects of the expression of functional PABPN1 protein in the subject.

As used herein, the "subject" or "patient" can be a human or non-human animal suffering from or genetically predisposed to OPMD i.e., possess a PABPN1 gene variant which is causative of OPMD. The "non-human animal" may be a primate, livestock (e.g. sheep, horses, cattle, pigs, donkeys), companion animal (e.g. pets such as dogs and cats), laboratory test animal (e.g. mice, rabbits, rats, guinea pigs, *drosophila, C. elegans*, zebrafish), performance animal (e.g. racehorses, camels, greyhounds) or captive wild animal. In one example, the subject or patient is a mammal. In one example, the subject or patient is a human.

The terms "reduced expression", "reduction in expression" or similar, refer to the absence or an observable decrease in the level of protein and/or mRNA product from the target gene e.g., the PABPN1 gene. The decrease does not have to be absolute, but may be a partial decrease sufficient for there to a detectable or observable change as a result of the RNAi effected by the shmiR, nucleic acid encoding same, ddRNAi construct, DNA construct, expression vector, or composition comprising same of the disclosure. The decrease can be measured by determining a decrease in the level of mRNA and/or protein product from a target nucleic acid relative to a cell lacking the shmiR, nucleic acid encoding same, ddRNAi construct, DNA construct, expression vector, or composition comprising same, and may be as little as 1%, 5% or 10%, or may be absolute i.e., 100% inhibition. The effects of the decrease may be determined by examination of the outward properties i.e., quantitative and/or qualitative phenotype of the cell or organism, and may also include detection of the presence or a change in the amount of nuclear aggregates of expPABPN1 in the cell or organism following administration of a shmiR, nucleic acid encoding same, ddRNAi construct, DNA construct, expression vector, or composition comprising same, of the disclosure.

A "delivery system" as used herein refers to a vector for packaging foreign genetic material, such as DNA or RNA, and which can be introduced into a cell. Delivery systems can include viral vectors, e.g., an adeno-associated viral (AAV) vector, a retroviral vector, an adenoviral vector (AdV) and a lentiviral (LV) vector. As described herein, viral vectors can be used to deliver and express foreign genetic material in cell. Accordingly, a viral expression vector as described herein may be used as a delivery system.

As used herein, the term "Adeno-Associated Virus" or "AAV" relates to a group of viruses within the Parvoviridae family which contain a short (approx. 4.7 kb) single-stranded DNA genome and which depend on the presence of a helper virus, such as an Adenovirus for their replication. Also contemplated by the present disclosure are vectors derived from AAV, e.g., used as gene transfer vehicles.

As used herein, the term "serotype", as used in the context of AAV, is a distinction used to refer to an AAV having a capsid that is serologically distinct from other AAV serotypes. Serologic distinctiveness is determined on the basis of the lack of cross-reactivity between antibodies to one AAV as compared to another AAV. Such cross-reactivity differences are usually due to differences in capsid protein sequences/antigenic determinants (e.g., due to VP1, VP2, and/or VP3 sequence differences of AAV serotypes).

As used herein in the context of an AAV, the term "viral capsid protein", "capsid protein", "capsid polypeptide" or similar relates to a polypeptide of the AAV having the activity of self-assembly to produce the proteinaceous shell of an AAV particle, also referred to as coat protein or VP protein. It is comprised of three subunits, VP1, VP2 and VP3, which are typically expressed from a single nucleic acid molecule, and which interact together to form a capsid of an icosahedral symmetry. The capsid structure of AAV is described in BERNARD N FIELDS et al., VIROLOGY, volume 2, chapters 69 & 70 (4th ed., Lippincott-Raven Publishers).

As used herein, the term "promoter" refers generally to a DNA sequence that is involved in recognition and binding of DNA-dependent RNA polymerase and other proteins (trans-acting transcription factors) to initiate and control transcription of one or more coding sequences, and is generally located upstream of the coding sequence with respect to the direction of transcription.

The term "improved functionality" or similar as used in the context of AAV of the disclosure comprising modified capsid protein or VP1 sequences, shall be understood to mean that the AAV comprising the modified capsid protein or VP1 sequence has an improved endosomal escape activity relative to a wildtype AAV of the same serotype which has not been modified and which is produced in insect cells. As used herein, the term "endosomal escape activity", endosome escape activity", or similar, shall be understood to mean the ability of an AAV to escape from the endosomal compartment following cellular internalisation. In the context of AAV functionality, it will be appreciated that an AAV which is unable to escape from the endosome following cellular internalisation is not functional, particularly in the context of gene therapy.

A "pharyngeal muscle" as used herein refers to one or more of the group of muscles that form the pharynx. The pharyngeal muscle can include one or more of the inferior constrictor muscle, middle constrictor muscle, superior constrictor muscle, palatopharyngeus muscle, the salpingopharyngeus muscle, and/or the stylopharyngeus muscle.

Modified AAV Delivery Vectors for Treatment of OPMD

Adeno-associated virus (AAV) is a dependent parvovirus that generally requires co-infection with another virus (typically an adenovirus or herpesvirus) to initiate and sustain a productive infectious cycle. In the absence of such a helper virus, AAV is still competent to infect or transduce a target cell by receptor-mediated binding and internalization, penetrating the nucleus in both non-dividing and dividing cells. Because progeny virus is not produced from AAV infection in the absence of helper virus, the extent of transduction is restricted only to the initial cells that are infected with the virus. It is this feature which makes AAV a desirable vector for use in gene therapies. Furthermore, unlike retrovirus, adenovirus, and herpes simplex virus, AAV appears to lack human pathogenicity and toxicity (Kay, et al., *Nature.* 424: 251 (2003)). Since the genome normally encodes only two genes it is not surprising that, as a delivery vehicle, AAV is limited by a packaging capacity of 4.5 kilobases (kb). However, although this size restriction may limit the genes that can be delivered for replacement gene therapies, it does not adversely affect the packaging and expression of shorter sequences such as shmiRs and shRNAs. For these reasons, the present disclosure contemplates the use of AAV as the vector or system for delivery of a PABPN1 'silence and replace' construct for treatment of OPMD. Generally, AAV used in gene therapy applications are preferably selected from those serotypes which are capable of infecting humans e.g., an AAV selected from the group consisting of AAV serotype 1, 2, 3, 4, 5, 6, 7, 8, 9, 10, 11, 12 and 13 (or variants thereof).

In one example, the present disclosure provides an AAV comprising:

(a) a viral capsid protein comprising a modified VP1 sequence, wherein specific amino acids within the phospholipase A2 (PLA2) domain and flanking sequence of the subunit 1 (VP1) are modified relative to the corresponding wildtype sequence to be more "AAV2-like"; and (b) a polynucleotide sequence comprising (i) a DNA-directed RNAi (ddRNAi) construct comprising a nucleic acid comprising a sequence which encodes a short hairpin micro-RNA (shmiR); and (ii) a PABPN1 construct comprising a nucleic acid comprising a sequence encoding a functional PABPN1 protein having a mRNA transcript which is not targeted by the shmiR(s) encoded by the ddRNAi construct.

In this regard, the inventors have shown that the endosomal escape activity of representative AAVs from serotypes other than serotype 2, produced from a baculovirus expression system in insect cells, can be restored or improved by making amino acid substitutions at specific sites within the PLA2 domain and its flanking sequence. For example, the inventors have shown that it is possible to restore or improve the endosomal escape activity of AAVs from representative serotypes other than serotype 2 by substituting amino acids at up to six different positions within the PLA2 domain and flanking sequence, with the amino acids at the corresponding positions within the AAV serotype 2 PLA2 domain and flanking sequence. In this regard, the inventors have shown that it is not necessary to swap the entire PLA2 domain and flanking sequence with that of AAV2 to produce chimeric AAVs, nor is it necessary to produce AAVs expressing mosaic capsids comprising the wildtype VP1/PLA2 sequence and that of AAV2 e.g., AAV2/WT VP1, as has been the strategy employed to date to improve functionality of AAVs produced in insect cells.

AAV sequences that can be used in the production of AAV with modified VP1 sequences as described herein can be derived from the genome of any AAV serotype. Generally, AAV serotypes have genomic sequences of significant homology at the amino acid and the nucleic acid levels, provide an identical set of genetic functions, produce virions which are physically and functionally similar, and replicate and assemble by practically identical mechanisms (with the specific exemption of the activity of the PLA2 domain described herein). Suitable nucleic acid and protein sequences for AAV for use in the design and production of the modified AAVs of the present disclosure are publically available. VP1 sequences for wildtype AAVs known to infect humans (and which are contemplated herein) are described in Chen et al., (2013) J. Vir. 87(11):6391-6405. Human or simian adeno-associated virus (AAV) serotypes are preferred sources of AAV nucleotide sequences for use in the context of the present disclosure, and more preferably AAV serotypes which normally infects humans (e.g., serotypes 1, 2, 3, 4, 5, 6, 7, 8, 9, 10, 11, 12 and 13). Capsid polypeptide sequences for AAV serotypes 1-13 are known in the art, for example, AAV1 (Genbank Acc. No: AAD27757.1, GI:4689097), AAV2 (Genbank Acc. No: AAC03780.1, GP.2906023), AAV3 (Genbank Acc. No: AAC55049.1, GI: 1408469), AAV4 (Genbank Acc. No: AAC58045.1, GL2337940), AAV5 (Genbank Acc. No: AAD13756.1, GI-4249658), AAV10 (Genbank Acc. No: AAT46337.1, GL48728343), AAV11 (Genbank Acc. No: AAT46339.1, GI:48728346), AAV12 (Genbank Acc. No: ABI16639.1, GI: 112379656), or AAV13 (Genbank Acc. No: ABZ10812.1, GI: 167047087). The polypeptide sequences for AAV capsid proteins for serotypes 1-13 are also set forth in SEQ ID NO: 27-39 herein. Furthermore, the complete genomes for AAV from serotypes 1-13 are known in the art, for example, AAV1 (NCBI Reference Sequence NC_002077.1), AAV2 (GenBank Acc. No: J01901.1), AAV3 (Genbank Acc. No: AF028705.1), AAV4 (NCBI Reference Sequence: NC_001829.1), AAV5 (NCBI Reference Sequence: NC_006152.1), AAV6 (GenBank: AF028704.1), AAV7 (NCBI Reference Sequence: NC_006260.1), AAV8 (NCBI Reference Sequence: NC_006261.1), AAV9 (GenBank Acc. No: AY530579.1), AAV10 (Genbank Acc. No: AY631965.1), AAV11 (Genbank Acc. No: AY631966.1) or AAV12 (Genbank Acc. No: DQ813647.1). In particular examples, the present disclosure provides AAV delivery vectors from serotypes 8 and 9.

In one example, the AAV of the present disclosure comprises a viral capsid protein from AAV9 comprising a modified VP1 sequence, wherein the amino acids at one or more of positions 1, 26, 40, 43, and 44 are modified relative to a corresponding wildtype AAV9 VP1 sequence set forth in SEQ ID NO: 87. For example, the AAV of the disclosure may comprise a viral capsid protein from AAV9 comprising a modified VP1 sequence comprising one or more of a serine at position 1, a glutamic acid at position 26, an arginine at position 40, an aspartic acid at position 43, a serine at position 44, and/or a lysine at position 64, wherein the amino acid positions are defined relative to the wildtype AAV9 VP1 sequence set forth in SEQ ID NO: 87, wherein the amino acids at any one or more of positions 1, 26, 40, 43 and 44 are modified relative to a corresponding wildtype AAV9 VP1 sequence. In some examples, no additional amino acids other than those at said any one or more positions 1, 26, 40, 43 and 44 are modified relative to the corresponding wildtype AAV9 VP1 sequence.

In one example, the AAV described herein may comprise a viral capsid protein from AAV9 with a modified VP1 sequence, wherein the amino acids at any two, three, four or five of positions 1, 26, 40, 43 and 44 are modified relative to a corresponding wildtype AAV9 VP1 sequence set forth in SEQ ID NO: 87.

In one example, the AAV described herein may comprise a viral capsid protein from AAV9 with a modified VP1 sequence, wherein the amino acids at any two or more of positions 1, 26, 40, 43 and 44 are modified relative to the corresponding wildtype AAV9 VP1 sequence set forth in SEQ ID NO: 87. For example, the modified VP1 sequence may comprise two or more modifications selected from A1S, A26E, Q40R, K43D, and A44S relative to the sequence set forth in SEQ ID NO: 87.

In one example, the AAV described herein may comprise a viral capsid protein from AAV9 with a modified VP1 sequence, wherein the amino acids at any three or more of positions 1, 26, 40, 43 and 44 are modified relative to a corresponding wildtype AAV9 VP1 sequence set forth in SEQ ID NO: 87. For example, the modified VP1 sequence may comprise three or more modifications selected from A1S, A26E, Q40R, K43D, and A44S relative to the sequence set forth in SEQ ID NO: 87.

In one example, the AAV described herein may comprise a viral capsid protein from AAV9 with a modified VP1 sequence, wherein the amino acids at any four or more of positions 1, 26, 40, 43 and 44 are modified relative to a corresponding wildtype AAV9 VP1 sequence set forth in SEQ ID NO: 87. For example, the modified VP1 sequence may comprise four or more modifications selected from A1S, A26E, Q40R, K43D, and A44S relative to the sequence set forth in SEQ ID NO: 87.

In one example, the AAV described herein may comprise a viral capsid protein from AAV9 with a modified VP1 sequence, wherein the amino acids at positions 1, 26, 40, 43 and 44 are modified relative to a corresponding wildtype AAV9 VP1 sequence set forth in SEQ ID NO: 87. For example, the modified VP1 sequence may comprise the following modifications A1S, A26E, Q40R, K43D, and A44S relative to the sequence set forth in SEQ ID NO: 87.

For example, the modified AAV9 VP1 sequence may comprise the amino acid sequence set forth in SEQ ID NO: 88. For example, the residues at positions 42, 67, 81, 84, and 85 are modified relative to a corresponding full-length wildtype AAV9 capsid VP1 sequence set forth in SEQ ID NO: 89 (e.g., modifications A42S, A67E, Q81R, K84D and A85S relative to the sequence set forth in SEQ ID NO: 89). In accordance with this example, the AAV of the disclosure may comprise a viral capsid protein from AAV9 comprising a modified VP1 sequence set forth in SEQ ID NO: 90.

In one example, the AAV of the present disclosure comprises a viral capsid protein from AAV8 comprising a modified VP1 sequence, wherein the amino acids at one or more of positions 1, 26, 40, 43, 44 and 64 are modified relative to a corresponding wildtype AAV8 VP1 sequence set forth in SEQ ID NO: 91. For example, the AAV of the disclosure may comprise a viral capsid protein from AAV8 comprising a modified VP1 sequence comprising one or more of a serine at position 1, a glutamic acid at position 26, an arginine at position 40, an aspartic acid at position 43, a serine at position 44, and/or a lysine at position 64, wherein the amino acid positions are defined relative to the wildtype AAV8 VP1 sequence set forth in SEQ ID NO: 91, wherein the amino acids at any one or more of positions 1, 26, 40, 43, 44 and 64 are modified relative to a corresponding wildtype AAV8 VP1 sequence. In some examples, no additional amino acids other than those at said any one or more positions 1, 26, 40, 43, 44 and 64 are modified relative to the corresponding wildtype AAV8 VP1 sequence.

In one example, the AAV described herein may comprise a viral capsid protein from AAV8 with a modified VP1 sequence, wherein the amino acids at any two, three, four or five of positions 1, 26, 40, 43, 44 and 64 are modified relative to a corresponding wildtype AAV8 VP1 sequence set forth in SEQ ID NO: 91.

In one example, the AAV described herein may comprise a viral capsid protein from AAV8 with a modified VP1 sequence, wherein the amino acids at any two or more of positions 1, 26, 40, 43, 44 and 64 are modified relative to the corresponding wildtype AAV8 VP1 sequence set forth in SEQ ID NO: 91. For example, the modified VP1 sequence may comprise two or more modifications selected from A1S, A26E, Q40R, K43D, A44S and Q64K relative to the sequence set forth in SEQ ID NO: 91.

In one example, the AAV described herein may comprise a viral capsid protein from AAV8 with a modified VP1 sequence, wherein the amino acids at any three or more of positions 1, 26, 40, 43, 44 and 64 are modified relative to a corresponding wildtype AAV8 VP1 sequence set forth in SEQ ID NO: 91. For example, the modified VP1 sequence may comprise three or more modifications selected from A1S, A26E, Q40R, K43D, A44S and Q64K relative to the sequence set forth in SEQ ID NO: 91.

In one example, the AAV described herein may comprise a viral capsid protein from AAV8 with a modified VP1 sequence, wherein the amino acids at any four or more of positions 1, 26, 40, 43, 44 and 64 are modified relative to a corresponding wildtype AAV8 VP1 sequence set forth in SEQ ID NO: 91. For example, the modified VP1 sequence may comprise four or more modifications selected from A1S, A26E, Q40R, K43D, A44S and Q64K relative to the sequence set forth in SEQ ID NO: 91.

In one example, the AAV described herein may comprise a viral capsid protein from AAV8 with a modified VP1 sequence, wherein the amino acids at any five or more of positions 1, 26, 40, 43, 44 and 64 are modified relative to a corresponding wildtype AAV8 VP1 sequence set forth in SEQ ID NO: 91. For example, the modified VP1 sequence may comprise five or more modifications selected from A1S, A26E, Q40R, K43D, A44S and Q64K relative to the sequence set forth in SEQ ID NO: 91.

In one example, the AAV described herein may comprise a viral capsid protein from AAV8 with a modified VP1 sequence, wherein the amino acids at positions 1, 26, 40, 43, 44 and 64 are modified relative to a corresponding wildtype AAV8 VP1 sequence set forth in SEQ ID NO: 91. For example, the modified VP1 sequence may comprise the following modifications A1S, A26E, Q40R, K43D, A44S and Q64K relative to the sequence set forth in SEQ ID NO: 91. For example, the modified AAV8 VP1 sequence may comprise the amino acid sequence set forth in SEQ ID NO: 92. For example, the residues at positions 42, 67, 81, 84, 85 and 105 are modified relative to a corresponding full-length wildtype AAV8 capsid VP1 sequence set forth in SEQ ID NO: 93 (e.g., modifications A42S, A67E, Q81R, K84D, A85S and Q105K relative to the sequence set forth in SEQ ID NO: 93). In accordance with this example, the AAV of the disclosure may comprise a viral capsid protein from AAV8 comprising a modified VP1 sequence set forth in SEQ ID NO: 94.

In each of the foregoing examples, the viral capsid protein may comprise subunit 2 (VP2) and subunit 3 (VP3) sequences from the same AAV serotype as the modified VP1. Preferably the VP1, VP1 and VP3 are expressed from the same ORF.

The AAV genome comprises replication (Rep) genes which are the proteins encoded by the virus which function in the replication of the viral genome. Accordingly, in one example, the AAV described herein comprises at least one large AAV Rep protein selected from Rep78 and Rep68 and at least one small AAV Rep protein selected from Rep52 and Rep40. In one example, the AAV described herein comprises Rep78 and Rep52. In one example, the AAV described herein comprises Rep78 and Rep40. In one example, the AAV described herein comprises Rep68 and Rep52. In one example, the AAV described herein comprises Rep68 and Rep40. In one example, In one example, the AAV described herein comprises Rep78, Rep68, Rep52 and Rep40. In each of the foregoing examples, the respective small and large Rep proteins can be from the same AAV serotype as the viral capsid protein. Alternatively, the respective small and large Rep proteins can be from an AAV serotype other than that of the viral capsid protein e.g., the Rep proteins can be from AAV2.

As described herein, AAV may be used as a delivery system in gene therapy. For example, AAVs may comprise a polynucleotide encoding a protein or RNA of interest. As describe herein, the AAV of the present disclosure comprises a polynucleotide sequence comprising a ddRNAi construct and a PABPN1 construct. The polynucleotide encoding the ddRNAi construct and a PABPN1 construct may be flanked by AAV inverted terminal repeat (ITR) sequences. In one example, the AAV ITR sequences are from the same serotype as the viral capsid protein. In another example, the AAV ITR sequences are from a serotype other than that of the viral capsid protein. In one particular example, the ITR sequences are from AAV serotype 2. In another particular example, the ITR sequences are from AAV serotype 2 and comprise the sequences set forth in SEQ ID NO: 91 and/or SEQ ID NO: 92.

As described hereinabove, the polynucleotide encoding the protein or RNA of interest, inclusive of the flanking ITRs, is typically 5,000 nucleotides (nt) or less in length. However, polynucleotide encoding oversized DNA, i.e.

more than 5,000 nt in length, are also contemplated. An oversized DNA is herein understood as a DNA exceeding the maximum AAV packaging limit of 5 kbp. Thus an AAV of the disclosure can be capable of expressing proteins or RNAs that are usually encoded by larger genomes than 5.0 kb can also be feasible.

As described herein, the AAV of the disclosure also comprises a polynucleotide sequence comprising a ddRNAi construct and a PABPN1 construct for expression in a mammalian cell, which is incorporated into its genome. Exemplary ddRNAi constructs and PABPN1 constructs are described herein (e.g., under the subheading “ddRNAi constructs”) and shall be shall be taken to apply mutatis mutandis to examples describing AAVs of the disclosure unless specifically stated otherwise. In this regard, the AAV of the disclosure may comprise a polynucleotide comprising a ddRNAi construct encoding any one or more of the shmiRs designated shmiR2-shmiR7, shmiR9, shmiR11, or shmiR13-shmiR17 as described herein. However, in particular examples, the AAV of the disclosure may comprise a polynucleotide comprising a ddRNAi construct encoding shmiR13 and/or shmiR17, and a polynucleotide construct comprising a sequence encoding the functional PABPN1 protein that is codon optimised such that its mRNA transcript is not targeted by the shmiRs of the ddRNAi construct (e.g., a sequence set forth in SEQ ID NO: 73). Exemplary ddRNAi constructs encoding shmiR13 and shmiR17 are described and contemplated herein.

In one particular example, the AAV comprises: (a) a viral capsid protein from AAV9 comprising a modified VP1 sequence having the modifications A1S, A26E, Q40R, K43D, and A44S relative to the corresponding wildtype sequence set forth in SEQ ID NO: 87 (e.g., a modified VP1 sequence comprising the sequence set forth in SEQ ID NO: 88); and (b) a polynucleotide sequence comprising (i) a ddRNAi construct comprising a nucleic acid comprising a sequence which encodes shmiR13 as described herein and shmiR17 as described herein; and (ii) a PABPN1 construct comprising a nucleic acid comprising a sequence encoding a functional PABPN1 protein having a mRNA transcript which is not targeted by the shmiR(s) encoded by the ddRNAi construct (e.g., a codon-optimised sequence set forth in SEQ ID NO: 73). The polynucleotide at (b) may be flanked by AAV inverted terminal repeat (ITR) sequences from AAV2 set forth in SEQ ID NO: 95 and SEQ ID NO: 96. In some embodiments, the ddRNAi construct comprises a nucleic acid comprising or consisting of a DNA sequence encoding a shmiR comprising an effector sequence set forth in SEQ ID NO: 31 and an effector complement sequence which is substantially complementary to the sequence set forth in SEQ ID NO: 31 e.g., an effector complement sequence set forth in SEQ ID NO: 30 (shmiR13), and a nucleic acid comprising or consisting of a DNA sequence encoding a shmiR comprising an effector sequence set forth in SEQ ID NO: 39 and an effector complement sequence which is substantially complementary to the sequence set forth in SEQ ID NO: 39 e.g., an effector complement sequence set forth in SEQ ID NO: 38 (shmiR17). For example, the ddRNAi construct in accordance with this example can comprise a nucleic acid comprising or consisting of the DNA sequence set forth in SEQ ID NO: 64 (shmiR13), and a nucleic acid comprising or consisting of the DNA sequence set forth in SEQ ID NO: 68 (shmiR17).

In another particular example, the AAV comprises: (a) a viral capsid protein from AAV8 comprising a modified VP1 sequence having the modifications A1S, A26E, Q40R, K43D, A44S and Q64K relative to the corresponding wild-type sequence set forth in SEQ ID NO: 91 (e.g., a modified VP1 sequence comprising the sequence set forth in SEQ ID NO: 92); and (b) a polynucleotide sequence comprising (i) a ddRNAi construct comprising a nucleic acid comprising a sequence which encodes shmiR13 as described herein and shmiR17 as described herein; and (ii) a PABPN1 construct comprising a nucleic acid comprising a sequence encoding a functional PABPN1 protein having a mRNA transcript which is not targeted by the shmiR(s) encoded by the ddRNAi construct (e.g., a codon-optimised sequence set forth in SEQ ID NO: 73). The polynucleotide at (b) may be flanked by AAV inverted terminal repeat (ITR) sequences from AAV2 set forth in SEQ ID NO: 95 and SEQ ID NO: 96. The polynucleotide at (b) may be flanked by AAV inverted terminal repeat (ITR) sequences from AAV2 set forth in SEQ ID NO: 95 and SEQ ID NO: 96. In some embodiments, the ddRNAi construct comprises a nucleic acid comprising or consisting of a DNA sequence encoding a shmiR comprising an effector sequence set forth in SEQ ID NO: 31 and an effector complement sequence which is substantially complementary to the sequence set forth in SEQ ID NO: 31 e.g., an effector complement sequence set forth in SEQ ID NO: 30 (shmiR13), and a nucleic acid comprising or consisting of a DNA sequence encoding a shmiR comprising an effector sequence set forth in SEQ ID NO: 39 and an effector complement sequence which is substantially complementary to the sequence set forth in SEQ ID NO: 39 e.g., an effector complement sequence set forth in SEQ ID NO: 38 (shmiR17). For example, the ddRNAi construct in accordance with this example can comprise a nucleic acid comprising or consisting of the DNA sequence set forth in SEQ ID NO: 64 (shmiR13), and a nucleic acid comprising or consisting of the DNA sequence set forth in SEQ ID NO: 68 (shmiR17).

In each of the foregoing examples, the polynucleotide encoding the ddRNAi construct and the PABPN1 construct is operably-linked to one or more promoters suitable for expression of the shmiRs and the PABPN1 protein in mammalian cells. In one example, the promoter may be a muscle-specific promoter. Suitable muscle-specific promoters are described herein.

The AAV of the disclosure may comprise one large AAV Rep protein selected from Rep78 and Rep68 and at least one small AAV Rep protein selected from Rep52 and Rep40.

In this regard, the AAV genome comprises Rep genes (i.e. Rep78 and Rep52), the proteins encoded by which function in the replication of the viral genome. A splicing event in the Rep ORF results in the expression of four Rep proteins (i.e. Rep78, Rep68, Rep52 and Rep40). However, it has been shown that the unspliced mRNA, encoding Rep78 and Rep52 proteins, in insect cells is sufficient for AAV vector production. Accordingly, in one example, the AAV comprises one large AAV replication Rep protein selected from Rep78 and Rep68 and at least one small AAV Rep protein selected from Rep52 and Rep40. In one example, the AAV comprises Rep78 and Rep52. In one example, the AAV comprises Rep78 and Rep40. In one example, the AAV comprises Rep68 and Rep52. In one example, the AAV comprises Rep68 and Rep40. In one example, the AAV comprises Rep78, Rep68, Rep52 and Rep40. In each of the foregoing examples, the respective small and large Rep proteins can be from the same AAV serotype as the viral capsid protein. Alternatively, the respective small and large Rep proteins can be from an AAV serotype other than that of the viral capsid protein e.g., the Rep proteins can be from AAV serotype 2. In this regard, Rep sequences are particularly conserved among most serotypes and it has been reported that Rep sequences efficiently cross-complement in insect cells.

Any nucleotide sequence can be incorporated for later expression in a mammalian cell transfected with the AAV of the present disclosure, as long as the constructs remain within the packaging capacity of the AAV virion.

As described herein, the AAV described herein can have improved functionality when produced in an insect cell relative to an AAV comprising the corresponding wildtype VP1 sequence.

Methods and Reagents for Making AAV with a Modified VP1

Methods for producing AAVs are known in the art. As described, the AAVs of the disclosure have improved functionality (e.g., improved endosomal escape activity) when produced in insect cells relative to an AAV comprising the corresponding wildtype VP1 sequence. Accordingly, methods and reagents for producing AAVs in insect cells are contemplated. In some examples, insect cell-compatible vectors i.e., a baculovirus vector, may be used or producing AAVs of the disclosure.

In one example, the present disclosure provides a plurality of baculovirus vectors for producing AAVs of the disclosure in insect cells. The plurality of baculovirus vectors may comprise:

(i) a first baculovirus vector comprising a nucleic acid molecule encoding an AAV viral capsid protein with the modified VP1 sequence as described herein; and
(ii) a second baculovirus vector comprising a polynucleotide encoding the ddRNAi construct and PABPN1 construct as described herein, flanked by AAV inverted terminal repeat (ITR) sequences.

In one example, the AAV ITR sequences are from the same serotype as the viral capsid protein encoded by the nucleic acid molecule within the first baculovirus vector. In another example, the AAV ITR sequences are from another AAV serotype e.g., AAV2. In some examples, the ITR sequences are from AAV serotype 2 and comprise the sequences set forth in SEQ ID NO: 95 and/or SEQ ID NO: 96.

In some examples, the AAV comprises capsid protein from AAV9 comprising a modified VP1 as described herein. In other examples, the AAV comprises capsid protein from AAV8 comprising a modified VP1 as described herein. Accordingly, the first baculovirus vector may comprise a nucleic acid molecule encoding a viral capsid protein from AAV8 or AAV9 with a modified VP1 sequence. Modified VP1 sequences for AAVs comprising a capsid protein from AAV9 or AAV8 have been described herein and shall be taken to apply mutatis mutandis to examples of the disclosure describing baculovirus vectors for producing AAVs of the disclosure unless specifically stated otherwise.

As described herein, the second baculovirus vector comprises a ddRNAi construct encoding one or more shmiRs targeting PABPN1. Exemplary ddRNAi constructs encoding shmiRs, including combinations of shmiRs, targeting PABPN1 are described herein and shall be taken to apply mutatis mutandis to examples of the disclosure describing baculovirus vectors for producing the AAVs of the disclosure unless specifically stated otherwise. In one particular example, the second baculovirus vector may comprise comprises a ddRNAi construct encoding shmiR13 and shmiR17, and a polynucleotide construct comprising a sequence encoding the functional PABPN1 protein that is codon optimised such that its mRNA transcript is not targeted by the shmiRs of the ddRNAi construct (e.g., a sequence set forth in SEQ ID NO: 73). For example, the second baculovirus vector may comprise a ddRNAi construct comprising or consisting of a DNA sequence encoding a shmiR comprising an effector sequence set forth in SEQ ID NO: 31 and an effector complement sequence which is substantially complementary to the sequence set forth in SEQ ID NO: 31 e.g., an effector complement sequence set forth in SEQ ID NO: 30 (shmiR13), and a nucleic acid comprising or consisting of a DNA sequence encoding a shmiR comprising an effector sequence set forth in SEQ ID NO: 39 and an effector complement sequence which is substantially complementary to the sequence set forth in SEQ ID NO: 39 e.g., an effector complement sequence set forth in SEQ ID NO: 38 (shmiR17). For example, the second baculovirus vector may comprise a ddRNAi construct comprising a nucleic acid comprising or consisting of the DNA sequence set forth in SEQ ID NO: 64 (shmiR13), and a nucleic acid comprising or consisting of the DNA sequence set forth in SEQ ID NO: 68 (shmiR17).

In each of the foregoing examples, the polynucleotide encoding the ddRNAi construct and the PABPN1 construct may be operably-linked to a promoter. In one example, the promoter may be a muscle-specific promoter.

Similarly, the nucleic acid molecule encoding the AAV viral capsid protein can be operably-linked to a promoter which is suitable for expression of the capsid protein in an insect cell. Suitable promoters for expression in insect cells are known in the art and contemplated for use herein. In this regard, methodologies for molecular engineering and expression of polypeptides in insect cells have been previously described, for example, in Summers and Smith, A Manual of Methods for Baculovirus Vectors and Insect Culture Procedures, Texas Agricultural Experimental Station Bull. No. 7555, College Station, Tex. (1986); Luckow., In Prokop et al., Cloning and Expression of Heterologous Genes in Insect Cells with Baculovirus Vectors' Recombinant DNA Technology and Applications, 97-152 (1991); King, L. A and R. D. Possee, The baculovirus expression system, Chapman and Hall, United Kingdom (1992); O'Reilly, D. R., L. K. Miller, V. A Luckow, Baculovirus Expression Vectors: A Laboratory Manual, New York (1992); W. H. Freeman and Richardson, C. D., Baculovirus Expression Protocols, Methods in Molecular Biology, volume 39 (1992); U.S. Pat. No. 4,745,051; US2003148506; WO2003/074714; Kotin R M (2011) Hum. Mol. Genet., 20(R1):R2-R6; Aucoin et al., (2006) Biotechnol. Bioeng. 95(6):1081-1092; and van Oers et al., (2015) J. Gen. Virol. 96:6-23. Promoters and other such regulatory element which are known in the art are clearly contemplated for use in the nucleic acid of the disclosure. In some embodiments, the promoter is a polyhedron promoter or a p10 promoter.

In accordance with an example in which the first baculovirus vector does not encode AAV Rep proteins, the plurality of baculovirus vectors further comprises:

(iii) a third baculovirus vector comprising a polynucleotide sequence encoding at least one large AAV Rep protein selected from Rep78 and Rep68 and at least one small AAV Rep protein selected from Rep52 and Rep40.

In this regard, the AAV genome comprises Rep genes (i.e. Rep78 and Rep52), the proteins encoded by which function in the replication of the viral genome. A splicing event in the Rep ORF results in the expression of four Rep proteins (i.e. Rep78, Rep68, Rep52 and Rep40). However, it has been shown that the unspliced mRNA, encoding Rep78 and Rep52 proteins, in insect cells is sufficient for AAV vector production. Accordingly, in one example, the third baculovirus vector comprises a polynucleotide sequence encoding at least one large AAV replication Rep protein selected from Rep78 and Rep68 and at least one small AAV Rep protein selected from Rep52 and Rep40. In one example, the third baculovirus vector comprises a polynucleotide sequence encoding Rep78 and Rep52. In one example, the third baculovirus vector comprises a polynucleotide sequence encoding Rep78 and Rep40. In one example, the third baculovirus vector comprises a polynucleotide sequence encoding Rep68 and Rep52. In one example, the third baculovirus vector comprises a polynucleotide sequence encoding Rep68 and Rep40. In one example, the third baculovirus vector comprises a polynucleotide sequence encoding Rep78, Rep68, Rep52 and Rep40. In each of the foregoing examples, the respective small and large Rep proteins can be from the same AAV serotype as the viral capsid protein. Alternatively, the respective small and large Rep proteins can be from an AAV serotype other than that of the viral capsid protein e.g., the Rep proteins can be from AAV serotype 2. In this regard, Rep sequences are particularly conserved among most serotypes and it has been reported that Rep sequences efficiently cross-complement in insect cells.

In each of the foregoing examples describing the plurality of baculovirus vectors, the polynucleotide sequence encoding the Rep proteins within the third baculovirus vector can be operably-linked to a promoter for expression of the Rep proteins in an insect cell. Suitable promoters for expression in insect cells are known in the art and contemplated for use herein. In one particular example, the promoter can be, e.g., a polyhedron promoter or a p10 promoter. The nucleotide sequences encoding the respective Rep proteins can be operably-linked to the same promoter. Alternatively, each sequence encoding a Rep protein can operably-linked to its own promoter.

At least one of the baculovirus vectors in the plurality will comprise a polynucleotide encoding the assembly-activating protein (AAP) as required for the AAV capsid assembly. In one example, the baculovirus vector encoding the capsid protein comprises a polynucleotide encoding an AAP. In alternative example, the baculovirus encoding the Rep proteins and/or the baculovirus encoding the ddRNAi construct and PABPN1 construct, comprises a polynucleotide encoding an AAP.

Methods of producing AAV suitable for use in gene therapy (e.g., replication incompetent AAV) are well known in the art and contemplated herein. For example, AAV may be produced in insect cells using a baculovirus system, for example, as described in US20120028357 A1, WO2007046703, US20030148506 A1, WO2017184879, US20040197895 A1 and WO2007148971, the content of which is described by reference herein. Recombinant AAV may also be produced in mammalian cells, both adherent and suspension cells, methods for which are described in WO2015031686, WO2009097129, WO2007127264, WO1997009441 and WO2001049829, the content of which is described by reference herein. Methods of producing recombinant AAV for use in gene therapy are also described in Berns K I and Giraud C (1996) Biology of adeno-associated virus. *Curr Top Microbiol Immunol* 218:1-23, Snyder and Flotte (2002) Curr. Opin. Biotechnol., 13:418-423, and Synder R O and Moullier P, *Adeno-associated virus; methods and protocols*. New York: Humana Press (2011), the contents of which are incorporated by reference herein.

ddRNAi Constructs

As described herein, the AAV of the disclosure comprises a DNA-directed RNAi (ddRNAi) construct comprising a DNA sequence which encodes a short hairpin micro-RNA (shmiR). A shmiR encoded by the ddRNAi construct comprises:

an effector sequence of at least 17 nucleotides in length;
an effector complement sequence;
a stemloop sequence; and
primary micro RNA (pri-miRNA) backbone.

In one example, the effector sequence is substantially complementary to a region of corresponding length in an RNA transcript set forth in any one of SEQ ID NOs: 1-13. Preferably, the effector sequence will be less than 30 nucleotides in length. For example, a suitable effector sequence may be in the range of 17-29 nucleotides in length. In a particularly preferred example, the effector sequence will be 21 nucleotides in length. More preferably, the effector sequence will be 21 nucleotides in length and the effector complement sequence will be 20 nucleotides in length.

In certain embodiments, the shmiR encoded by the ddRNAi construct comprises an effector sequence which is substantially complementary to a region of corresponding length in an RNA transcript comprising or consisting of the sequence set forth in any one of SEQ ID NOs: 1-13 (i.e., SEQ ID NO: 1, SEQ ID NO: 2, SEQ ID NO: 3, SEQ ID NO: 4, SEQ ID NO: 5, SEQ ID NO: 5, SEQ ID NO: 7, SEQ ID NO: 8, SEQ ID NO: 9, SEQ ID NO: 10, SEQ ID NO: 11, SEQ ID NO: 12, or SEQ ID NO: 13). For example, the effector sequence may be substantially complementary to a region of corresponding length in an RNA transcript comprising or consisting of the sequence set forth in any one of SEQ ID NOs: 1-13 and contain 4 mismatch bases relative thereto. For example, the effector sequence may be substantially complementary to a region of corresponding length in an RNA transcript comprising or consisting of the sequence set forth in any one of SEQ ID NOs: 1-13 and contain 3 mismatch bases relative thereto. For example, the effector sequence may be substantially complementary to a region of corresponding length in an RNA transcript comprising or consisting of the sequence set forth in any one of SEQ ID NOs: 1-13 and contain 2 mismatch bases relative thereto. For example, the effector sequence may be substantially complementary to a region of corresponding length in an RNA transcript comprising or consisting of the sequence set forth in any one of SEQ ID NOs: 1-13 and contain 1 mismatch base relative thereto. For example, the effector sequence may be 100% complementary to a region of corresponding length in an RNA transcript comprising or consisting of the sequence set forth in any one of SEQ ID NOs: 1-13.

In one example, the shmiR encoded by the ddRNAi construct comprises an effector sequence which is substantially complementary to a region of corresponding length in an RNA transcript comprising or consisting of the sequence set forth in SEQ ID NO: 9. A shmiR in accordance with this example is also referred to herein as "shmiR13". For example, the effector sequence may be substantially complementary to a region of corresponding length in an RNA transcript comprising or consisting of the sequence set forth in SEQ ID NO: 9 and contain 4 mismatch bases relative thereto. For example, the effector sequence may be substantially complementary to a region of corresponding length in an RNA transcript comprising or consisting of the sequence set forth in SEQ ID NO: 9 and contain 3 mismatch bases relative thereto. For example, the effector sequence may be substantially complementary to a region of corresponding length in an RNA transcript comprising or consisting of the sequence set forth in SEQ ID NO: 9 and contain 2 mismatch bases relative thereto. For example, the effector sequence may be substantially complementary to a region of corresponding length in an RNA transcript comprising or consisting of the sequence set forth in SEQ ID NO: 9 and contain 1 mismatch base relative thereto. For example, the effector sequence may be 100% complementary to a region of corresponding length in an RNA transcript comprising or consisting of the sequence set forth in SEQ ID NO: 9.

In one example, the shmiR encoded by the ddRNAi construct comprises an effector sequence which is substantially complementary to a region of corresponding length in an RNA transcript comprising or consisting of the sequence set forth in SEQ ID NO: 13. A shmiR in accordance with this example is also referred to herein as "shmiR17". For example, the effector sequence may be substantially complementary to a region of corresponding length in an RNA transcript comprising or consisting of the sequence set forth in SEQ ID NO: 13 and contain 4 mismatch bases relative thereto. For example, the effector sequence may be substantially complementary to a region of corresponding length in an RNA transcript comprising or consisting of the sequence set forth in SEQ ID NO: 13 and contain 3 mismatch bases relative thereto. For example, the effector sequence may be substantially complementary to a region of corresponding length in an RNA transcript comprising or consisting of the sequence set forth in SEQ ID NO: 13 and contain 2 mismatch bases relative thereto. For example, the effector sequence may be substantially complementary to a region of corresponding length in an RNA transcript comprising or consisting of the sequence set forth in SEQ ID NO: 13 and contain 1 mismatch base relative thereto. For example, the effector sequence may be 100% complementary to a region of corresponding length in an RNA transcript comprising or consisting of the sequence set forth in SEQ ID NO: 13.

In accordance with an example in which the effector sequence of the shmiR is substantially complementary to a region of corresponding length in a PABPN1 miRNA transcript described herein and contains 1, 2, 3 or 4 mismatch base(s) relative thereto, it is preferred that the mismatch(es) are not located within the region corresponding to the seed region of the shmiR i.e., nucleotides 2-8 of the effector sequence.

In some examples, the ddRNAi construct may comprise a DNA sequence encoding a shmiR comprising: (i) an effector sequence which is substantially complementary to the sequence set forth in SEQ ID NO:14 with the exception of 1, 2, 3 or 4 base mismatches, provided that the effector sequence is capable of forming a duplex with a sequence set forth in SEQ ID NO:14; and (ii) an effector complement sequence comprising a sequence which is substantially complementary to the effector sequence. For example, the shmiR encoded by the ddRNAi construct may comprise an effector sequence set forth in SEQ ID NO:15 and an effector complement sequence which is substantially complementary to the sequence set forth in SEQ ID NO:15 and capable of forming a duplex therewith. The effector complement sequence which is substantially complementary to the sequence set forth in SEQ ID NO:15 may be the sequence set forth in SEQ ID NO:14. A shmiR in accordance with this example is hereinafter designated "shmiR2".

In one example, the ddRNAi construct may comprise a DNA sequence encoding a shmiR comprising: (i) an effector sequence which is substantially complementary to the sequence set forth in SEQ ID NO:16 with the exception of 1, 2, 3 or 4 base mismatches, provided that the effector sequence is capable of forming a duplex with a sequence set forth in SEQ ID NO:16; and (ii) an effector complement sequence comprising a sequence which is substantially complementary to the effector sequence. For example, the shmiR encoded by the ddRNAi construct may comprise an effector sequence set forth in SEQ ID NO:17 and an effector complement sequence which is substantially complementary to the sequence set forth in SEQ ID NO:17 and capable of forming a duplex therewith. The effector complement sequence which is substantially complementary to the sequence set forth in SEQ ID NO:17 may be the sequence set forth in SEQ ID NO:16. A shmiR in accordance with this example is hereinafter designated "shmiR3".

In one example, the ddRNAi construct may comprise a DNA sequence encoding a shmiR comprising: (i) an effector sequence which is substantially complementary to the sequence set forth in SEQ ID NO:18 with the exception of 1, 2, 3 or 4 base mismatches, provided that the effector sequence is capable of forming a duplex with a sequence set forth in SEQ ID NO:18; and (ii) an effector complement sequence comprising a sequence which is substantially complementary to the effector sequence. For example, the shmiR encoded by the ddRNAi construct may comprise an effector sequence set forth in SEQ ID NO:19 and an effector complement sequence which is substantially complementary to the sequence set forth in SEQ ID NO:19 and capable of forming a duplex therewith. The effector complement sequence which is substantially complementary to the sequence set forth in SEQ ID NO:19 may be the sequence set forth in SEQ ID NO:18. A shmiR in accordance with this example is hereinafter designated "shmiR4".

In one example, the ddRNAi construct may comprise a DNA sequence encoding a shmiR comprising: (i) an effector sequence which is substantially complementary to the sequence set forth in SEQ ID NO:20 with the exception of 1, 2, 3 or 4 base mismatches, provided that the effector sequence is capable of forming a duplex with a sequence set forth in SEQ ID NO:20; and (ii) an effector complement sequence comprising a sequence which is substantially complementary to the effector sequence. For example, the shmiR encoded by the ddRNAi construct may comprise an effector sequence set forth in SEQ ID NO:21 and an effector complement sequence which is substantially complementary to the sequence set forth in SEQ ID NO:21 and capable of forming a duplex therewith. The effector complement sequence which is substantially complementary to the sequence set forth in SEQ ID NO:21 may be the sequence set forth in SEQ ID NO:20. A shmiR in accordance with this example is hereinafter designated "shmiR5".

In one example, the ddRNAi construct may comprise a DNA sequence encoding a shmiR comprising: (i) an effector sequence which is substantially complementary to the sequence set forth in SEQ ID NO:22 with the exception of 1, 2, 3 or 4 base mismatches, provided that the effector sequence is capable of forming a duplex with a sequence set forth in SEQ ID NO:22; and (ii) an effector complement sequence comprising a sequence which is substantially complementary to the effector sequence. For example, the shmiR encoded by the ddRNAi construct may comprise an effector sequence set forth in SEQ ID NO:23 and an effector complement sequence which is substantially complementary to the sequence set forth in SEQ ID NO:23 and capable of forming a duplex therewith. The effector complement sequence which is substantially complementary to the sequence set forth in SEQ ID NO:23 may be the sequence set forth in SEQ ID NO:22. A shmiR in accordance with this example is hereinafter designated "shmiR6".

In one example, the ddRNAi construct may comprise a DNA sequence encoding a shmiR comprising: (i) an effector sequence which is substantially complementary to the sequence set forth in SEQ ID NO:24 with the exception of 1, 2, 3 or 4 base mismatches, provided that the effector sequence is capable of forming a duplex with a sequence set forth in SEQ ID NO:24; and (ii) an effector complement sequence comprising a sequence which is substantially complementary to the effector sequence. For example, the shmiR encoded by the ddRNAi construct may comprise an effector sequence set forth in SEQ ID NO:25 and an effector complement sequence which is substantially complementary to the sequence set forth in SEQ ID NO:25 and capable of forming a duplex therewith. The effector complement sequence which is substantially complementary to the sequence set forth in SEQ ID NO:25 may be the sequence set forth in SEQ ID NO:24. A shmiR in accordance with this example is hereinafter designated “shmiR7”.

In one example, the ddRNAi construct may comprise a DNA sequence encoding a shmiR comprising: (i) an effector sequence which is substantially complementary to the sequence set forth in SEQ ID NO:26 with the exception of 1, 2, 3 or 4 base mismatches, provided that the effector sequence is capable of forming a duplex with a sequence set forth in SEQ ID NO:26; and (ii) an effector complement sequence comprising a sequence which is substantially complementary to the effector sequence. For example, the shmiR encoded by the ddRNAi construct may comprise an effector sequence set forth in SEQ ID NO:27 and an effector complement sequence which is substantially complementary to the sequence set forth in SEQ ID NO:27 and capable of forming a duplex therewith. The effector complement sequence which is substantially complementary to the sequence set forth in SEQ ID NO:27 may be the sequence set forth in SEQ ID NO:26. A shmiR in accordance with this example is hereinafter designated “shmiR9”.

In one example, the ddRNAi construct may comprise a DNA sequence encoding a shmiR comprising: (i) an effector sequence which is substantially complementary to the sequence set forth in SEQ ID NO:28 with the exception of 1, 2, 3 or 4 base mismatches, provided that the effector sequence is capable of forming a duplex with a sequence set forth in SEQ ID NO:28; and (ii) an effector complement sequence comprising a sequence which is substantially complementary to the effector sequence. For example, the shmiR encoded by the ddRNAi construct may comprise an effector sequence set forth in SEQ ID NO:29 and an effector complement sequence which is substantially complementary to the sequence set forth in SEQ ID NO:29 and capable of forming a duplex therewith. The effector complement sequence which is substantially complementary to the sequence set forth in SEQ ID NO:29 may be the sequence set forth in SEQ ID NO:28. A shmiR in accordance with this example is hereinafter designated “shmiR11”.

In one example, the ddRNAi construct may comprise a DNA sequence encoding a shmiR comprising: (i) an effector sequence which is substantially complementary to the sequence set forth in SEQ ID NO:30 with the exception of 1, 2, 3 or 4 base mismatches, provided that the effector sequence is capable of forming a duplex with a sequence set forth in SEQ ID NO:30; and (ii) an effector complement sequence comprising a sequence which is substantially complementary to the effector sequence. For example, the shmiR encoded by the ddRNAi construct may comprise an effector sequence set forth in SEQ ID NO:31 and an effector complement sequence which is substantially complementary to the sequence set forth in SEQ ID NO:31 and capable of forming a duplex therewith. The effector complement sequence which is substantially complementary to the sequence set forth in SEQ ID NO:31 may be the sequence set forth in SEQ ID NO:30. A shmiR in accordance with this example is hereinafter designated “shmiR13”.

In one example, the ddRNAi construct may comprise a DNA sequence encoding a shmiR comprising: (i) an effector sequence which is substantially complementary to the sequence set forth in SEQ ID NO:32 with the exception of 1, 2, 3 or 4 base mismatches, provided that the effector sequence is capable of forming a duplex with a sequence set forth in SEQ ID NO:32; and (ii) an effector complement sequence comprising a sequence which is substantially complementary to the effector sequence. For example, the shmiR encoded by the ddRNAi construct may comprise an effector sequence set forth in SEQ ID NO:33 and an effector complement sequence which is substantially complementary to the sequence set forth in SEQ ID NO:33 and capable of forming a duplex therewith. The effector complement sequence which is substantially complementary to the sequence set forth in SEQ ID NO:33 may be the sequence set forth in SEQ ID NO:32. A shmiR in accordance with this example is hereinafter designated “shmiR14”.

In one example, the ddRNAi construct may comprise a DNA sequence encoding a shmiR comprising: (i) an effector sequence which is substantially complementary to the sequence set forth in SEQ ID NO:34 with the exception of 1, 2, 3 or 4 base mismatches, provided that the effector sequence is capable of forming a duplex with a sequence set forth in SEQ ID NO:34; and (ii) an effector complement sequence comprising a sequence which is substantially complementary to the effector sequence. For example, the shmiR encoded by the ddRNAi construct may comprise an effector sequence set forth in SEQ ID NO:35 and an effector complement sequence which is substantially complementary to the sequence set forth in SEQ ID NO:35 and capable of forming a duplex therewith. The effector complement sequence which is substantially complementary to the sequence set forth in SEQ ID NO:35 may be the sequence set forth in SEQ ID NO:34. A shmiR in accordance with this example is hereinafter designated “shmiR15”.

In one example, the ddRNAi construct may comprise a DNA sequence encoding a shmiR comprising: (i) an effector sequence which is substantially complementary to the sequence set forth in SEQ ID NO:36 with the exception of 1, 2, 3 or 4 base mismatches, provided that the effector sequence is capable of forming a duplex with a sequence set forth in SEQ ID NO:36; and (ii) an effector complement sequence comprising a sequence which is substantially complementary to the effector sequence. For example, the shmiR encoded by the ddRNAi construct may comprise an effector sequence set forth in SEQ ID NO:37 and an effector complement sequence which is substantially complementary to the sequence set forth in SEQ ID NO:37 and capable of forming a duplex therewith. The effector complement sequence which is substantially complementary to the sequence set forth in SEQ ID NO:37 may be the sequence set forth in SEQ ID NO:36. A shmiR in accordance with this example is hereinafter designated “shmiR16”.

In one example, the ddRNAi construct may comprise a DNA sequence encoding a shmiR comprising: (i) an effector sequence which is substantially complementary to the sequence set forth in SEQ ID NO:38 with the exception of 1, 2, 3 or 4 base mismatches, provided that the effector sequence is capable of forming a duplex with a sequence set forth in SEQ ID NO:38; and (ii) an effector complement sequence comprising a sequence which is substantially complementary to the effector sequence. For example, the shmiR encoded by the ddRNAi construct may comprise an effector sequence set forth in SEQ ID NO:39 and an effector complement sequence which is substantially complementary to the sequence set forth in SEQ ID NO:39 and capable of forming a duplex therewith. The effector complement sequence which is substantially complementary to the sequence set forth in SEQ ID NO:39 may be the sequence set forth in SEQ ID NO:38. A shmiR in accordance with this example is hereinafter designated "shmiR17".

In any of the examples described herein, the shmiR encoded by the ddRNAi construct of the disclosure may comprise, in a 5' to 3' direction:

a 5' flanking sequence of the pri-miRNA backbone;
the effector complement sequence;
the stemloop sequence;
the effector sequence; and
a 3' flanking sequence of the pri-miRNA backbone.

In any of the examples described herein, the shmiR encoded by the ddRNAi construct of the disclosure may comprise, in a 5' to 3' direction:

a 5' flanking sequence of the pri-miRNA backbone;
the effector sequence;
the stemloop sequence;
the effector complement sequence; and
a 3' flanking sequence of the pri-miRNA backbone.

Suitable loop sequences may be selected from those known in the art. However, an exemplary stemloop sequence is set forth in SEQ ID NO: 40.

Suitable primary micro RNA (pri-miRNA or pri-R) backbones for use in a nucleic acid of the disclosure may be selected from those known in the art. For example, the pri-miRNA backbone may be selected from a pri-miR-30a backbone, a pri-miR-155 backbone, a pri-miR-21 backbone and a pri-miR-136 backbone. Preferably, however, the pri-miRNA backbone is a pri-miR-30a backbone. In accordance with an example in which the pri-miRNA backbone is a pri-miR-30a backbone, the 5' flanking sequence of the pri-miRNA backbone is set forth in SEQ ID NO: 41 and the 3' flanking sequence of the pri-miRNA backbone is set forth in SEQ ID NO: 42. Thus, a ddRNAi construct encoding a shmiR of the disclosure (e.g., one or more of one or more of shmiR2-shmiR7, shmiR9, shmiR11 and shmiR13-shmiR17 described herein) may comprise a DNA sequence encoding the sequence set forth in SEQ ID NO: 41 and a DNA sequence encoding the sequence set forth in SEQ ID NO: 42.

In one example, the ddRNAi construct may comprise a DNA sequence selected from the sequence set forth in any one of SEQ ID NOs: 56-68.

In one example, the ddRNAi construct comprises or consists of a DNA sequence set forth in SEQ ID NO: 56 and encodes a shmiR (shmiR2) comprising or consisting of the sequence set forth in SEQ ID NO: 43.

In one example, the ddRNAi construct comprises or consists of a DNA sequence set forth in SEQ ID NO: 57 and encodes a shmiR (shmiR3) comprising or consisting of the sequence set forth in SEQ ID NO: 44.

In one example, the ddRNAi construct comprises or consists of a DNA sequence set forth in SEQ ID NO: 58 and encodes a shmiR (shmiR4) comprising or consisting of the sequence set forth in SEQ ID NO: 45.

In one example, the ddRNAi construct comprises or consists of a DNA sequence set forth in SEQ ID NO: 59 and encodes a shmiR (shmiR5) comprising or consisting of the sequence set forth in SEQ ID NO: 46.

In one example, the ddRNAi construct comprises or consists of a DNA sequence set forth in SEQ ID NO: 60 and encodes a shmiR (shmiR6) comprising or consisting of the sequence set forth in SEQ ID NO: 47.

In one example, the ddRNAi construct comprises or consists of a DNA sequence set forth in SEQ ID NO: 61 and encodes a shmiR (shmiR7) comprising or consisting of the sequence set forth in SEQ ID NO: 48.

In one example, the ddRNAi construct comprises or consists of a DNA sequence set forth in SEQ ID NO: 62 and encodes a shmiR (shmiR9) comprising or consisting of the sequence set forth in SEQ ID NO: 49.

In one example, the ddRNAi construct comprises or consists of a DNA sequence set forth in SEQ ID NO: 63 and encodes a shmiR (shmiR11) comprising or consisting of the sequence set forth in SEQ ID NO: 50.

In one example, the ddRNAi construct comprises or consists of a DNA sequence set forth in SEQ ID NO: 64 and encodes a shmiR (shmiR13) comprising or consisting of the sequence set forth in SEQ ID NO: 51.

In one example, the ddRNAi construct comprises or consists of a DNA sequence set forth in SEQ ID NO: 65 and encodes a shmiR (shmiR14) comprising or consisting of the sequence set forth in SEQ ID NO: 52.

In one example, the ddRNAi construct comprises or consists of a DNA sequence set forth in SEQ ID NO: 66 and encodes a shmiR (shmiR15) comprising or consisting of the sequence set forth in SEQ ID NO: 53.

In one example, the ddRNAi construct comprises or consists of a DNA sequence set forth in SEQ ID NO: 67 and encodes a shmiR (shmiR16) comprising or consisting of the sequence set forth in SEQ ID NO: 54.

In one example, the ddRNAi construct comprises or consists of a DNA sequence set forth in SEQ ID NO: 68 and encodes a shmiR (shmiR17) comprising or consisting of the sequence set forth in SEQ ID NO: 55.

An exemplary ddRNAi construct of the disclosure encodes one or more shmiRs selected from shmiR2, shmiR3, shmiR5, shmiR9, shmiR13, shmiR14 and shmiR17 as described herein. A ddRNAi construct encoding one or more shmiRs selected from shmiR3, shmiR13, shmiR14 and shmiR17 as described herein is particularly preferred. For example, the ddRNAi construct may encode shmiR13 as described herein. For example, the ddRNAi construct may encode shmiR17 as described herein.

It will be understood by a person of skill in the art that the ddRNAi construct described herein may encode a plurality of shmiRs targeting the RNA transcript corresponding to a PABPN1 protein which is causative of OPMD.

Accordingly, in one example, the ddRNAi construct comprise two or more nucleic acids encoding shmiRs as described herein, such as two, or three, or four, or five, or six, or seven, or eight, or nine, or ten nucleic acids encoding shmiRs as described herein.

In one example, the ddRNAi construct comprises a nucleic acid comprising or consisting of a DNA sequence encoding shmiR2, and at least one other nucleic acid of the disclosure which encodes a shmiR targeting a region of a PABPN1 mRNA transcript. Exemplary nucleic acids encoding shmiR2 are described herein and shall be taken to apply mutatis mutandis to this example of the disclosure. In one example, the ddRNAi construct comprises a nucleic acid which comprises or consists of a DNA sequence set forth in SEQ ID NO: 56 and which encodes a shmiR comprising or consisting of the sequence set forth in SEQ ID NO: 43, and at least one other nucleic acid of the disclosure which encodes a shmiR targeting a region of a PABPN1 mRNA transcript. For example, the ddRNAi construct may comprise (i) a nucleic acid comprising or consisting of a DNA sequence set forth in SEQ ID NO: 56 (shmiR2), and (ii) a nucleic acid comprising or consisting of a DNA sequence encoding one of shmiR3-shmiR7, shmiR9, shmiR11 or shmiR13-shmiR17.

In one example, the ddRNAi construct comprises a nucleic acid comprising or consisting of a DNA sequence encoding shmiR3, and at least one other nucleic acid of the disclosure which encodes a shmiR targeting a region of a PABPN1 mRNA transcript. Exemplary nucleic acids encoding shmiR3 are described herein and shall be taken to apply mutatis mutandis to this example of the disclosure. In one example, the ddRNAi construct comprises a nucleic acid which comprises or consists of a DNA sequence set forth in SEQ ID NO: 57 and which encodes a shmiR comprising or consisting of the sequence set forth in SEQ ID NO: 44, and at least one other nucleic acid of the disclosure which encodes a shmiR targeting a region of a PABPN1 mRNA transcript. For example, the ddRNAi construct may comprise (i) a nucleic acid comprising or consisting of a DNA sequence set forth in SEQ ID NO: 57 (shmiR3), and (ii) a nucleic acid comprising or consisting of a DNA sequence encoding one of shmiR2, shmiR4-shmiR7, shmiR9, shmiR11 or shmiR13-shmiR17.

In one example, the ddRNAi construct comprises a nucleic acid comprising or consisting of a DNA sequence encoding shmiR4, and at least one other nucleic acid of the disclosure which encodes a shmiR targeting a region of a PABPN1 mRNA transcript. Exemplary nucleic acids encoding shmiR4 are described herein and shall be taken to apply mutatis mutandis to this example of the disclosure. In one example, the ddRNAi construct comprises a nucleic acid which comprises or consists of a DNA sequence set forth in SEQ ID NO: 58 and which encodes a shmiR comprising or consisting of the sequence set forth in SEQ ID NO: 45, and at least one other nucleic acid of the disclosure which encodes a shmiR targeting a region of a PABPN1 mRNA transcript. For example, the ddRNAi construct may comprise (i) a nucleic acid comprising or consisting of a DNA sequence set forth in SEQ ID NO: 58 (shmiR4), and (ii) a nucleic acid comprising or consisting of a DNA sequence encoding one of shmiR2, shmiR3, shmiR5-shmiR7, shmiR9, shmiR11 or shmiR13-shmiR17.

In one example, the ddRNAi construct comprises a nucleic acid comprising or consisting of a DNA sequence encoding shmiR5, and at least one other nucleic acid of the disclosure which encodes a shmiR targeting a region of a PABPN1 mRNA transcript. Exemplary nucleic acids encoding shmiR5 are described herein and shall be taken to apply mutatis mutandis to this example of the disclosure. In one example, the ddRNAi construct comprises a nucleic acid which comprises or consists of a DNA sequence set forth in SEQ ID NO: 59 and which encodes a shmiR comprising or consisting of the sequence set forth in SEQ ID NO: 46, and at least one other nucleic acid of the disclosure which encodes a shmiR targeting a region of a PABPN1 mRNA transcript. For example, the ddRNAi construct may comprise (i) a nucleic acid comprising or consisting of a DNA sequence set forth in SEQ ID NO: 59 (shmiR5), and (ii) a nucleic acid comprising or consisting of a DNA sequence encoding one of shmiR2-shmiR4, shmiR6-shmiR7, shmiR9, shmiR11 or shmiR13-shmiR17.

In one example, the ddRNAi construct comprises a nucleic acid comprising or consisting of a DNA sequence encoding shmiR6, and at least one other nucleic acid of the disclosure which encodes a shmiR targeting a region of a PABPN1 mRNA transcript. Exemplary nucleic acids encoding shmiR6 are described herein and shall be taken to apply mutatis mutandis to this example of the disclosure. In one example, the ddRNAi construct comprises a nucleic acid which comprises or consists of a DNA sequence set forth in SEQ ID NO: 60 and which encodes a shmiR comprising or consisting of the sequence set forth in SEQ ID NO: 47, and at least one other nucleic acid of the disclosure which encodes a shmiR targeting a region of a PABPN1 mRNA transcript. For example, the ddRNAi construct may comprise (i) a nucleic acid comprising or consisting of a DNA sequence set forth in SEQ ID NO: 60 (shmiR6), and (ii) a nucleic acid comprising or consisting of a DNA sequence encoding one of shmiR2-shmiR5, shmiR7, shmiR9, shmiR11 or shmiR13-shmiR17.

In one example, the ddRNAi construct comprises a nucleic acid comprising or consisting of a DNA sequence encoding shmiR7, and at least one other nucleic acid of the disclosure which encodes a shmiR targeting a region of a PABPN1 mRNA transcript. Exemplary nucleic acids encoding shmiR7 are described herein and shall be taken to apply mutatis mutandis to this example of the disclosure. In one example, the ddRNAi construct comprises a nucleic acid which comprises or consists of a DNA sequence set forth in SEQ ID NO: 61 and which encodes a shmiR comprising or consisting of the sequence set forth in SEQ ID NO: 48, and at least one other nucleic acid of the disclosure which encodes a shmiR targeting a region of a PABPN1 mRNA transcript. For example, the ddRNAi construct may comprise (i) a nucleic acid comprising or consisting of a DNA sequence set forth in SEQ ID NO: 61 (shmiR7), and (ii) a nucleic acid comprising or consisting of a DNA sequence encoding one of shmiR2-shmiR6, shmiR9, shmiR11 or shmiR13-shmiR17.

In one example, the ddRNAi construct comprises a nucleic acid comprising or consisting of a DNA sequence encoding shmiR9, and at least one other nucleic acid of the disclosure which encodes a shmiR targeting a region of a PABPN1 mRNA transcript. Exemplary nucleic acids encoding shmiR9 are described herein and shall be taken to apply mutatis mutandis to this example of the disclosure. In one example, the ddRNAi construct comprises a nucleic acid which comprises or consists of a DNA sequence set forth in SEQ ID NO: 62 and which encodes a shmiR comprising or consisting of the sequence set forth in SEQ ID NO: 49, and at least one other nucleic acid of the disclosure which encodes a shmiR targeting a region of a PABPN1 mRNA transcript. For example, the ddRNAi construct may comprise (i) a nucleic acid comprising or consisting of a DNA sequence set forth in SEQ ID NO: 62 (shmiR9), and (ii) a nucleic acid comprising or consisting of a DNA sequence encoding one of shmiR2-shmiR7, shmiR11 or shmiR13-shmiR17.

In one example, the ddRNAi construct comprises a nucleic acid comprising or consisting of a DNA sequence encoding shmiR11, and at least one other nucleic acid of the disclosure which encodes a shmiR targeting a region of a PABPN1 mRNA transcript. Exemplary nucleic acids encoding shmiR11 are described herein and shall be taken to apply mutatis mutandis to this example of the disclosure. In one example, the ddRNAi construct comprises a nucleic acid which comprises or consists of a DNA sequence set forth in SEQ ID NO: 63 and which encodes a shmiR comprising or consisting of the sequence set forth in SEQ ID NO: 50, and at least one other nucleic acid of the disclosure which encodes a shmiR targeting a region of a PABPN1 mRNA transcript. For example, the ddRNAi construct may comprise (i) a nucleic acid comprising or consisting of a DNA sequence set forth in SEQ ID NO: 63 (shmiR11), and (ii) a nucleic acid comprising or consisting of a DNA sequence encoding one of shmiR2-shmiR7, shmiR9 or shmiR13-shmiR17.

In one example, the ddRNAi construct comprises a nucleic acid comprising or consisting of a DNA sequence encoding shmiR13, and at least one other nucleic acid of the disclosure which encodes a shmiR targeting a region of a PABPN1 mRNA transcript. Exemplary nucleic acids encoding shmiR13 are described herein and shall be taken to apply mutatis mutandis to this example of the disclosure. In one example, the ddRNAi construct comprises a nucleic acid which comprises or consists of a DNA sequence set forth in SEQ ID NO: 64 and which encodes a shmiR comprising or consisting of the sequence set forth in SEQ ID NO: 51, and at least one other nucleic acid of the disclosure which encodes a shmiR targeting a region of a PABPN1 mRNA transcript. For example, the ddRNAi construct may comprise (i) a nucleic acid comprising or consisting of a DNA sequence set forth in SEQ ID NO: 64 (shmiR13), and (ii) a nucleic acid comprising or consisting of a DNA sequence encoding one of shmiR2-shmiR7, shmiR9, shmiR11 or shmiR14-shmiR17.

In one example, the ddRNAi construct comprises a nucleic acid comprising or consisting of a DNA sequence encoding shmiR14, and at least one other nucleic acid of the disclosure which encodes a shmiR targeting a region of a PABPN1 mRNA transcript. Exemplary nucleic acids encoding shmiR14 are described herein and shall be taken to apply mutatis mutandis to this example of the disclosure. In one example, the ddRNAi construct comprises a nucleic acid which comprises or consists of a DNA sequence set forth in SEQ ID NO: 65 and which encodes a shmiR comprising or consisting of the sequence set forth in SEQ ID NO: 52, and at least one other nucleic acid of the disclosure which encodes a shmiR targeting a region of a PABPN1 mRNA transcript. For example, the ddRNAi construct may comprise (i) a nucleic acid comprising or consisting of a DNA sequence set forth in SEQ ID NO: 65 (shmiR14), and (ii) a nucleic acid comprising or consisting of a DNA sequence encoding one of shmiR2-shmiR7, shmiR9, shmiR11 or shmiR13, shmiR15-shmiR17.

In one example, the ddRNAi construct comprises a nucleic acid comprising or consisting of a DNA sequence encoding shmiR15, and at least one other nucleic acid of the disclosure which encodes a shmiR targeting a region of a PABPN1 mRNA transcript. Exemplary nucleic acids encoding shmiR15 are described herein and shall be taken to apply mutatis mutandis to this example of the disclosure. In one example, the ddRNAi construct comprises a nucleic acid which comprises or consists of a DNA sequence set forth in SEQ ID NO: 66 and which encodes a shmiR comprising or consisting of the sequence set forth in SEQ ID NO: 53, and at least one other nucleic acid of the disclosure which encodes a shmiR targeting a region of a PABPN1 mRNA transcript. For example, the ddRNAi construct may comprise (i) a nucleic acid comprising or consisting of a DNA sequence set forth in SEQ ID NO: 66 (shmiR15), and (ii) a nucleic acid comprising or consisting of a DNA sequence encoding one of shmiR2-shmiR7, shmiR9, shmiR11 or shmiR13-shmiR14, or shmiR16-shmiR17.

In one example, the ddRNAi construct comprises a nucleic acid comprising or consisting of a DNA sequence encoding shmiR16, and at least one other nucleic acid of the disclosure which encodes a shmiR targeting a region of a PABPN1 mRNA transcript. Exemplary nucleic acids encoding shmiR16 are described herein and shall be taken to apply mutatis mutandis to this example of the disclosure. In one example, the ddRNAi construct comprises a nucleic acid which comprises or consists of a DNA sequence set forth in SEQ ID NO: 67 and which encodes a shmiR comprising or consisting of the sequence set forth in SEQ ID NO: 54, and at least one other nucleic acid of the disclosure which encodes a shmiR targeting a region of a PABPN1 mRNA transcript. For example, the ddRNAi construct may comprise (i) a nucleic acid comprising or consisting of a DNA sequence set forth in SEQ ID NO: 67 (shmiR16), and (ii) a nucleic acid comprising or consisting of a DNA sequence encoding one of shmiR2-shmiR7, shmiR9, shmiR11 or shmiR13-shmiR15, or shmiR17.

In one example, the ddRNAi construct comprises a nucleic acid comprising or consisting of a DNA sequence encoding shmiR17, and at least one other nucleic acid of the disclosure which encodes a shmiR targeting a region of a PABPN1 mRNA transcript. Exemplary nucleic acids encoding shmiR17 are described herein and shall be taken to apply mutatis mutandis to this example of the disclosure. In one example, the ddRNAi construct comprises a nucleic acid which comprises or consists of a DNA sequence set forth in SEQ ID NO: 68 and which encodes a shmiR comprising or consisting of the sequence set forth in SEQ ID NO: 55, and at least one other nucleic acid of the disclosure which encodes a shmiR targeting a region of a PABPN1 mRNA transcript. For example, the ddRNAi construct may comprise (i) a nucleic acid comprising or consisting of a DNA sequence set forth in SEQ ID NO: 68 (shmiR17), and (ii) a nucleic acid comprising or consisting of a DNA sequence encoding one of shmiR2-shmiR7, shmiR9, shmiR11 or shmiR13-shmiR16.

According to one example in which the ddRNAi construct encodes a plurality of shmiRs, at least one of the shmiRs comprises an effector sequence which is substantially complementary to a region of corresponding length in an RNA transcript comprising or consisting of the sequence set forth in SEQ ID NO: 1. Suitable nucleic acids encoding a shmiR having an effector sequence which is substantially complementary to a region of corresponding length in an RNA transcript comprising or consisting of the sequence set forth in SEQ ID NO: 1 are described herein e.g., for shmiR2.

According to one example in which the ddRNAi construct encodes a plurality of shmiRs, at least one of the shmiRs comprises an effector sequence which is substantially complementary to a region of corresponding length in an RNA transcript comprising or consisting of the sequence set forth in SEQ ID NO: 2. Suitable nucleic acids encoding a shmiR having an effector sequence which is substantially complementary to a region of corresponding length in an RNA transcript comprising or consisting of the sequence set forth in SEQ ID NO: 2 are described herein e.g., for shmiR3.

According to one example in which the ddRNAi construct encodes a plurality of shmiRs, at least one of the shmiRs comprises an effector sequence which is substantially complementary to a region of corresponding length in an RNA transcript comprising or consisting of the sequence set forth in SEQ ID NO: 4. Suitable nucleic acids encoding a shmiR having an effector sequence which is substantially complementary to a region of corresponding length in an RNA transcript comprising or consisting of the sequence set forth in SEQ ID NO: 4 are described herein e.g., for shmiR5.

According to one example in which the ddRNAi construct encodes a plurality of shmiRs, at least one of the shmiRs comprises an effector sequence which is substantially complementary to a region of corresponding length in an RNA transcript comprising or consisting of the sequence set forth in SEQ ID NO: 7. Suitable nucleic acids encoding a shmiR having an effector sequence which is substantially complementary to a region of corresponding length in an RNA transcript comprising or consisting of the sequence set forth in SEQ ID NO: 7 are described herein e.g., for shmiR9.

According to one example in which the ddRNAi construct encodes a plurality of shmiRs, at least one of the shmiRs comprises an effector sequence which is substantially complementary to a region of corresponding length in an RNA transcript comprising or consisting of the sequence set forth in SEQ ID NO: 9. Suitable nucleic acids encoding a shmiR having an effector sequence which is substantially complementary to a region of corresponding length in an RNA transcript comprising or consisting of the sequence set forth in SEQ ID NO: 9 are described herein e.g., for shmiR13.

According to one example in which the ddRNAi construct encodes a plurality of shmiRs, at least one of the shmiRs comprises an effector sequence which is substantially complementary to a region of corresponding length in an RNA transcript comprising or consisting of the sequence set forth in SEQ ID NO: 10. Suitable nucleic acids encoding a shmiR having an effector sequence which is substantially complementary to a region of corresponding length in an RNA transcript comprising or consisting of the sequence set forth in SEQ ID NO: 10 are described herein e.g., for shmiR14.

According to one example in which the ddRNAi construct encodes a plurality of shmiRs, at least one of the shmiRs comprises an effector sequence which is substantially complementary to a region of corresponding length in an RNA transcript comprising or consisting of the sequence set forth in SEQ ID NO: 13. Suitable nucleic acids encoding a shmiR having an effector sequence which is substantially complementary to a region of corresponding length in an RNA transcript comprising or consisting of the sequence set forth in SEQ ID NO: 13 are described herein e.g., for shmiR17.

An exemplary ddRNAi construct encoding a plurality of shmiRs of the disclosure comprises at least two nucleic acids, each comprising a DNA sequence encoding a shmiR of the disclosure, wherein each shmiR comprises a different effector sequence.

In one example, each of the at least two nucleic acids encode a shmiR comprising an effector sequence which is substantially complementary to a region of corresponding length in an RNA transcript set forth in one of SEQ ID NOs: 1, 2, 4, 7, 9, 10 and 13. Exemplary nucleic acids of the disclosure encoding shmiRs comprising effector sequences which are substantially complementary to regions of corresponding length in the RNA transcripts set forth in SEQ ID NO: 1, 2, 4, 7, 9, 10 and 13 are described herein and shall be taken to apply mutatis mutandis to this example of the disclosure.

In one example, the ddRNAi construct comprises at least two nucleic acids selected from the group consisting of:

- a nucleic acid comprising or consisting of a DNA sequence encoding a shmiR comprising an effector sequence set forth in SEQ ID NO: 15 and an effector complement sequence set forth in SEQ ID NO: 14 e.g., a nucleic acid comprising or consisting of a DNA sequence set forth in SEQ ID NO: 56 (shmiR2);
- a nucleic acid comprising or consisting of a DNA sequence encoding a shmiR comprising an effector sequence set forth in SEQ ID NO: 17 and an effector complement sequence set forth in SEQ ID NO: 16 e.g., a nucleic acid comprising or consisting of a DNA sequence set forth in SEQ ID NO: 57 (shmiR3);
- a nucleic acid comprising or consisting of a DNA sequence encoding a shmiR comprising an effector sequence set forth in SEQ ID NO: 21 and an effector complement sequence set forth in SEQ ID NO: 20 e.g., a nucleic acid comprising or consisting of a DNA sequence set forth in SEQ ID NO: 59 (shmiR5);
- a nucleic acid comprising or consisting of a DNA sequence encoding a shmiR comprising an effector sequence set forth in SEQ ID NO: 27 and an effector complement sequence set forth in SEQ ID NO: 26 e.g., a nucleic acid comprising or consisting of a DNA sequence set forth in SEQ ID NO: 62 (shmiR9);
- a nucleic acid comprising or consisting of a DNA sequence encoding a shmiR comprising an effector sequence set forth in SEQ ID NO: 31 and an effector complement sequence set forth in SEQ ID NO: 30 e.g., a nucleic acid comprising or consisting of a DNA sequence set forth in SEQ ID NO: 64 (shmiR13);
- a nucleic acid comprising or consisting of a DNA sequence encoding a shmiR comprising an effector sequence set forth in SEQ ID NO: 33 and an effector complement sequence set forth in SEQ ID NO: 32 e.g., a nucleic acid comprising or consisting of a DNA sequence set forth in SEQ ID NO: 65 (shmiR14); and
- a nucleic acid comprising or consisting of a DNA sequence encoding a shmiR comprising an effector sequence set forth in SEQ ID NO: 39 and an effector complement sequence set forth in SEQ ID NO: 38 e.g., a nucleic acid comprising or consisting of a DNA sequence set forth in SEQ ID NO: 68 (shmiR17).

In one example, each of the at least two nucleic acids within the ddRNAi construct encode a shmiR comprising an effector sequence which is substantially complementary to a region of corresponding length in an RNA transcript set forth in one of SEQ ID NOs: 2, 9, 10 and 13. Exemplary nucleic acids encoding shmiRs comprising effector sequences which are substantially complementary to regions of corresponding length in the RNA transcripts set forth in SEQ ID NO: 2, 9, 10 and 13 are described herein and shall be taken to apply mutatis mutandis to this example of the disclosure.

In one example, the ddRNAi construct comprises at least two nucleic acids selected from the group consisting of:

- a nucleic acid comprising or consisting of a DNA sequence encoding a shmiR comprising an effector sequence set forth in SEQ ID NO: 17 and an effector complement sequence set forth in SEQ ID NO: 16 e.g., a nucleic acid comprising or consisting of a DNA sequence set forth in SEQ ID NO: 57 (shmiR3);
- a nucleic acid comprising or consisting of a DNA sequence encoding a shmiR comprising an effector sequence set forth in SEQ ID NO: 31 and an effector complement sequence set forth in SEQ ID NO: 30 e.g., a nucleic acid comprising or consisting of a DNA sequence set forth in SEQ ID NO: 64 (shmiR13);
- a nucleic acid comprising or consisting of a DNA sequence encoding a shmiR comprising an effector sequence set forth in SEQ ID NO: 33 and an effector complement sequence set forth in SEQ ID NO: 32 e.g., a nucleic acid comprising or consisting of a DNA sequence set forth in SEQ ID NO: 65 (shmiR14); and
- a nucleic acid comprising or consisting of a DNA sequence encoding a shmiR comprising an effector sequence set forth in SEQ ID NO: 39 and an effector complement sequence set forth in SEQ ID NO: 38 e.g., a nucleic acid comprising or consisting of a DNA sequence set forth in SEQ ID NO: 68 (shmiR17).

In one example, the ddRNAi construct comprises a nucleic acid encoding a shmiR comprising an effector sequence which is substantially complementary to a region of corresponding length in an RNA transcript set forth in SEQ ID NO: 9, and a nucleic acid encoding a shmiR comprising an effector sequence which is substantially complementary to a region of corresponding length in an RNA transcript set forth in SEQ ID NO: 13. For example, the ddRNAi construct may comprise:

(a) a nucleic acid comprising or consisting of a DNA sequence encoding a shmiR comprising an effector sequence set forth in SEQ ID NO: 31 and an effector complement sequence set forth in SEQ ID NO: 30 e.g., a nucleic acid comprising or consisting of a DNA sequence set forth in SEQ ID NO: 64 (shmiR13); and (b) a nucleic acid comprising or consisting of a DNA sequence encoding a shmiR comprising an effector sequence set forth in SEQ ID NO: 39 and an effector complement sequence set forth in SEQ ID NO: 38 e.g., a nucleic acid comprising or consisting of a DNA sequence set forth in SEQ ID NO: 68 (shmiR17).

An exemplary ddRNAi construct of the disclosure comprises a nucleic acid comprising or consisting of a DNA sequence set forth in SEQ ID NO: 64 (shmiR13) and a nucleic acid comprising or consisting of a DNA sequence set forth in SEQ ID NO: 68 (shmiR17).

In one example, the ddRNAi construct comprises a nucleic acid encoding a shmiR comprising an effector sequence which is substantially complementary to a region of corresponding length in an RNA transcript set forth in SEQ ID NO: 2, and a nucleic acid encoding a shmiR comprising an effector sequence which is substantially complementary to a region of corresponding length in an RNA transcript set forth in SEQ ID NO: 10. For example, the ddRNAi construct may comprise:

(a) a nucleic acid comprising or consisting of a DNA sequence encoding a shmiR comprising an effector sequence set forth in SEQ ID NO: 17 and an effector complement sequence set forth in SEQ ID NO: 16, e.g., a nucleic acid comprising or consisting of a DNA sequence set forth in SEQ ID NO: 57 (shmiR3); and (b) a nucleic acid comprising or consisting of a DNA sequence encoding a shmiR comprising an effector sequence set forth in SEQ ID NO: 33 and an effector complement sequence set forth in SEQ ID NO: 32 e.g., a nucleic acid comprising or consisting of the sequence set forth in SEQ ID NO:65 (shmiR14).

An exemplary ddRNAi construct of the disclosure comprises a nucleic acid comprising or consisting of a DNA sequence set forth in SEQ ID NO: 57 (shmiR3) and a nucleic acid comprising or consisting of a DNA sequence set forth in SEQ ID NO: 65 (shmiR14).

In accordance with an example in which a the ddRNAi construct of the disclosure encodes two or more shmiRs, two or more of the nucleic acids encoding the shmiRs may form separate parts of the same polynucleotide within the ddRNAi construct.

In some examples, the or each nucleic acid encoding a shmiR may comprise, or be in operable linkage with, additional elements e.g., to facilitate transcription of the shmiR. For example, the ddRNAi construct may comprise one or more promoters operably linked to the sequence(s) encoding the shmiR(s) described herein. Other elements e.g., transcriptional terminators and initiators, are known in the art and/or described herein.

In each of the foregoing examples describing a ddRNAi construct of the disclosure, the or each nucleic acid encoding a shmiR may be operably linked to a promoter. For example, the ddRNAi construct as described herein may comprise a single promoter which is operably-linked to the or each nucleic acid encoding a shmiR comprised therein e.g., to drive expression of one or more shmiRs from the ddRNAi construct. In another example, each nucleic acid encoding a shmiR comprised in the ddRNAi construct is operably-linked to a separate promoter.

According to an example in which multiple promoters are present, the promoters can be the same or different. For example, the construct may comprise multiple copies of the same promoter with each copy operably linked to a different nucleic acid of the disclosure. In another example, each promoter operably linked to a nucleic acid encoding a shmiR of the disclosure is different. For example, in a ddRNAi construct encoding two shmiRs, the two nucleic acids encoding the shmiRs are each operably linked to a different promoter.

In one example, the promoter is a constitutive promoter. The term "constitutive" when made in reference to a promoter means that the promoter is capable of directing transcription of an operably linked nucleic acid sequence in the absence of a specific stimulus (e.g., heat shock, chemicals, light, etc.). Typically, constitutive promoters are capable of directing expression of a coding sequence in substantially any cell and any tissue. The promoters used to transcribe shmiRs include promoters for ubiquitin, CMV, β-actin, histone H4, EF-1α or pgk genes controlled by RNA polymerase II, or promoter elements controlled by RNA polymerase I.

In one example, a Pol II promoter such as CMV, SV40, U1, β-actin or a hybrid Pol II promoter is employed. Other suitable Pol II promoters are known in the art and may be used in accordance with this example of the disclosure. For example, a Pol II promoter system may be preferred in a ddRNAi construct of the disclosure which expresses a pri-miRNA which, by the action of the enzymes Drosha and Pasha, is processed into one or more shmiRs. A Pol II promoter system may also be preferred in a ddRNAi construct of the disclosure comprising sequence encoding a plurality of shmiRs under control of a single promoter. A Pol II promoter system may also be preferred where tissue specificity is desired.

In another example, a promoter controlled by RNA polymerase III is used, such as a U6 promoter (U6-1, U6-8, U6-9), H1 promoter, 7SL promoter, a human Y promoter (hY1, hY3, hY4 (see Maraia, et al., *Nucleic Acids Res* 22(15):3045-52(1994)) and hY5 (see Maraia, et al., *Nucleic Acids Res* 24(18):3552-59(1994)), a human MRP-7-2 promoter, an Adenovirus VA1 promoter, a human tRNA promoter, or a 5s ribosomal RNA promoter.

Suitable promoters for use in a ddRNAi construct of the disclosure are described in U.S. Pat. Nos. 8,008,468 and 8,129,510.

In one example, the promoter is a RNA pol III promoter. For example, the promoter is a U6 promoter (e.g., a U6-1, U6-8 or U6-9 promoter). In another example, the promoter is a H1 promoter.

In the case of a ddRNAi construct of the disclosure encoding a plurality of shmiRs, each of the nucleic acids in the ddRNAi construct may be operably linked to a U6 promoter e.g., a separate U6 promoter.

In one example, the promoter in a ddRNAi construct is a U6 promoter. For example, the promoter may be a U6-1 promoter. For example, the promoter may be a U6-8 promoter. For example, the promoter may be a U6-9 promoter.

In some examples, promoters of variable strength are employed. For example, use of two or more strong promoters (such as a Pol III-type promoter) may tax the cell, by, e.g., depleting the pool of available nucleotides or other cellular components needed for transcription. In addition, or alternatively, use of several strong promoters may cause a toxic level of expression of shmiRs in the cell. Thus, in some examples one or more of the promoters in a multiple-promoter ddRNAi construct may be weaker than other promoters in the construct, or all promoters in the construct may express the shmiRs at less than a maximum rate. Promoters may also be modified using various molecular techniques, or otherwise, e.g., through modification of various regulatory elements, to attain weaker levels or stronger levels of transcription. One means of achieving reduced transcription is to modify sequence elements within promoters known to control promoter activity. For example the Proximal Sequence Element (PSE) is known to effect the activity of human U6 promoters (see Domitrovich, et al., *Nucleic Acids Res* 31: 2344-2352 (2003). Replacing the PSE elements present in strong promoters, such as the human U6-1, U6-8 or U6-9 promoters, with the element from a weak promoter, such as the human U6-7 promoter, reduces the activity of the hybrid U6-1, U6-8 or U6-9 promoters. This approach has been used in the examples described in this application, but other means to achieve this outcome are known in the art.

Promoters useful in the ddRNAi construct of the present disclosure can also be tissue-specific or cell-specific. The term "tissue specific" as it applies to a promoter refers to a promoter that is capable of directing selective transcription of a nucleic acid of interest to a specific type of tissue (e.g., tissue of the eye or muscle) in the relative absence of expression of the same nucleotide sequence of interest in a different type of tissue (e.g., liver). The term "cell-specific" as applied to a promoter refers to a promoter which is capable of directing selective transcription of a nucleic acid of interest in a specific type of cell in the relative absence of expression of the same nucleotide sequence of interest in a different type of cell within the same tissue. According to one example, a muscle-specific promoter is used, such as Spc512 or CK8. However, other muscle-specific promoters are known in the art and are contemplated for use in conjunction with a ddRNAi construct of the disclosure.

In one example, a ddRNAi construct of the disclosure may additionally comprise one or more enhancers to increase expression of the shmiRs described herein. Enhancers appropriate for use in examples of the present disclosure include the Apo E HCR enhancer, a CMV enhancer (Xia et al, *Nucleic Acids Res* 31-17(2003)), and other enhancers known to those skilled in the art. Suitable enhancers for use in a ddRNAi construct of the disclosure are described in U.S. Pat. No. 8,008,468.

In a further example, a ddRNAi construct of the disclosure may comprise a transcriptional terminator linked to a nucleic acid encoding a shmiR of the disclosure. In the case of a ddRNAi construct comprising a plurality of nucleic acids described herein i.e., encoding multiple shmiRs, the terminators linked to each nucleic acid can be the same or different. For example, in a ddRNAi construct of the disclosure in which a RNA pol III promoter is employed, the terminator may be a contiguous stretch of 4 or more or 5 or more or 6 or more T residues. However, where different promoters are used, the terminators can be different and are matched to the promoter from the gene from which the terminator is derived. Such terminators include, but are not limited to, the SV40 poly A, the AdV VA1 gene, the 5S ribosomal RNA gene, and the terminators for human t-RNAs. Other promoter and terminator combinations are known in the art and are contemplated for use in a ddRNAi construct of the disclosure.

In addition, promoters and terminators may be mixed and matched, as is commonly done with RNA pol II promoters and terminators.

In one example, the promoter and terminator combinations used for each nucleic acid in a ddRNAi construct comprising a plurality of nucleic acids is different to decrease the likelihood of DNA recombination events between components.

One exemplary ddRNAi construct of the disclosure comprises a nucleic acid comprising or consisting of a DNA sequence encoding shmiR13 as described herein operably linked to a promoter, and a nucleic acid comprising or consisting of a DNA sequence encoding shmiR17 as described herein operably linked to a promoter. For example, an exemplary ddRNAi construct of the disclosure comprises a nucleic acid comprising or consisting of a DNA sequence set forth in SEQ ID NO: 64 operably linked to a promoter, and a nucleic acid comprising or consisting of a DNA sequence set forth in SEQ ID NO: 68 operably linked to a promoter. In one example, each nucleic acid in the ddRNAi construct encoding a shmiR is operably linked to a separate promoter. In another example, each nucleic acid in the ddRNAi construct encoding a shmiR is operably linked to the same promoter. For example, the or each promoter may be a U6 promoter e.g., a U6-1, U6-8 or U6-9 promoter. For example, the or each promoter may be a muscle specific promoter e.g., a Spc512 or CK8 promoter.

In accordance with one example in which the nucleic acids in the ddRNAi construct encoding shmiR13 and shmiR17 are operably-linked to the same Spc512 promoter, the ddRNAi construct comprises or consists of the DNA sequence set forth in SEQ ID NO: 72. In accordance with an example in which the nucleic acids in the ddRNAi construct encoding shmiR13 and shmiR17 are operably-linked to the same CK8 promoter, the ddRNAi construct comprises or consists of the DNA sequence set forth in SEQ ID NO: 70.

Another exemplary ddRNAi construct of the disclosure comprises a nucleic acid comprising or consisting of a DNA sequence encoding shmiR3 as described herein operably linked to a promoter, and a nucleic acid comprising or consisting of a DNA sequence encoding shmiR14 as described herein operably linked to a promoter. For example, an exemplary ddRNAi construct of the disclosure comprises a nucleic acid comprising or consisting of a DNA sequence set forth in SEQ ID NO: 57 operably linked to a promoter, and a nucleic acid comprising or consisting of a DNA sequence set forth in SEQ ID NO: 65 operably linked to a promoter. In one example, each nucleic acid in the ddRNAi construct encoding a shmiR is operably linked to a separate promoter. In another example, each nucleic acid in the ddRNAi construct encoding a shmiR is operably linked to the same promoter. For example, the or each promoter may be a U6 promoter e.g., a U6-1, U6-8 or U6-9 promoter. For example, the or each promoter may be a muscle specific promoter e.g., a Spc512 or CK8 promoter.

In accordance with an example in which the nucleic acids in the ddRNAi construct encoding shmiR3 and shmiR14 are operably-linked to the same Spc512 promoter, the ddRNAi construct comprises or consists of the DNA sequence set forth in SEQ ID NO: 71. In accordance with an example in which the nucleic acids in the ddRNAi construct encoding shmiR3 and shmiR14 are operably-linked to the same CK8 promoter, the ddRNAi construct comprises or consists of the DNA sequence set forth in SEQ ID NO: 69.

In addition, the ddRNAi construct can comprise one or more multiple cloning sites and/or unique restriction sites that are located strategically, such that the promoter, nucleic acid encoding the shmiR and/or other regulator elements are easily removed or replaced. The ddRNAi construct can be assembled from smaller oligonucleotide components using strategically located restriction sites and/or complementary sticky ends. The base vector for one approach according to the present disclosure comprises plasmids with a multilinker in which all sites are unique (though this is not an absolute requirement). Sequentially, each promoter is inserted between its designated unique sites resulting in a base cassette with one or more promoters, all of which can have variable orientation. Sequentially, again, annealed primer pairs are inserted into the unique sites downstream of each of the individual promoters, resulting in a single-, double- or multiple-expression cassette construct. The insert can be moved into an AAV backbone using two unique restriction enzyme sites (the same or different ones) that flank the single-, double- or multiple-expression cassette insert.

Generation of the ddRNAi construct can be accomplished using any suitable genetic engineering techniques known in the art, including without limitation, the standard techniques of PCR, oligonucleotide synthesis, restriction endonuclease digestion, ligation, transformation, plasmid purification, and DNA sequencing. The ddRNAi construct (or polynucleotide comprising same) may also comprise sequences necessary to package the ddRNAi construct into viral particles and/or sequences that allow integration of the ddRNAi construct into the target cell genome. In some examples, the or each viral construct additionally contains genes that allow for replication and propagation of virus, however such genes will be supplied in trans. Additionally, the or each viral construct cam contain genes or genetic sequences from the genome of any known organism incorporated in native form or modified. For example, a viral construct may comprise sequences useful for replication of the construct in bacteria.

Testing a shmiR or ddRNAi Construct of the Disclosure

Cell Culture Models

An example of cell line useful as a cell culture model for OPMD is the HEK293T cell line (HEK293T, ATCC, Manassas, USA) which has been transfected with a vector expressing normal Ala10-humanPABPN1-FLAG (Ala10) or mutant Ala17-humanPABPN1-FLAG (Ala17), the latter being hallmark of OPMD.

Further examples of cell lines useful as cell culture models for OPMD are the C2C12 mouse muscle cell and the ARPE-19 human retinal cells.

Another example of a cell line useful as a cell culture model for OPMD is the primary mouse myoblast (IM2) cell line stably transfected to express either normal Ala10-humanPABPN1-FLAG (Ala10) or mutant Ala17-human-PABPN1-FLAG (Ala17). An exemplary IM2 derived cell line which stably expresses mutant Ala17-humanPABPN1-FLAG (Ala17) is the H2 kB-D7e cell line. The H2 kB-D7e cell line is also described in Raz et al., (2011) *American Journal of Pathology,* 179(4):1988-2000.

Other cell lines suitable for cell culture models of OPMD are known in the art, such as described in Fan et al., (2001) *Human Molecular Genetics,* 10:2341-2351, Bao et al., (2002) *The Journal of Biological Chemistry,* 277:12263-12269, and Abu-Baker et al., (2003) *Human Molecular Genetics,* 12:2609-2623.

As exemplified herein, activity of a shmiR of the disclosure is determined by administering a nucleic acid encoding the shmiR, or a ddRNAi construct or expression vector comprising same, to the cell and subsequently measuring the level of expression of a RNA or protein encoded by the PABPN1 gene. For example, intracellular PABPN1 gene expression can be assayed by any one or more of RT-PCR, quantitative PCR, semi-quantitative PCR, or in-situ hybridization under stringent conditions, using one or more probes or primers which are specific for PABPN1. PABPN1 mRNA or DNA can also be assayed either by PCR using one or more probes or primers which are specific for PABPN1, Western blots or ELISA can be used to detect PABPN1 protein.

Polynucleotides which may be used in RT-PCR, quantitative PCR or semi-quantitative PCR techniques for detecting PABPN1 expression are known and commercially available (Thermo Fisher). However, polynucleotides useful for PCR-based detection methods can be designed based on sequence information available for PABPN1 using method and/or software known in the art. In one example, the presence or absence of PABPN1 mRNA may be detected using RT-PCR using standard methodologies known in the art. In one example, the presence or absence or relative amount of PABPN1 polypeptide or protein may be detected using any one or more of Western blotting, ELISA, or other standard quantitative or semiquantitative techniques available in the art, or a combination of such techniques. Techniques relying on antibody recognition of PABPN1 are contemplated and are described herein. In one example, the presence or absence or relative abundance of PABPN1 polypeptide may be detected with techniques which comprise antibody capture of PABPN1 polypeptides in combination with electrophoretic resolution of captured PABPN1 polypeptides, for example using the Isonostic™ Assay (Target Discovery, Inc.). Antibodies are commercially available for PABPN1 protein.

Various means for normalizing differences in transfection or transduction efficiency and sample recovery are known in the art.

A nucleic acid, ddRNAi construct or expression vector of the disclosure that reduces expression of a mRNA or protein encoded by PABPN1 or that reduces the presence of nuclear aggregates of PABPN1 protein, relative to a level of mRNA expression or protein encoded by PABPN1 or an amount of nuclear aggregates of PABPN1 protein in the absence of the RNA of the disclosure, is considered to be useful for therapeutic applications e.g., such as treating OPMD by reducing expression of endogenous PABPN1 and replacing some or all of the endogenous PABPN1 with a PABPN1 protein which is not causative of OPMD as described herein.

Animal Models

There are several small animal models available for studying OPMD, examples of which are described in Uyama et al., (2005) *Acta Myologica,* 24(2):84-88 and Chartier and Simonelig (2013) *Drug Discovery Today: technologies,* 10:e103-107. An exemplary animal model is the A17.1 transgenic mouse model which has been described previously in Davies et al., (2005) Nature Medicine, 11:672-677 and Trollet et al., (2010) *Human Molecular Genetics,* 19(11):2191-2207.

Any of the foregoing animal models can be used to determine the efficacy of a shmiR or ddRNAi construct of the disclosure to knockdown, reduce or inhibit expression of a RNA or protein encoded by the PABPN1 gene.

Methods for assaying PABPN1 gene expression have been described herein with respect to cell models and shall be taken to apply mutatis mutandis to this example of the disclosure.

PABPN1 Constructs

As described herein, the AAV of the disclosure comprises a polynucleotide sequence comprising a PABPN1 construct. In this regard, the AAV of the present disclosure provides an agent for replacement of functional PABPN1 protein e.g., to a cell or animal. The functional PABPN1 protein will not be causative of OPMD, nor will it be encoded by a mRNA transcript which is targeted by the shmiR(s) encoded by the ddRNAi construct as described herein which is also comprised within the AAV.

In one example, the PABPN1 construct comprises a nucleic acid e.g., such as DNA or cDNA, encoding the functional PABPN1 protein. For example, the nucleic acid encoding the functional PABPN1 protein may be codon optimised e.g., contain one or more degenerate or wobble bases relative to the wild type PABPN1 nucleic acid but which encodes for identical amino acids, so that the corresponding mRNA sequence coding for the functional PABPN1 protein is not recognised by the shmiR(s) encoded and expressed from the ddRNAi construct. For example, a codon optimised nucleic acid encoding the functional PABPN1 protein may comprise one or more degenerate or wobble bases relative to the wild type PABPN1 nucleic acid within the region targeted by the one or more shmiR encoded and expressed from the ddRNAi construct. In one example, the one or more degenerate or wobble bases resides within a seed region of an effector sequence of a shmiR encoded and expressed from the ddRNAi construct.

In one example, a nucleic acid with the PABPN1 construct encoding the functional PABPN1 protein is codon optimised such that its corresponding mRNA sequence is not recognised by the shmiR(s) encoded and expressed from the ddRNAi construct. Preferably, the functional PABPN1 protein encoded by the codon optimised nucleic acid sequence comprises the amino acid sequence set forth in SEQ ID NO: 74 i.e., the amino acid sequence of the wild-type human PABPN1 protein. A skilled person will appreciate that there are a number of nucleotide sequence combinations which may be used to encode functional PABPN1 protein, and the choice of nucleotide sequence will ultimately depend on the effector sequence of the shmiR(s) encoded and expressed from the ddRNAi construct i.e., such that the codon-optimised nucleic acid is not recognised by the shmiR(s). In one example, the PABPN1 construct comprises a nucleic acid comprising the sequence set forth in SEQ ID NO: 73. In one example, the nucleic acid encoding the functional PABPN1 protein may also comprise a Kozak sequence.

In one example, the codon-optimised nucleic acid encoding the functional PABPN1 protein is operably-linked to a promoter suitable for expression of the functional PABPN1 protein. Promoters suitable for expression of the functional PABPN1 protein muscle may be particularly suitable. One exemplary promoter suitable for use with the nucleic acid encoding the functional PABPN1 protein is a Spc512 promoter. Another exemplary promoter suitable for use with the nucleic acid encoding the functional PABPN1 protein is a CK8 promoter. However, any suitable promoter known in the art may be used. For example, other suitable promoters for use with the nucleic acid encoding the functional PABPN1 protein are described in US 20110212529 A1.

In one example, the PABPN1 construct and the ddRNAi construct are operably linked to the same promoter within the same polynucleotide e.g., they are both operably linked to a Spc512 promoter. In accordance with this example, a single promoter drives expression of the functional PABPN1 protein and the shmiRs.

As described herein, promoters useful in some examples of the present disclosure can be tissue-specific or cell-specific.

In one example, a codon-optimised nucleic acid encoding the functional PABPN1 protein of the disclosure may additionally comprise one or more enhancers to increase expression of the functional PABPN1 protein and its corresponding mRNA transcript. Enhancers appropriate for use in this example of the present disclosure will be known to those skilled in the art.

Testing for Functional PABPN1

Animal Models

Exemplary animal models for studying OPMD have been described.

Any of the foregoing animal models can be used to determine the efficacy of the PABPN1 construct, or AAV comprising same, to replace functional PABPN1 protein in vivo in the presence of one or more shmiR(s) expressed from the ddRNAi of the disclosure.

Methods for assaying PABPN1 expression have been described herein with respect to cell models and shall be taken to apply mutatis mutandis to this example of the disclosure.

In one example, histological and morphological analyses may be used to determine the efficacy of an agent of the disclosure to replace functional PABPN1 protein in vivo in the presence one or more shmiR(s) expressed from the ddRNAi of the disclosure. Further assays which may be used to determine efficacy of an agent of the disclosure to replace functional PABPN1 protein in vivo are described in Trollet et al., (2010) *Human Molecular Genetics,* 19(11): 2191-2207.

PABPN1 'Silence and Replace' DNA Constructs

As described herein, the AAV of the disclosure comprises a single polynucleotide comprising a ddRNAi construct and PABPN1 construct as described herein. That is, the ddRNAi construct and the PABPN1 construct may be provided as a combined DNA construct (also referred to herein as a 'silence and replace' construct or SR construct), which is packaged in a modified AAV as described herein for delivery to a patient. An exemplary DNA construct comprising a nucleic acid encoding the functional PABPN1 protein and the ddRNAi construct of the disclosure is described in Example 2.

The single DNA construct comprising the ddRNAi construct and PABPN1 construct may comprise one or more promoters e.g., to drive expression of the functional PABPN1 protein and/or shmiRs encoded by the ddRNAi construct. Promoters useful in some examples of the present disclosure can be tissue-specific or cell-specific. Exemplary promoters muscle-specific promoter, such as for example, Spc512 and CK8. However, any suitable promoter known in the art is contemplated for use in the DNA construct described herein e.g., such as those described in US 20110212529 A1.

The DNA construct comprising the ddRNAi construct and PABPN1 construct is packaged in a modified AAV as described herein for delivery to a patient.

In one example, the DNA construct comprises, in a 5' to 3' direction, a muscle-specific promoter e.g., a Spc512 promoter, a PABPN1 construct described herein and a ddRNAi construct as described herein e.g., wherein the ddRNAi construct is positioned in the 3' untranslated region (UTR) of nucleic acid encoding the functional PABPN1 protein. A DNA construct in accordance with this example is illustrated in FIG. 1A.

An exemplary DNA construct in accordance with this example comprises, in a 5' to 3' direction:

(a) a muscle-specific promoter e.g., Spc512;

(b) a PABPN1 construct as described herein comprising a DNA sequence encoding a functional PABPN1 protein having a mRNA transcript which is not targeted by the shmiRs encoded by the ddRNAi construct; and (c) a ddRNAi construct of the disclosure comprising a nucleic acid comprising a DNA sequence encoding shmiR17 as described herein and a nucleic acid comprising a DNA sequence encoding shmiR13 as described herein.

In accordance with this example, the DNA construct may comprise or consist of the DNA sequence set forth in SEQ ID NO: 72.

An exemplary ddRNAi construct encoding shmiR13 and shmiR17 for inclusion in a DNA construct of the disclosure comprises a nucleic acid comprising or consisting of a DNA sequence encoding a shmiR comprising an effector sequence set forth in SEQ ID NO: 31 and an effector complement sequence which is substantially complementary to the sequence set forth in SEQ ID NO: 31 e.g., an effector complement sequence set forth in SEQ ID NO: 30 (shmiR13), and a nucleic acid comprising or consisting of a DNA sequence encoding a shmiR comprising an effector sequence set forth in SEQ ID NO: 39 and an effector complement sequence which is substantially complementary to the sequence set forth in SEQ ID NO: 39 e.g., an effector complement sequence set forth in SEQ ID NO: 38 (shmiR17). For example, the ddRNAi construct in accordance with this example of the DNA construct may comprise a nucleic acid comprising or consisting of the DNA sequence set forth in SEQ ID NO: 64 (shmiR13), and a nucleic acid comprising or consisting of the DNA sequence set forth in SEQ ID NO: 68 (shmiR17).

An exemplary PABPN1 construct for inclusion in a DNA construct of the disclosure comprises a codon-optimised sequence set forth in SEQ ID NO: 73 and encodes a functional PABPN1 protein set forth in SEQ ID NO: 74.

Whilst certain examples have been described, it will be appreciated that a DNA construct in accordance with the present disclosure may include any ddRNAi construct described herein encoding one or more shmiRs targeting the RNA transcript of PABPN1. However, ddRNAi constructs encoding shmiRs described in Examples 1 to 5 herein may be particularly suitable for inclusion in a DNA construct of the disclosure. Similarly, it will be appreciated that a DNA construct in accordance with the present disclosure may include any PABPN1 construct encoding a functional PABPN1 protein, the transcript of which is not targeted by the shmiRs expressed from the ddRNAi construct.

Compositions and Carriers

In some examples, the AAV of the disclosure may be provided in a pharmaceutical composition which is formulated for delivery to a patient e.g., a human patient.

A composition of the disclosure may also comprise one or more pharmaceutically acceptable carriers or diluents. For example, the composition may comprise a carrier suitable for delivery of the AAVs of the disclosure to muscle of a subject following administration thereto. Carriers suitable for formulation and delivery of AAVs are known in the art and contemplated herein.

Compositions will desirably include materials that increase the biological stability of the AAVs of the disclosure and/or materials that increase the ability of the AAVs to localise to and/or penetrate muscle cells selectively. The therapeutic compositions of the disclosure may be administered in pharmaceutically acceptable carriers (e.g., physiological saline), which are selected on the basis of the mode and route of administration, and standard pharmaceutical practice. One having ordinary skill in the art can readily formulate a pharmaceutical composition that comprises one or more AAVs of the disclosure. In some cases, an isotonic formulation is used. Generally, additives for isotonicity can include sodium chloride, dextrose, mannitol, sorbitol and lactose. In some cases, isotonic solutions such as phosphate buffered saline are preferred. Stabilizers include gelatin and albumin. In some examples, a vasoconstriction agent is added to the formulation. The compositions according to the present disclosure are provided sterile and pyrogen free. Suitable pharmaceutical carriers, as well as pharmaceutical necessities for use in pharmaceutical formulations, are described in Remington: The Science and Practice of Pharmacy (formerly Remington's Pharmaceutical Sciences), Mack Publishing Co., a standard reference text in this field, and in the USP/NF.

The volume, concentration, and formulation of the pharmaceutical composition, as well as the dosage regimen may be tailored specifically to maximize cellular delivery while minimizing toxicity such as an inflammatory response e.g., relatively large volumes (5, 10, 20, 50 ml or more) with corresponding low concentrations of active ingredients, as well as the inclusion of an anti-inflammatory compound such as a corticosteroid, may be utilized if desired.

Compositions of the disclosure may be formulated for administration by any suitable route (e.g., suitable for delivery to the pharyngeal muscle of a subject). For example, routes of administration include, but are not limited to, intramuscular, intraperitoneal, intradermal, subcutaneous, intravenous, intraarterially, intraocularly and oral as well as transdermal or by inhalation or suppository. Exemplary routes of administration include intravenous (IV), intramuscular (IM), oral, intraperitoneal, intradermal, intraarterial and subcutaneous injection. In one example, the composition of the disclosure is formulated for IM administration (e.g., formulated for administration to the pharyngeal muscle). In a preferred embodiment, the administration is directly to the pharyngeal muscle of a subject. For example, the pharyngeal muscle may comprise one or more of an inferior constrictor muscle, a middle constrictor muscle, a superior constrictor muscle, a palatopharyngeus muscle, a salpingopharyngeus muscle, a stylopharyngeus muscle, or any combination thereof. In another preferred embodiment, the administration is directly to a muscle of the tongue in a subject. Such compositions are useful for pharmaceutical applications and may readily be formulated in a suitable sterile, non-pyrogenic vehicle, e.g., buffered saline for injection, for parenteral administration e.g., IM (e.g., directly to the pharyngeal muscle), intravenously (including intravenous infusion), SC, and for intraperitoneal administration. In a preferred embodiment, the route of administration, such as IM (e.g., directly to the pharyngeal muscle) achieves effective delivery to muscle tissue and transduction of a ddRNAi constructs and codon-optimised nucleic acids encoding PABPN1 of the disclosure, and expression of shmiRs and the codon-optimised nucleic acid therein.

Methods of Treatment

Certain aspects of the disclosure are directed to administering to a human subject in need thereof an AAV or composition comprising same as described herein for treating the subject and/or inhibiting expression of endogenous PABPN1 protein, including a PABPN1 protein which is causative of OPMD, in the subject, wherein the composition is administered by direct injection to a pharyngeal muscle of the subject.

In some embodiments, the AAV or composition comprising same as described herein may be used to treat OPMD in a subject suffering therefrom. Similarly, the AAV or composition comprising same as described herein may be used to prevent the development or progression of one or more symptoms of OPMD in a subject suffering therefrom or predisposed thereto.

In some embodiments, the subject has improved swallowing following administering the AAV or composition comprising same as described herein by direct injection to a pharyngeal muscle of the subject.

As described herein, the AAV and/or composition of the disclosure comprise both a ddRNAi construct of the disclosure and a PABPN1 construct of the disclosure comprising codon-optimised nucleic acid encoding functional PABPN1 protein of the disclosure. Accordingly, administration of the AAV or composition may be effective to (i) inhibit, reduce or knockdown expression of endogenous PABPN1, including the PABPN1 protein comprising an expanded polyalanine tract which is causative of OPMD, and (ii) provide for expression of a functional PABPN1 protein which is not targeted by shmiRs which inhibit, reduce or knockdown expression of endogenous PABPN1. An AAV or composition of the disclosure may thus restore PABPN1 protein function, e.g., post-transcriptional processing of RNA, in a cell or animal to which it is administered.

In certain embodiments, treatment of OPMD may comprise administering by direct injection to a pharyngeal muscle of a subject an AAV or composition comprising same as described herein In some embodiments, the route of administration is IM (e.g., direct injection to a pharyngeal muscle of the subject) and achieves effective delivery to muscle tissue and transduction of a ddRNAi construct and PABPN1 construct of the disclosure comprising codon-optimised nucleic acids encoding PABPN1, and expression of shmiRs targeting the wild-type PABPN1 mRNA transcript and expression of the codon-optimised nucleic acid therein.

The therapeutically effective dose level for any particular patient will depend upon a variety of factors including: the composition employed; the age, body weight, general health, sex and diet of the patient; the time of administration; the route of administration; the rate of sequestration of the AAV or composition comprising same as described herein, the duration of the treatment, together with other related factors.

Efficacy of an AAV or composition comprising same of the disclosure to reduce or inhibit expression of the PABPN1 protein causative of OPMD and to express functional PABPN1 protein which is not causative of OPMD in an amount sufficient to restore PABPN1 function, may be determined by evaluating muscle contractile properties and/or swallowing difficulties in the subject treated. Methods for testing swallowing ability and muscle contractile properties are known in the art. For example, swallowing difficulties may be evaluated using videofluoroscopy, UGI endoscopy or oesophageal manometry and impedance testing. Other methods for assessing clinical features of OPMD are described in Rüegg et al., (2005) Swiss Medical Weekly, 135:574-586.

TABLE 1

Targeted regions in PABPN1

| Region ID | Region sequence (5'-3') | SEQ ID NO: |
|---|---|---|
| Region 2 | GAGAAGCAGAUGAAUAUGAGUCCACCUC | SEQ ID NO: 1 |
| Region 3 | GAACGAGGUAGAGAAGCAGAUGAAUAUG | SEQ ID NO: 2 |
| Region 4 | GAAGCUGAGAAGCUAAAGGAGCUACAGA | SEQ ID NO: 3 |
| Region 5 | GGGCUAGAGCGACAUCAUGGUAUUCCCC | SEQ ID NO: 4 |
| Region 6 | CUGUGUGACAAAUUUAGUGGCCAUCCCA | SEQ ID NO: 5 |
| Region 7 | GACUAUGGUGCAACAGCAGAAGAGCUGG | SEQ ID NO: 6 |
| Region 9 | CGAGGUAGAGAAGCAGAUGAAUAUGAGU | SEQ ID NO: 7 |
| Region 11 | CAGUGGUUUUAACAGCAGGCCCCGGGGU | SEQ ID NO: 8 |
| Region 13 | AGAGCGACAUCAUGGUAUUCCCCUUACU | SEQ ID NO: 9 |
| Region 14 | GGUAGAGAAGCAGAUGAAUAUGAGUCCA | SEQ ID NO: 10 |
| Region 15 | AUUGAGGAGAAGAUGGAGGCUGAUGCCC | SEQ ID NO: 11 |
| Region 16 | GGAGGAAGAAGCUGAGAAGCUAAAGGAG | SEQ ID NO: 12 |
| Region 17 | AACGAGGUAGAGAAGCAGAUGAAUAUGA | SEQ ID NO: 13 |

TABLE 2 shmiR effector and effector complement sequences

| shmiR ID | Effector complement sequence (5'-3') | SEQ ID NO: | Effector sequence (5'-3') | SEQ ID NO: |
|---|---|---|---|---|
| shmiR2 | AGCAGAUGAAUAUGAGUCCA | SEQ ID NO: 14 | UGGACUCAUAUUCAUCUGCUU | SEQ ID NO: 15 |
| shmiR3 | GAGGUAGAGAAGCAGAUGAA | SEQ ID NO: 16 | UUCAUCUGCUUCUCUACCUCG | SEQ ID NO: 17 |
| shmiR4 | CUGAGAAGCUAAAGGAGCUA | SEQ ID NO: 18 | UAGCUCCUUUAGCUUCUCAGC | SEQ ID NO: 19 |
| shmiR5 | UAGAGCGACAUCAUGGUAUU | SEQ ID NO: 20 | AAUACCAUGAUGUCGCUCUAG | SEQ ID NO: 21 |
| shmiR6 | GUGACAAAUUUAGUGGCCAU | SEQ ID NO: 22 | AUGGCCACUAAAUUUGUCACA | SEQ ID NO: 23 |
| shmiR7 | AUGGUGCAACAGCAGAAGAG | SEQ ID NO: 24 | CUCUUCUGCUGUUGCACCAUA | SEQ ID NO: 25 |
| shmiR9 | GUAGAGAAGCAGAUGAAUAU | SEQ ID NO: 26 | AUAUUCAUCUGCUUCUCUACC | SEQ ID NO: 27 |

TABLE 2-continued shmiR effector and effector complement sequences

| shmiR ID | Effector complement sequence (5'-3') | SEQ ID NO: | Effector sequence (5'-3') | SEQ ID NO: |
|---|---|---|---|---|
| shmiR11 | GGUUUUAACAGCAGGCCCCG | SEQ ID NO: 28 | CGGGGCCUGCUGUUAAAACCA | SEQ ID NO: 29 |
| shmiR13 | CGACAUCAUGGUAUUCCCCU | SEQ ID NO: 30 | AGGGGAAUACCAUGAUGUCGC | SEQ ID NO: 31 |
| shmiR14 | GAGAAGCAGAUGAAUAUGAG | SEQ ID NO: 32 | CUCAUAUUCAUCUGCUUCUCU | SEQ ID NO: 33 |
| shmiR15 | AGGAGAAGAUGGAGGCUGAU | SEQ ID NO: 34 | AUCAGCCUCCAUCUUCUCCUC | SEQ ID NO: 35 |
| shmiR16 | GAAGAAGCUGAGAAGCUAAA | SEQ ID NO: 36 | UUUAGCUUCUCAGCUUCUUCC | SEQ ID NO: 37 |
| shmiR17 | AGGUAGAGAAGCAGAUGAAU | SEQ ID NO: 38 | AUUCAUCUGCUUCUCUACCUC | SEQ ID NO: 39 |

TABLE 3 shmiR sequences

| shmiR | shmiR sequences (5'-3') | SEQ ID NO: |
|---|---|---|
| shmiR2 | GGUAUAUUGCUGUUGACAGUGAGCGUA<br>GCAGAUGAAUAUGAGUCCAACUGUGAA<br>GCAGAUGGGUUGGACUCAUAUUCAUCU<br>GCUUCGCCUACUGCCUCGGACUUCAA | SEQ ID NO: 43 |
| shmiR3 | GGUAUAUUGCUGUUGACAGUGAGCGAG<br>AGGUAGAGAAGCAGAUGAAACUGUGAA<br>GCAGAUGGGUUUCAUCUGCUUCUCUAC<br>CUCGCGCCUACUGCCUCGGACUUCAA | SEQ ID NO: 44 |
| shmiR4 | GGUAUAUUGCUGUUGACAGUGAGCGAC<br>UGAGAAGCUAAAGGAGCUAACUGUGAA<br>GCAGAUGGGUUAGCUCCUUUAGCUUCU<br>CAGCCGCCUACUGCCUCGGACUUCAA | SEQ ID NO: 45 |
| shmiR5 | GGUAUAUUGCUGUUGACAGUGAGCGAU<br>AGAGCGACAUCAUGGUAUUACUGUGAA<br>GCAGAUGGGUAAUACCAUGAUGUCGCU<br>CUAGCGCCUACUGCCUCGGACUUCAA | SEQ ID NO: 46 |
| shmiR6 | GGUAUAUUGCUGUUGACAGUGAGCGAG<br>UGACAAAUUUAGUGGCCAUACUGUGAA<br>GCAGAUGGGUAUGGCCACUAAAUUUGU<br>CACACGCCUACUGCCUCGGACUUCAA | SEQ ID NO: 47 |
| shmiR7 | GGUAUAUUGCUGUUGACAGUGAGCGAA<br>UGGUGCAACAGCAGAAGAGACUGUGAA<br>GCAGAUGGGUCUCUUCUGCUGUUGCAC<br>CAUACGCCUACUGCCUCGGACUUCAA | SEQ ID NO: 48 |
| shmiR9 | GGUAUAUUGCUGUUGACAGUGAGCGAG<br>UAGAGAAGCAGAUGAAUAUACUGUGAA<br>GCAGAUGGGUAUAUUCAUCUGCUUCUC<br>UACCCGCCUACUGCCUCGGACUUCAA | SEQ ID NO: 49 |
| shmiR11 | GGUAUAUUGCUGUUGACAGUGAGCGAG<br>GUUUUAACAGCAGGCCCCGACUGUGAA<br>GCAGAUGGGUCGGGGCCUGCUGUUAAA<br>ACCACGCCUACUGCCUCGGACUUCAA | SEQ ID NO: 50 |
| shmiR13 | GGUAUAUUGCUGUUGACAGUGAGCGAC<br>GACAUCAUGGUAUUCCCCUACUGUGAA<br>GCAGAUGGGUAGGGGAAUACCAUGAUG<br>UCGCCGCCUACUGCCUCGGACUUCAA | SEQ ID NO: 51 |
| shmiR14 | GGUAUAUUGCUGUUGACAGUGAGCGUG<br>AGAAGCAGAUGAAUAUGAGACUGUGAA<br>GCAGAUGGGUCUCAUAUUCAUCUGCUU<br>CUCUCGCCUACUGCCUCGGACUUCAA | SEQ ID NO: 52 |

TABLE 3-continued shmiR sequences

| shmiR | shmiR sequences (5'-3') | SEQ ID NO: |
|---|---|---|
| shmiR15 | GGUAUAUUGCUGUUGACAGUGAGCGAA<br>GGAGAAGAUGGAGGCUGAUACUGUGAA<br>GCAGAUGGGUAUCAGCCUCCAUCUUCU<br>CCUCCGCCUACUGCCUCGGACUUCAA | SEQ ID NO: 53 |
| shmiR16 | GGUAUAUUGCUGUUGACAGUGAGCGAG<br>AAGAAGCUGAGAAGCUAAAACUGUGAA<br>GCAGAUGGGUUUUAGCUUCUCAGCUUC<br>UUCCCGCCUACUGCCUCGGACUUCAA | SEQ ID NO: 54 |
| shmiR17 | GGUAUAUUGCUGUUGACAGUGAGCGAA<br>GGUAGAGAAGCAGAUGAAUACUGUGAA<br>GCAGAUGGGUAUUCAUCUGCUUCUCUA<br>CCUCCGCCUACUGCCUCGGACUUCAA | SEQ ID NO: 55 |

TABLE 4 shmiR encoding cassettes

| shmiR | shmiR-encoding cassettes (5'-3') | SEQ ID NO: |
|---|---|---|
| shmiR2 | GGTATATTGCTGTTGACAGTGAGCG<br>TAGCAGATGAATATGAGTCCAACTG<br>TGAAGCAGATGGGTTGGACTCATAT<br>TCATCTGCTTCGCCTACTGCCTCGG<br>ACTTCAA | SEQ ID NO: 56 |
| shmiR3 | GGTATATTGCTGTTGACAGTGAGCG<br>AGAGGTAGAGAAGCAGATGAAACTG<br>TGAAGCAGATGGGTTTCATCTGCTT<br>CTCTACCTCGCGCCTACTGCCTCGG<br>ACTTCAA | SEQ ID NO: 57 |
| shmiR4 | GGTATATTGCTGTTGACAGTGAGCG<br>ACTGAGAAGCTAAAGGAGCTAACTG<br>TGAAGCAGATGGGTTAGCTCCTTTA<br>GCTTCTCAGCCGCCTACTGCCTCGG<br>ACTTCAA | SEQ ID NO: 58 |
| shmiR5 | GGTATATTGCTGTTGACAGTGAGCG<br>ATAGAGCGACATCATGGTATTACTG<br>TGAAGCAGATGGGTAATACCATGAT<br>GTCGCTCTAGCGCCTACTGCCTCGG<br>ACTTCAA | SEQ ID NO: 59 |

TABLE 4-continued

| shmiR encoding cassettes | | |
|---|---|---|
| shmiR | shmiR-encoding cassettes (5'-3') | SEQ ID NO: |
| shmiR6 | GGTATATTGCTGTTGACAGTGAGCG AGTGACAAATTTAGTGGCCATACTG TGAAGCAGATGGGTATGGCCACTAA ATTTGTCACACGCCTACTGCCTCGG ACTTCAA | SEQ ID NO: 60 |
| shmiR7 | GGTATATTGCTGTTGACAGTGAGCG AATGGTGCAACAGCAGAAGAGACTG TGAAGCAGATGGGTCTCTTCTGCTG TTGCACCATACGCCTACTGCCTCGG ACTTCAA | SEQ ID NO: 61 |
| shmiR9 | GGTATATTGCTGTTGACAGTGAGCG AGTAGAGAAGCAGATGAATATACTG TGAAGCAGATGGGTATATTCATCTG CTTCTCTACCCGCCTACTGCCTCGG ACTTCAA | SEQ ID NO: 62 |
| shmiR11 | GGTATATTGCTGTTGACAGTGAGCG AGGTTTTAACAGCAGGCCCCGACTG TGAAGCAGATGGGTCGGGGCCTGCT GTTAAAACCACGCCTACTGCCTCGG ACTTCAA | SEQ ID NO: 63 |
| shmiR13 | GGTATATTGCTGTTGACAGTGAGCG ACGACATCATGGTATTCCCCTACTG TGAAGCAGATGGGTAGGGGAATACC ATGATGTCGCCGCCTACTGCCTCGG ACTTCAA | SEQ ID NO: 64 |
| shmiR14 | GGTATATTGCTGTTGACAGTGAGCG TGAGAAGCAGATGAATATGAGACTG TGAAGCAGATGGGTCTCATATTCAT CTGCTTCTCTCGCCTACTGCCTCGG ACTTCAA | SEQ ID NO: 65 |
| shmiR15 | GGTATATTGCTGTTGACAGTGAGCG AAGGAGAAGATGGAGGCTGATACTG TGAAGCAGATGGGTATCAGCCTCCA TCTTCTCCTCCGCCTACTGCCTCGG ACTTCAA | SEQ ID NO: 66 |
| shmiR16 | GGTATATTGCTGTTGACAGTGAGCG AGAAGAAGCTGAGAAGCTAAAACTG TGAAGCAGATGGGTTTTAGCTTCTC AGCTTCTTCCCGCCTACTGCCTCGG ACTTCAA | SEQ ID NO: 67 |
| shmiR17 | GGTATATTGCTGTTGACAGTGAGCG AAGGTAGAGAAGCAGATGAATACTG TGAAGCAGATGGGTATTCATCTGCT TCTCTACCTCCGCCTACTGCCTCGG ACTTCAA | SEQ ID NO: 68 |

Example 1—Design of shmiRs Targeting PABPN1

Sequences representing potential targets for design of siRNA constructs were identified from the PABPN1 mRNA sequence using publicly available siRNA design algorithms (including Ambion, Promega, Invitrogen, Origene and MWG): the selected sequences were conserved in humans, non-human primates, bovine and mice species. Sequences encoding the candidate siRNAs were incorporated into a pre-miR30a scaffold in order to create a sequence encoding a short-hairpin microRNA (shmiR) comprising a 5' flanking region (SEQ ID NO: 41), a siRNA sense strand sequence (effector complement sequence), a stem/loop junction sequence (SEQ ID NO: 40), a siRNA anti-sense strand (effector sequence), and a 3' flanking region (SEQ ID NO:42). The predicted secondary structure of a representative shmiR is shown in FIG. 1C. The target regions of the PABPN1 mRNA transcript for the designed shmiRs are presented in Table 1 and corresponding shmiR effector sequences (antisense strand) are presented in Table 2.

Example 2—Generation of a Single "Silence and Replace Construct" for Simultaneous Gene Silencing of Endogenous PABPN1 and Replacement with Codon Optimised PABPN1

A single stranded adeno-associated virus type 2 (ssAAV2) plasmid expressing shmiR17 and shmiR13 (e.g., as described in Tables 3 and 4) in combination with the optPABPN1 sequence was created.

Figure 2:
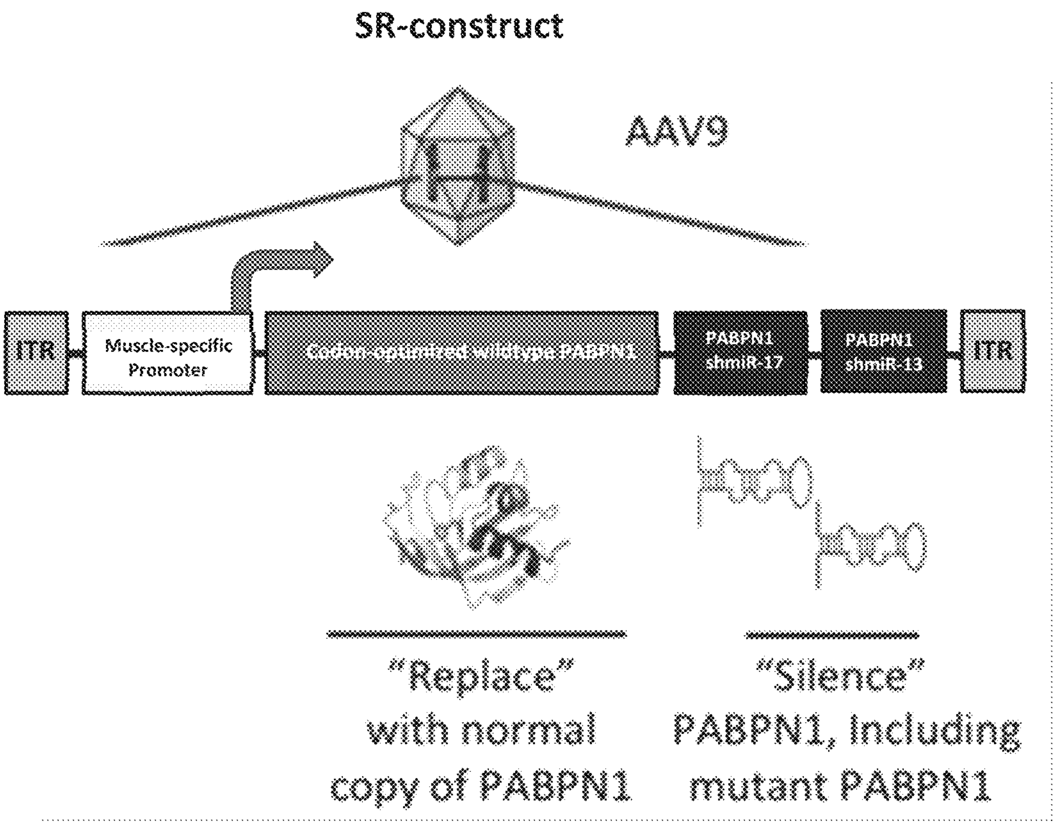
FIG. 2 is a schematic illustrating a SR-construct. In the SR-construct, the 'replace' and 'silence' cassettes are all inserted in a single vector with the Spc512 muscle specific promoter. Two shmiR sequences are inserted in the 3'UTR of the codon-optimised PABPN1 cassette.

The silence and replace construct (hereinafter "SR-construct") was generated by subcloning DNA sequences encoding shmiR17 and shmiR13 (as described in Table 4) into the 3' untranslated region of the optPABPN1 transcript in the pAAV2 vector backbone (pAAV-shmiR viral plasmid). Expression of both optPABPN1 and the two shmiRs in a single transcript is driven by the muscle specific promoter Spc512. A schematic of the SR-construct is provided in FIG. 1(A), FIG. 1(B), and FIG. 2.

Recombinant pseudotyped AAV vector stocks were then generated. Briefly, HEK293T cells were cultured in cell factories in Dulbecco's modified Eagle's medium, supplemented with 10% FBS, and incubated at 37° C. and 5% $CO_2$. The pAAV-shmiR viral plasmid (the SR-construct) and a pAAVhelper and pAAVrepcap8 plasmid or pAAVhelper and pAAV repcap9 or pAAV helper and pAAVRH74 plasmid were complexed with Calcium Phosphate according to the manufacturer's instructions. Triple-transfections were then performed with the pAAV-shmiR plasmid (the SR-construct) in combination with the pAAVhelper and one of the following capsids; pAAVrepcap8, pAAVrepcap9 or pAAVRH74, in the HEK293T cells. The HEK293T cells were then cultured for a period of 72 hours at 37° C. and 5% $CO_2$, after which time the cells were lysed and particles expressing the SR-construct were purified by iodixanol (Sigma-Aldrich) step-gradient ultracentrifugation followed by cesium chloride ultracentrifugation. The number of vector genomes was quantified by quantitative polymerase chain reaction (Q-PCR).

Example 3—In Vivo Studies with a Single Vector "Silence and Replace" Approach In order to test the in vivo efficacy of the SR-construct described in Example 2 in a relevant disease model of OPMD, the SR-construct was administered individually, at a range of doses, via intramuscular injection into the Tibialis anterior (TA) muscle of 10-12 week old A17 mice. The doses were set at $7.5\times10^{11}$, $2.5\times10^{11}$, $5\times10^{10}$, $1\times10^{10}$, $2\times10^{9}$, and $4\times10^{8}$ vector genomes (vg) per muscle. Saline injected age-matched A17 mice served as the untreated group. Mice were sacrificed at either 14 or 20 weeks post treatment.

Figure 3A:
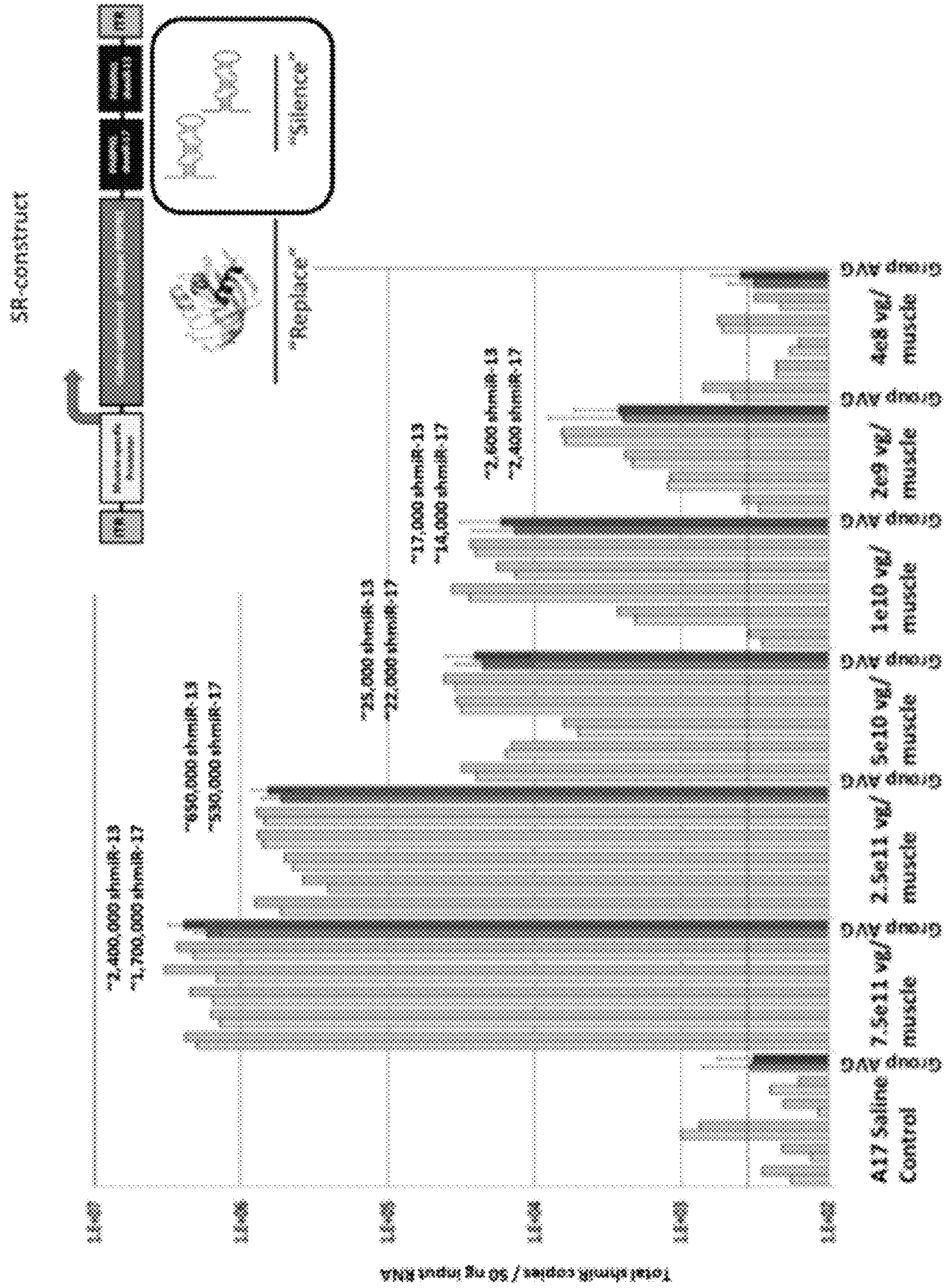
FIG. 3A shows expression of shRNA in (Tibialis anterior) TA muscles of A17 mice injected with the SR-construct. RNA was extracted from TA samples 14 weeks post SR-construct dosing.
Figure 3B:
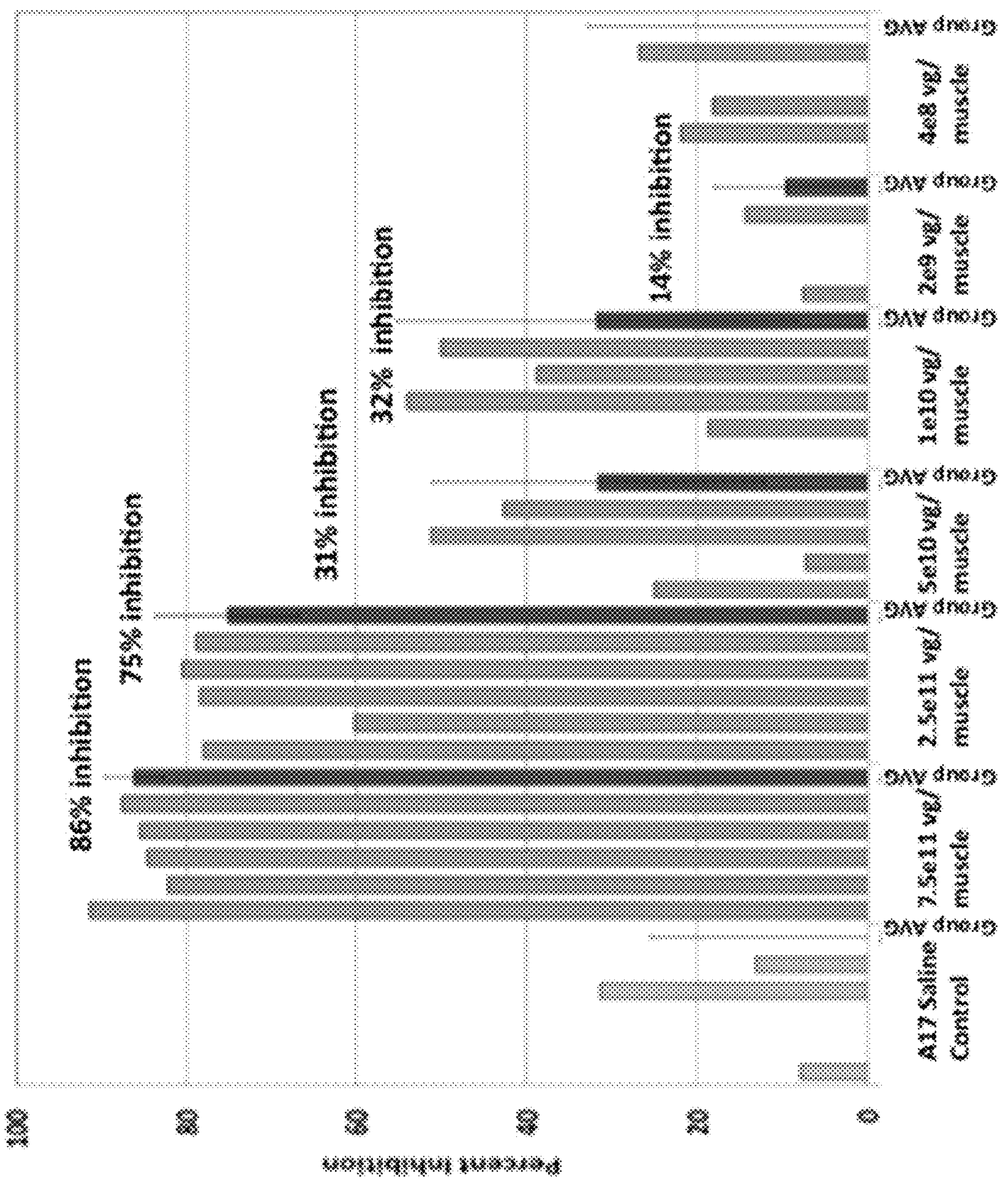
FIG. 3B shows silencing of PABPN1 expression (including expPABPN1) in TA muscles of A17 mice treated with the SR-construct. RNA was extracted from TA samples 14 weeks post SR-construct dosing.
Figure 3C:
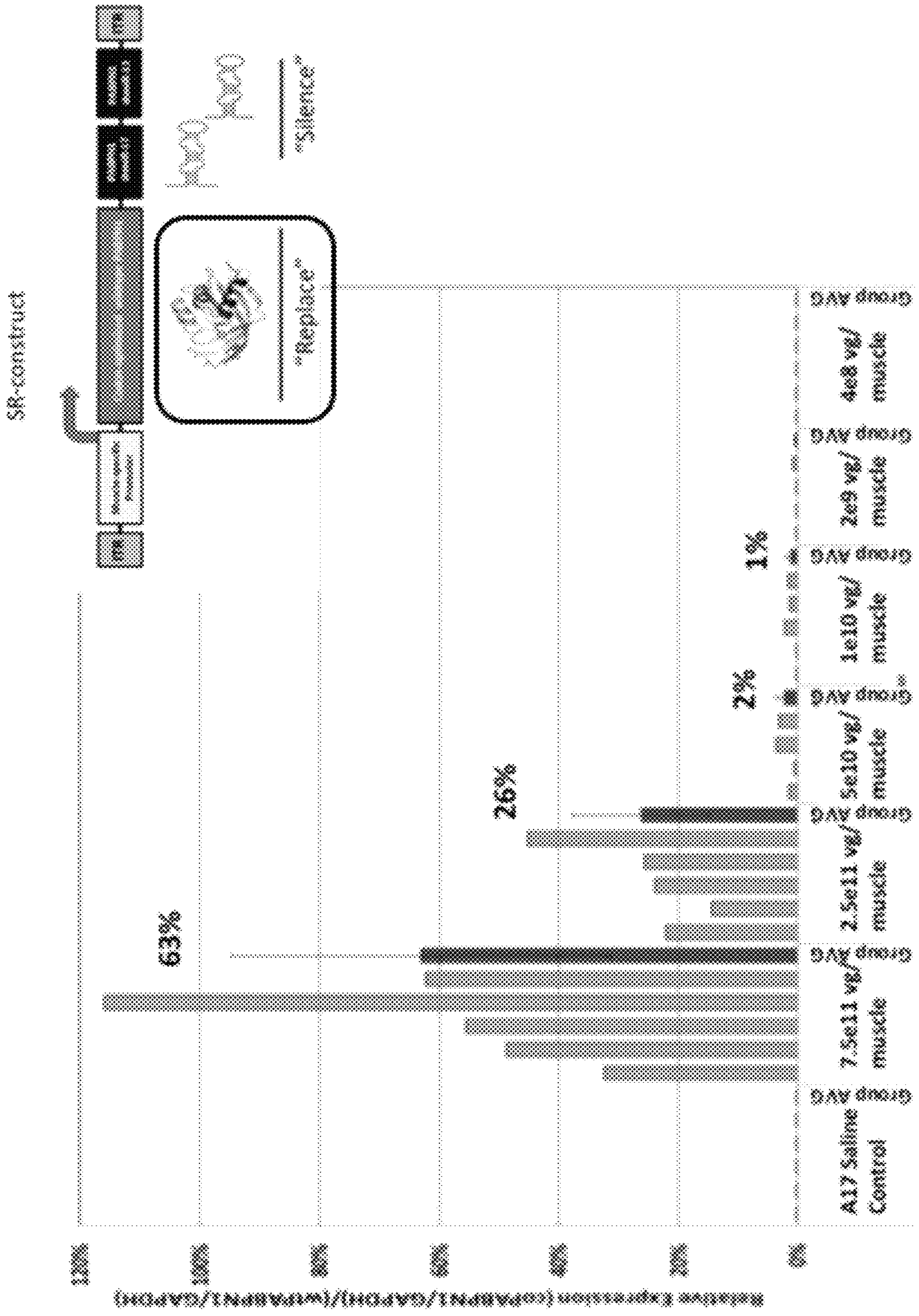
FIG. 3C illustrates restoration of normal PABPN1 levels in the A17 mouse model upon treatment with the SR-construct. RNA was extracted from TA muscle samples 14 weeks post SR-construct dosing.

Example 4—Quantitative Measurements of shmiR Production, PABPN1 Silencing, and Codon-Optimized PABPN1 Expression in SR-Construct Treated A17 Mice Fourteen weeks after SR-construct treatment, the TA muscles of the A17 mice of Example 3 were harvested and RNA extracted. SR-construct-dependent expression of shmiRs in TA muscles was quantified (FIG. 3A). The quantified expression level of shmiRs was dependent on SR-construct dose, as was silencing of PABPN1 (including expPABPN1) (FIG. 3B), and restoration of normal PABPN1 levels (FIG. 3C).

Figure 4A:
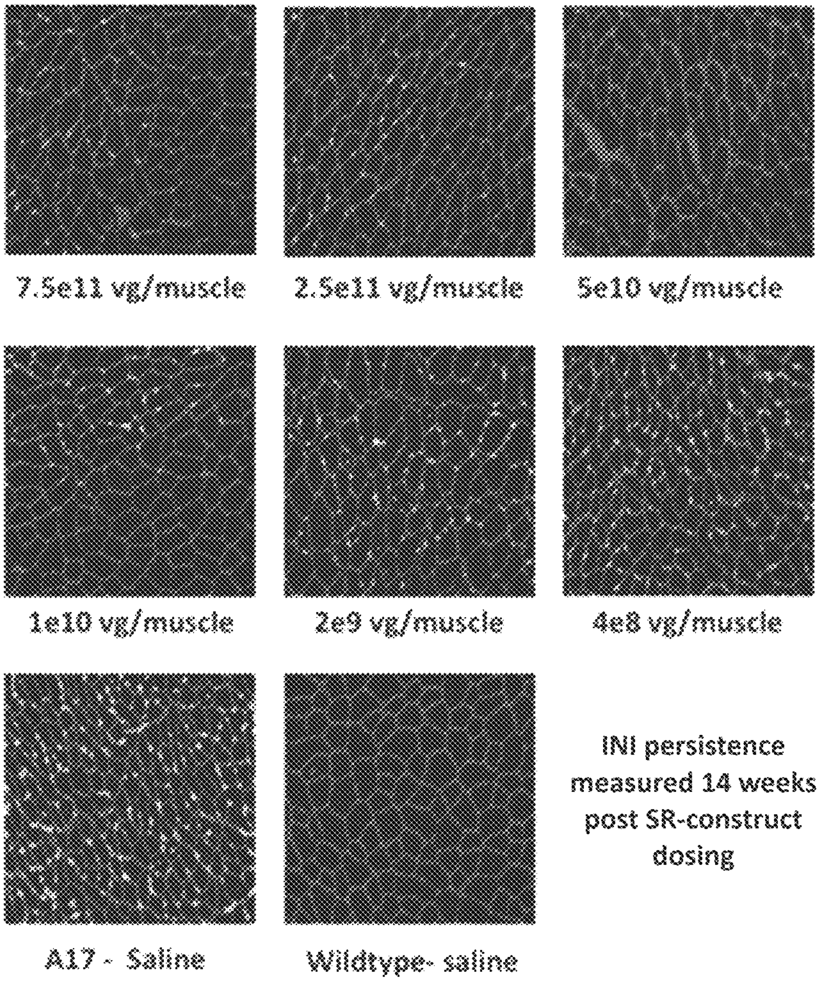
FIG. 4A shows significantly reduced formation of insoluble aggregates (intranuclear inclusions (INIs)) containing PABPN1 with a SR-construct dose effect. The SR-construct was injected in TA muscles of A17 mice. Muscles were collected and mounted for histological studies 14 weeks post SR-construct dosing. Immunofluorescence for PABPN1 is shown in green and immunofluorescence for Laminin is shown in red.
Figure 4B:
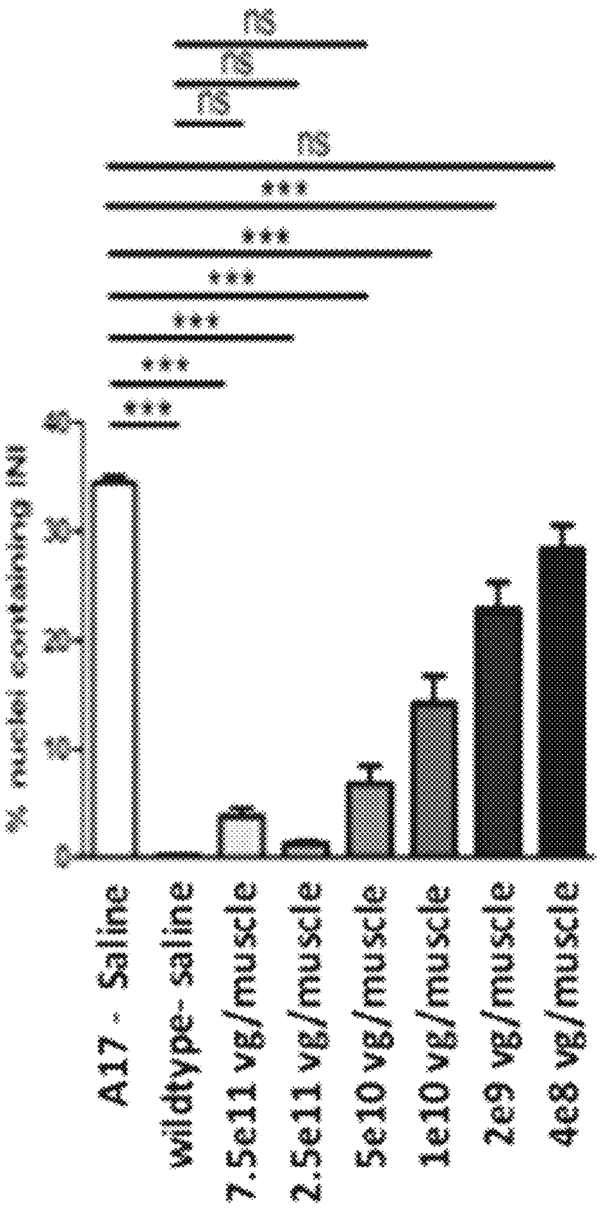
FIG. 4B shows quantification of percentage of nuclei containing INIs in muscle sections indicating that treatment with the SR-construct significantly reduces the amount of INIs compared to untreated A17 TA muscles (one-way Anova test with Bonferroni post-doc test, ***$p<0.001$, ns: not significant).

Example 5—Reduction of Intranuclear Inclusions (INIs) in SR-Construct Treated A17 Mice The impact of the SR-construct on the persistence of intranuclear inclusions (INIs) was tested in the week 14 A17 mice of Example 3. FvB wildtype mice were also included as healthy comparators. Fourteen weeks after AAV injection, muscles were collected and mounted for histological studies. Sections were pre-treated with 1M KCl to preferentially elute all soluble PABPN1 from the tissue. Immunofluorescence for PABPN1 (green) and Laminin, an abundant protein in the extracellular matrix of muscle cells (red) was detected in sections of treated muscles and showed significant reduction in the number of PABPN1-positive intranuclear inclusions (INIs) in SR-construct-treated muscles with a dose effect (FIG. 4A). Quantification of percentage of nuclei containing INIs in muscle sections indicates that treatment with the SR-construct significantly reduces the amount of INIs compared to untreated A17 muscles (One-way Anova test with Bonferroni post-doc test, ***$p<0.001$, ns: not significant) (FIG. 4B).

Figure 5A:
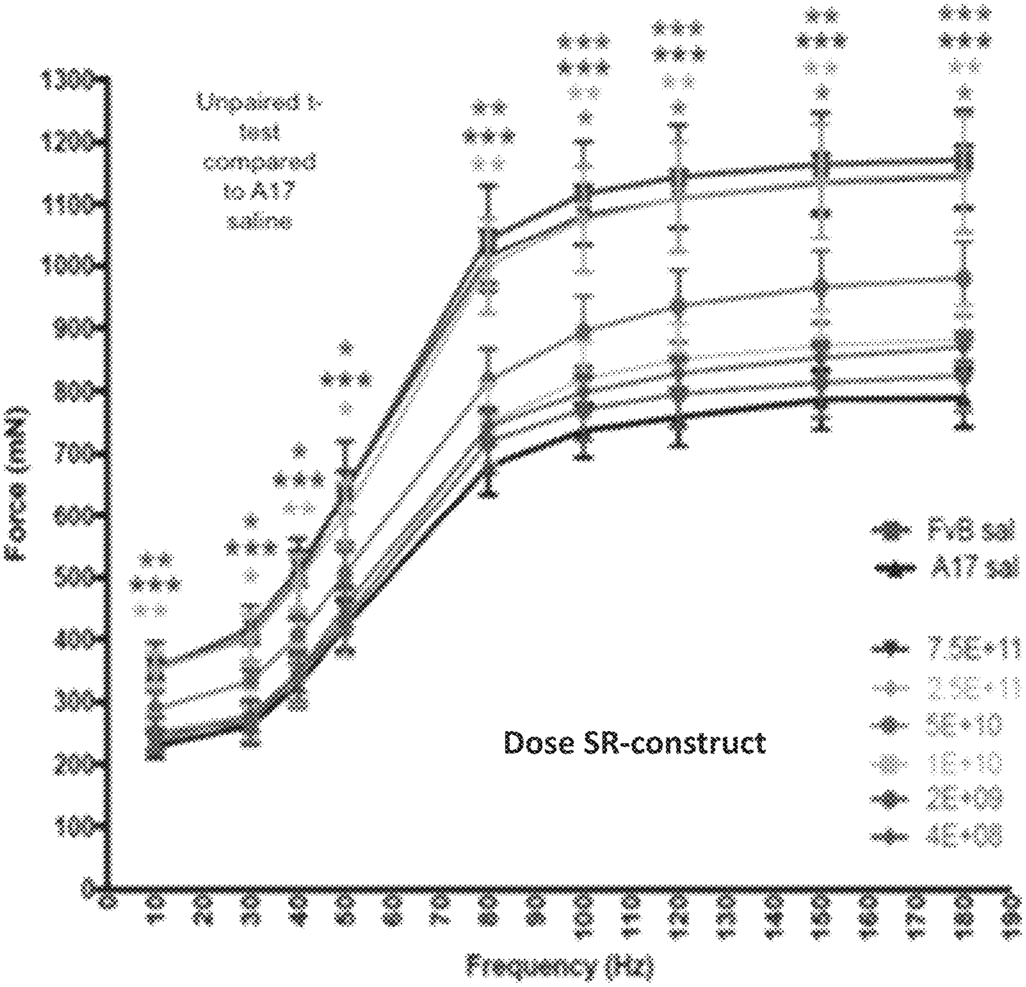
FIG. 5A shows a significant increase in the maximal force generated by TA muscles of A17 mice in an SR-construct dose-dependent manner. Maximal force was measured by in situ muscle physiology.
Figure 5B:
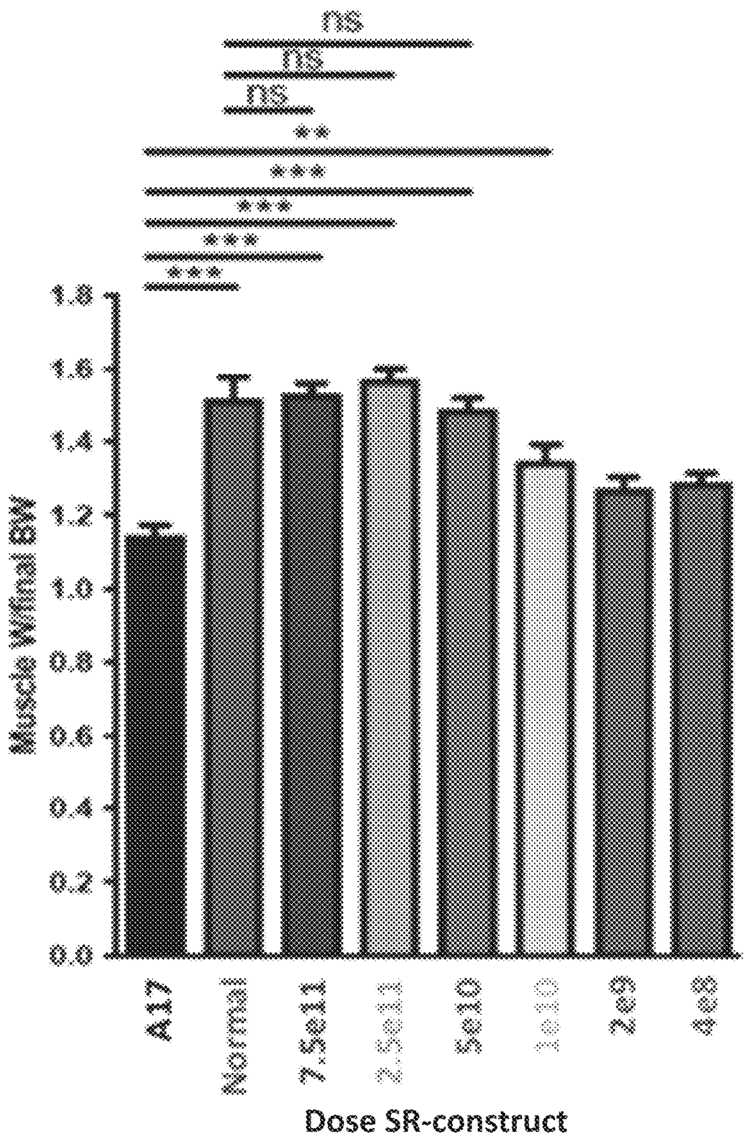
FIG. 5B shows muscle weight normalized to body weight (BW) of SR-construct-treated TA muscles of A17 mice. Normalized muscle weight was comparable to that of control FvB mice at doses above 1e10 vg per TA injected (mean±SEM n=10, One-way Anova test with Bonferroni post-doc test, *$p<0.05$, *$p<0.001$, $p<0.01$, ns: not significant).

Example 6—Treatment with the SR-Construct Improves the Physiological Properties and Functionality of Treated Muscles Physiological properties and functionality of treated muscles were measured in the week 14 A17 mice of Example 3. FvB wildtype mice were also included as healthy comparators. Maximal force generated by TA muscles was measured by in situ muscle physiology (FIG. 5A). SR-construct significantly increased the maximal force generated by TA muscles in a dose-dependent manner. Muscle weight normalized to body weight (BW) was also measured 14 weeks post SR-construct dosing (FIG. 5B). Muscle weight normalized to body weight of SR-treated muscles was comparable to that of control FvB mice at doses above 1e10 vg per TA injected (mean±SEM n=10, One-way Anova test with Bonferroni post-doc test, *$p<0.05$, *$p<0.001$, $p<0.01$, ns: not significant).

Example 7—Restoration of Muscle Function Over Time

Figure 6A:
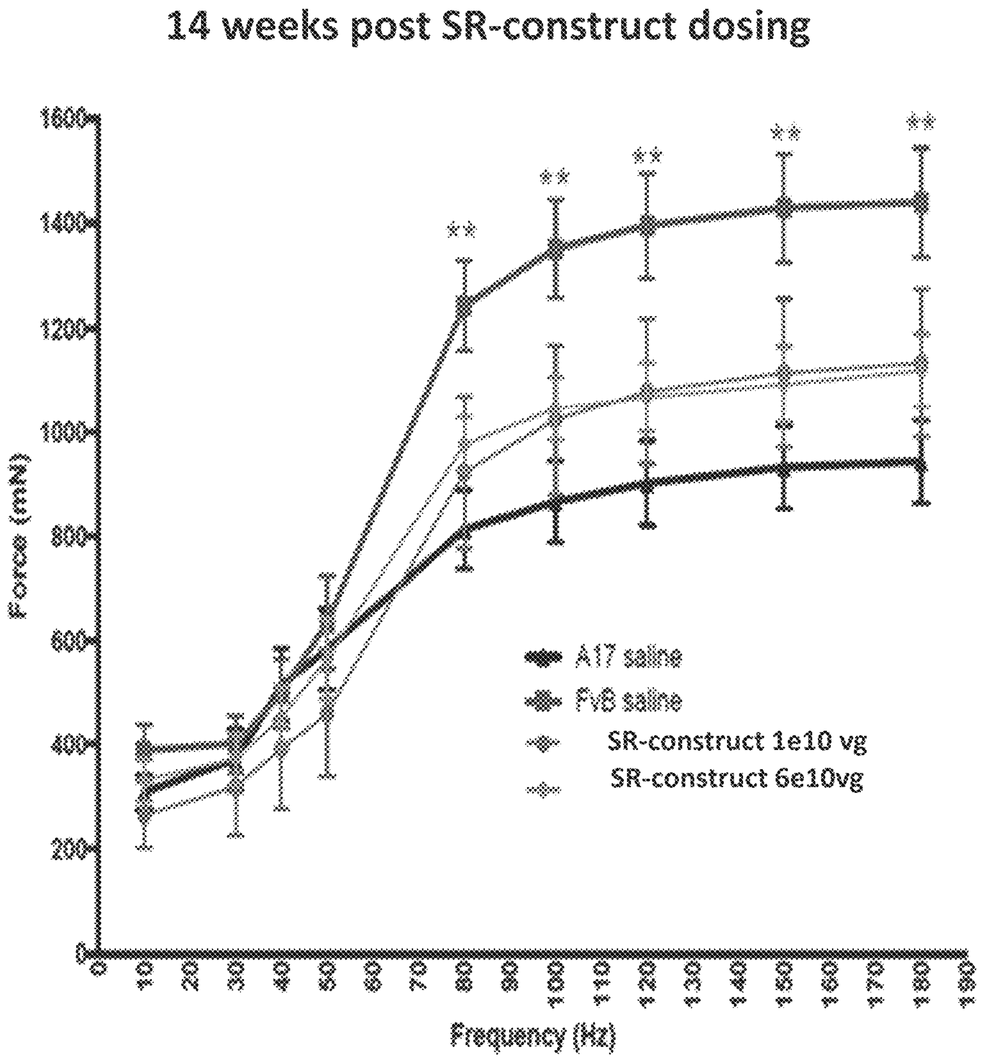
FIG. 6A shows maximal force generated by TA muscles of A17 mice 14 weeks post SR-construct dosing. Maximal force was measured by in situ muscle physiology.
Figure 6B:
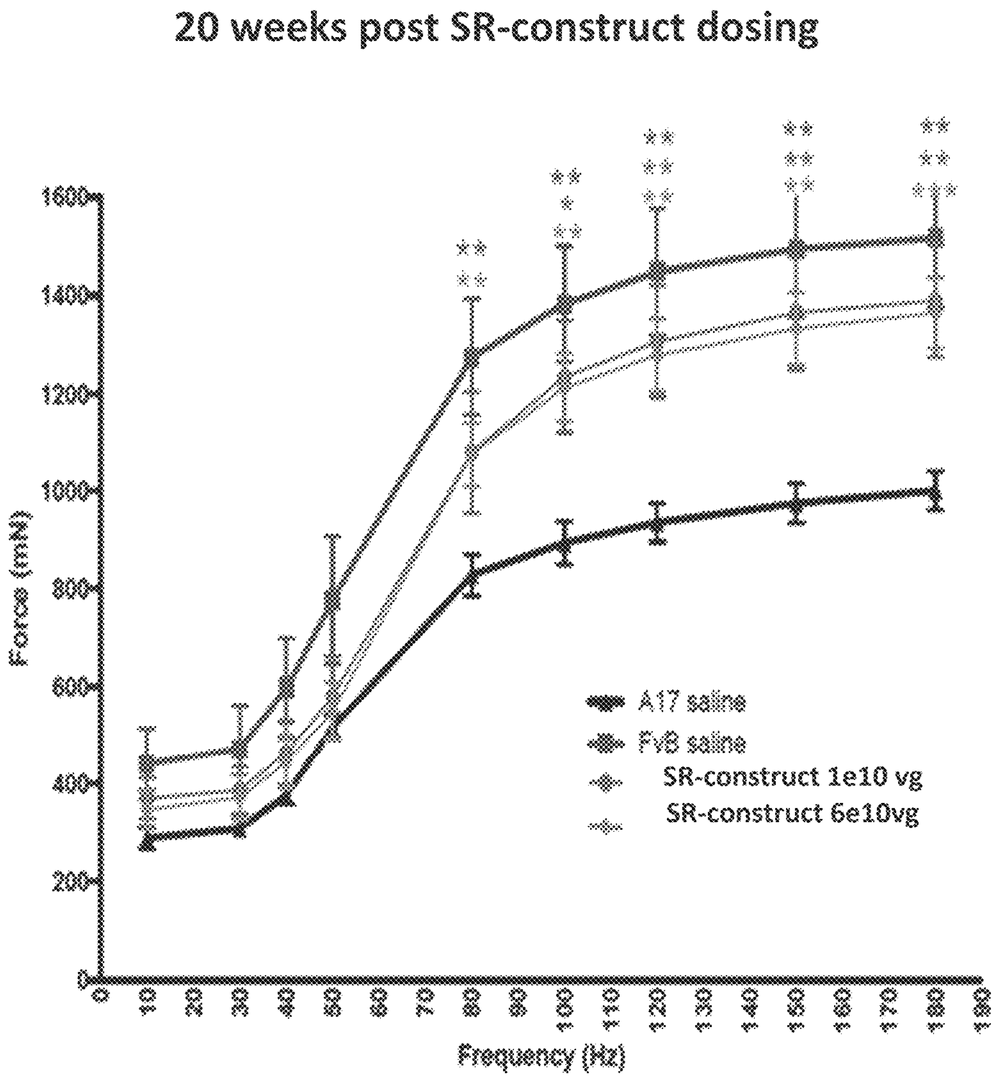
FIG. 6B shows maximal force generated by TA muscles of A17 mice 20 weeks post SR-construct dosing. Maximal force was measured by in situ muscle physiology.

Maximal force generated by TA muscles of SR-construct-treated A17 mice and FvB wildtype mice was measured by in situ muscle physiology at 14 weeks post SR-construct dosing (FIG. 6A) and at 20 weeks post SR-construct dosing (FIG. 6B). For intermediate doses (1e10 vg and 6e10 vg per TA), beneficial effect on muscle force was much more pronounced at 20 weeks compared to 14 weeks after injection (mean±SEM n=10, One-way Anova test with Bonferroni post-doc test, *$p<0.001$, $p<0.01$).

Example 8—Direct Administration to Pharyngeal Muscle of Sheep

Direct injection of the SR-construct to the pharyngeal muscles of sheep was tested PABPN1 is highly conserved from sheep to humans including all but one amino acid residue at position 95.

Figure 7A:
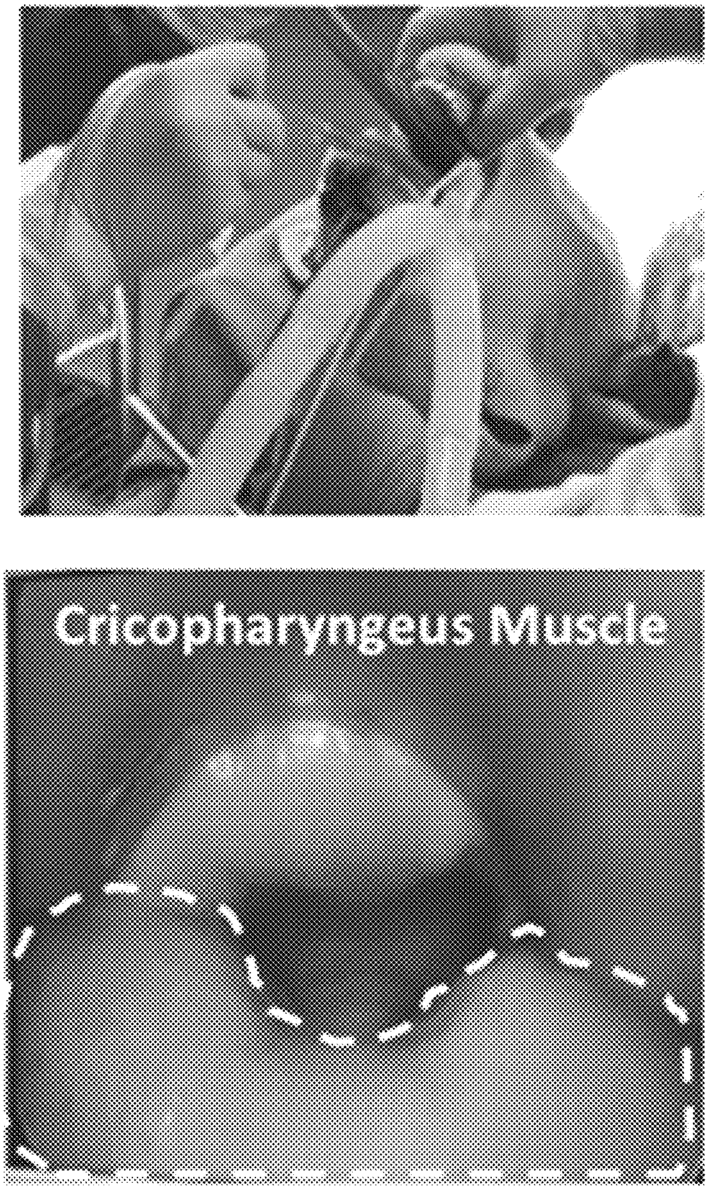
FIG. 7A shows direct injection of the SR-construct into pharyngeal muscles of sheep.

The SR-construct was directly injected into pharyngeal muscles of sheep (FIG. 7A). Two animals in the sheep study were each injected with 1.5e13 vg SR-construct into the cricopharyngeus muscle (CP) and an additional 1.0e13 vg SR-construct into the pharyngeal muscles (pharynx). The remaining 10 animals treated with SR-construct (1.0e10 vg to 1.0e13 vg) only received injections into the CP. The CP was injected with a total volume of 1.5 ml (3 injections of 0.5 ml each). The pharynx was injected with a total volume of 6 ml (2 injections of 1.5 ml on both the right and left sides).

Figure 7B:
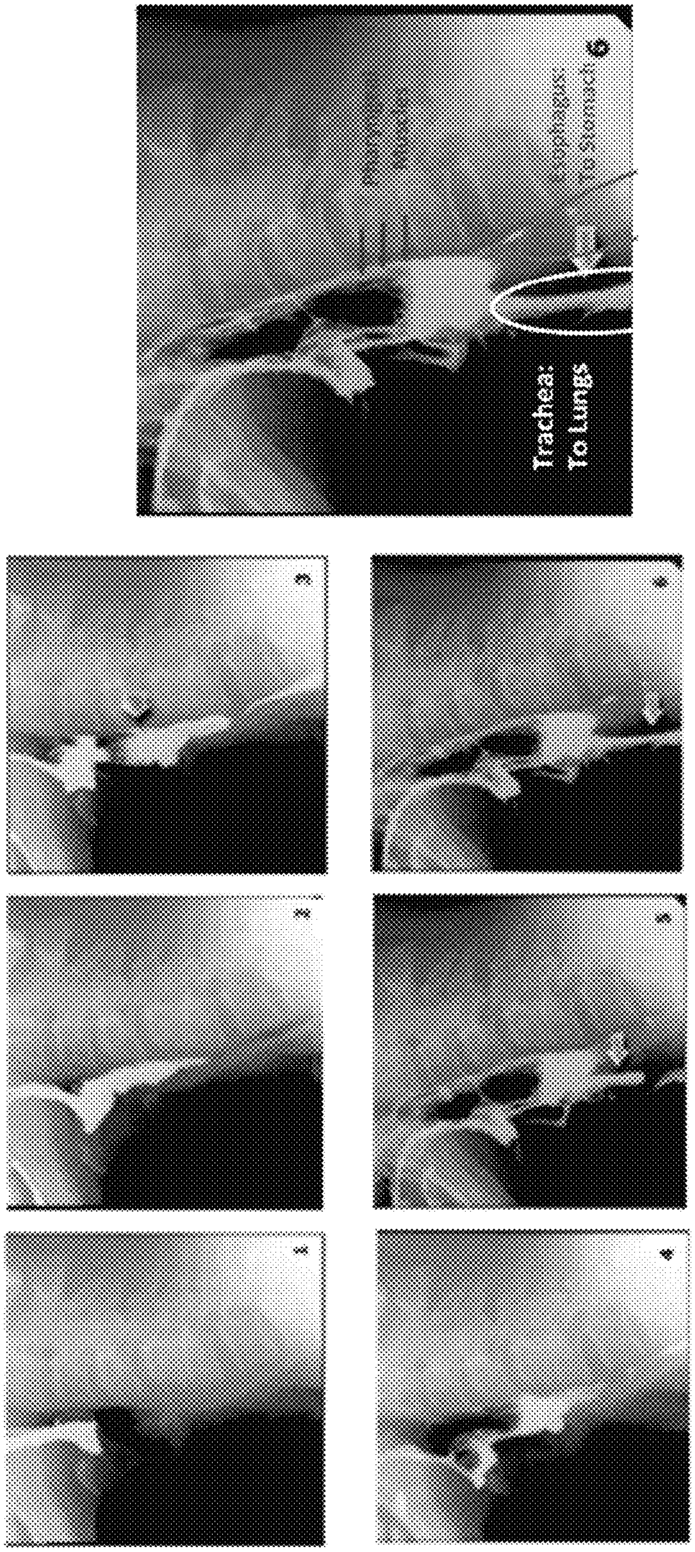
FIG. 7B shows radio images using a radiolabelled cream illustrating severe dysphagia in human OPMD patients with risk of "fausse route."

Radioimaging using a radiolabeled cream illustrates the severe dysphagia in human OPMD patients with risks of “fausse route” (FIG. 7B).

Example 9—Design, Production and Testing of Modified AAV VP1 Sequences

In this example, AAVs were designed and prepared having a viral capsid protein subunit 1 (VP1) into which specific sequence modification i.e., amino acid substitutions, were introduced to the phospholipase A2 (PLA2) domain and flanking sequence to restore phospholipase activity and viral functionality of AAVs when produced in insect cells. Further, based on a multiple sequence alignment performed for VP1 subsequences comprising the PLA2 domain and flanking sequences for various representative AAV serotypes, a consensus VP1 subsequence comprising the PLA2 domain and flanking sequence was prepared including the sequence modifications designed to restore phospholipase activity. This wildtype AAV9 VP1 subsequence is set forth in SEQ ID NO: 87.

9.1 Design of Modified AAV9 VP1 Sequences

Sequence alignments were performed using the BLASTp alignment tool for the N-terminal 180 amino acids from the VP1 protein of AAV9 (SEQ ID NO: 89), AAV8 (SEQ ID NO: 93) and AAV2 (SEQ ID NO: 97). Based on these alignments, the PLA2 domain and flanking sequences from AAV8 and AAV9 were shown to be highly conserved to the corresponding sequence in AAV2. Based on these sequence alignments, modified AAV9 VP1 and AAV8 VP1 sequences were designed in silico. The modified AAV9 VP1 sequence was designed by substituting the amino acids at positions 42, 67, 81, 84 and 85 of the sequence set forth in SEQ ID NO: 89 with the amino acids which occur at the corresponding positions in the AAV2 VP1 sequence set forth in SEQ ID NO: 97, i.e., A42S, A67E, Q81R, K84D and A85S within the sequence of SEQ ID NO: 89. One of the positions substituted in the modified AAV9 VP1 sequence was in the region flanking the PLA2 domain (but considered likely to be involved in folding and/or activity of the PLA2 domain), and four of the residue positions modified resided within the PLA2 domain itself. Similarly, a modified AAV8 VP1 sequence was designed by substituting the amino acids at positions 42, 67, 81, 84, 85 and 105 of the sequence set forth in SEQ ID NO: 93 with the amino acids which occur at the corresponding positions in the AAV2 VP1 sequence set forth in SEQ ID NO: 97, i.e., A42S, A67E, Q81R, K84D, A85S and Q105K within the sequence of SEQ ID NO: 93.

Figure 8:
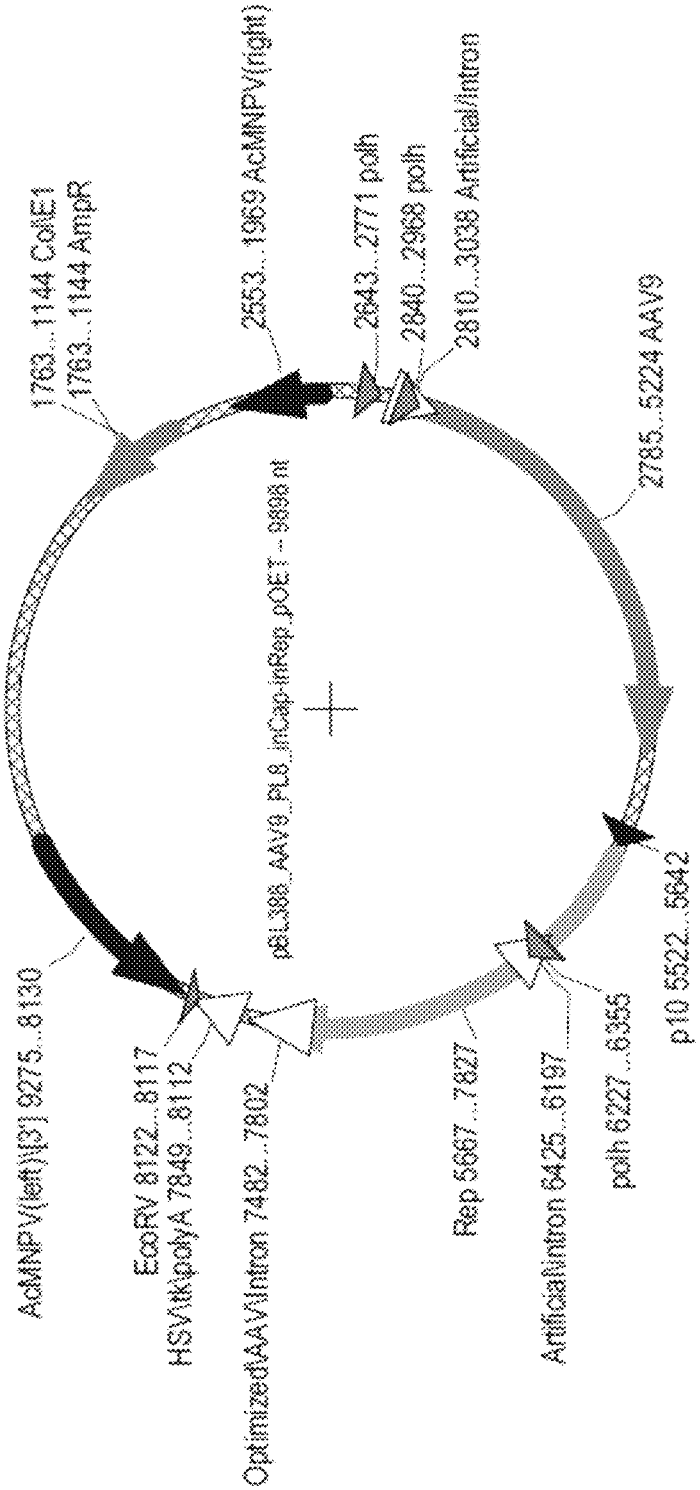
FIG. 8 is a vector map for the DNA construct designated BacAAV9-Rep-VPmod. This DNA construct was designed to express AAV Rep proteins and the modified AAV9 capsid in insect cells. The vector backbone was a baculovirus vector pOET1 backbone (Oxford Expression Technologies) and was used to prepare AAV containing the modified AAV9 capsid protein.
Figure 9:
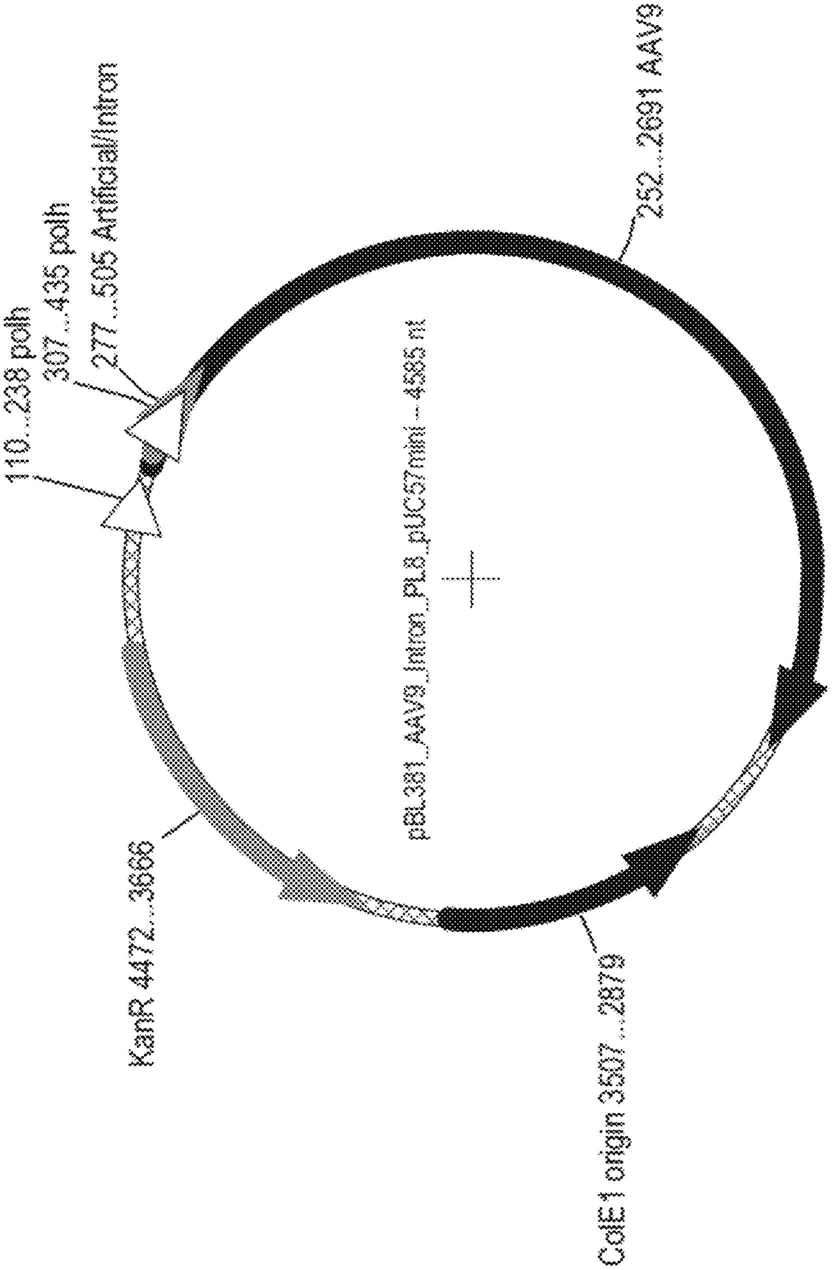
FIG. 9 is a vector map for the DNA construct designated AAV9-VPmod. This DNA construct contains a modified version of the AAV9 capsid gene which was used to prepare BacAAV9-Rep-VPmod (FIG. 8).
Figure 10:
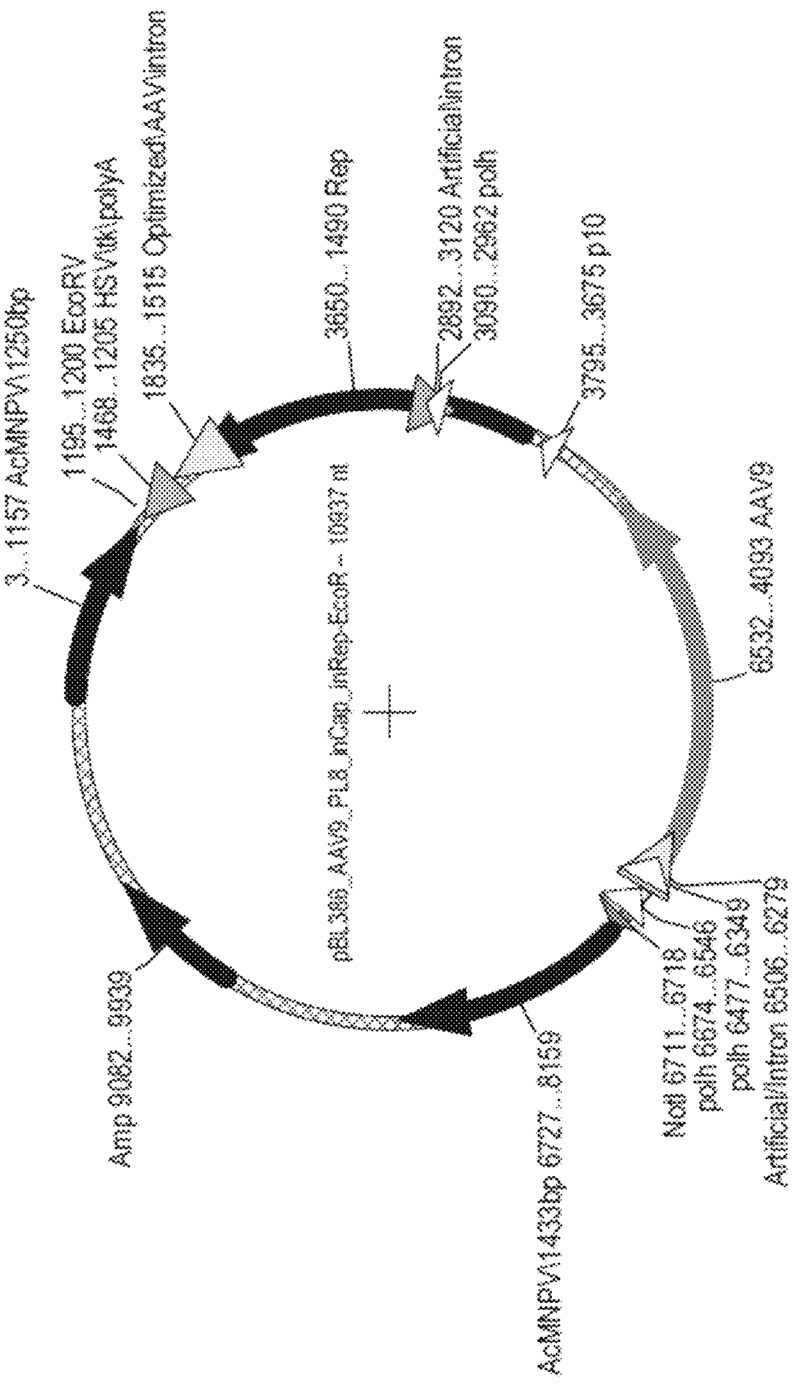
FIG. 10 is a vector map for the DNA construct designated AAV9-Rep-VPmod. This DNA construct was designed to express AAV Rep proteins and a modified AAV9 capsid in insect cells.

9.2 Production of a Baculovirus Vector Expressing Structural and Non-Structural AAV9 Proteins A baculovirus vector encoding the AAV9 capsid protein comprising subunits VP1, VP2 and VP3 and AAV9 non-structural proteins Rep78, Rep 68, Rep 52 and Rep40 was prepared (BacAAV9-Rep-VPmod, FIG. 8). Briefly, a DNA construct encoding the AAV9 capsid protein with a modified AAV9 VP1 subunit encoded by the sequence set forth in SEQ ID NO: 90, and having flanking NotI and ApaI restriction sites, was synthesized at GenScript (AAV9-VPmod, FIG. 9). A wtAAV9-Rep plasmid (Virovek, Hayward, CA) encoding the non-structural proteins Rep78, Rep68, Rep 52 and Rep40 as well as the Capsid Proteins VP1, VP2 and VP3 and the Assembly-Activating Protein (AAP) was used as a backbone to accept the AAV9-VPmod DNA construct. Both the AAV9-VPmod DNA construct and wtAAV9-Rep plasmid were digested with NotI and ApaI, after which the AAV9-VPmod DNA construct was then ligated into the wtAAV9-Rep plasmid backbone in place of the wt capsid protein encoding sequence to yield AAV9-Rep-VPmod (FIG. 10). The AAV9-Rep-VPmod intermediate was then cloned into the pOET1 baculovirus transfer vector (Oxford Expression Technologies). To facilitate this, an EcoRV site was inserted into AAV9-Rep-VPmod intermediate using the Quickchange technique to yield the AAV9-Rep-VPmod-EcoRV intermediate. The AAV9-Rep-VPmod-EcoRV intermediate and pOET1 (Oxford Expression Technologies) were then digested with NotI and EcoRV and the insert was then ligated into the pOET1 backbone generating the final AAV9-Rep-VPmod clone (BacAAV9-Rep-CapPL, FIG. 8).

Figure 11:
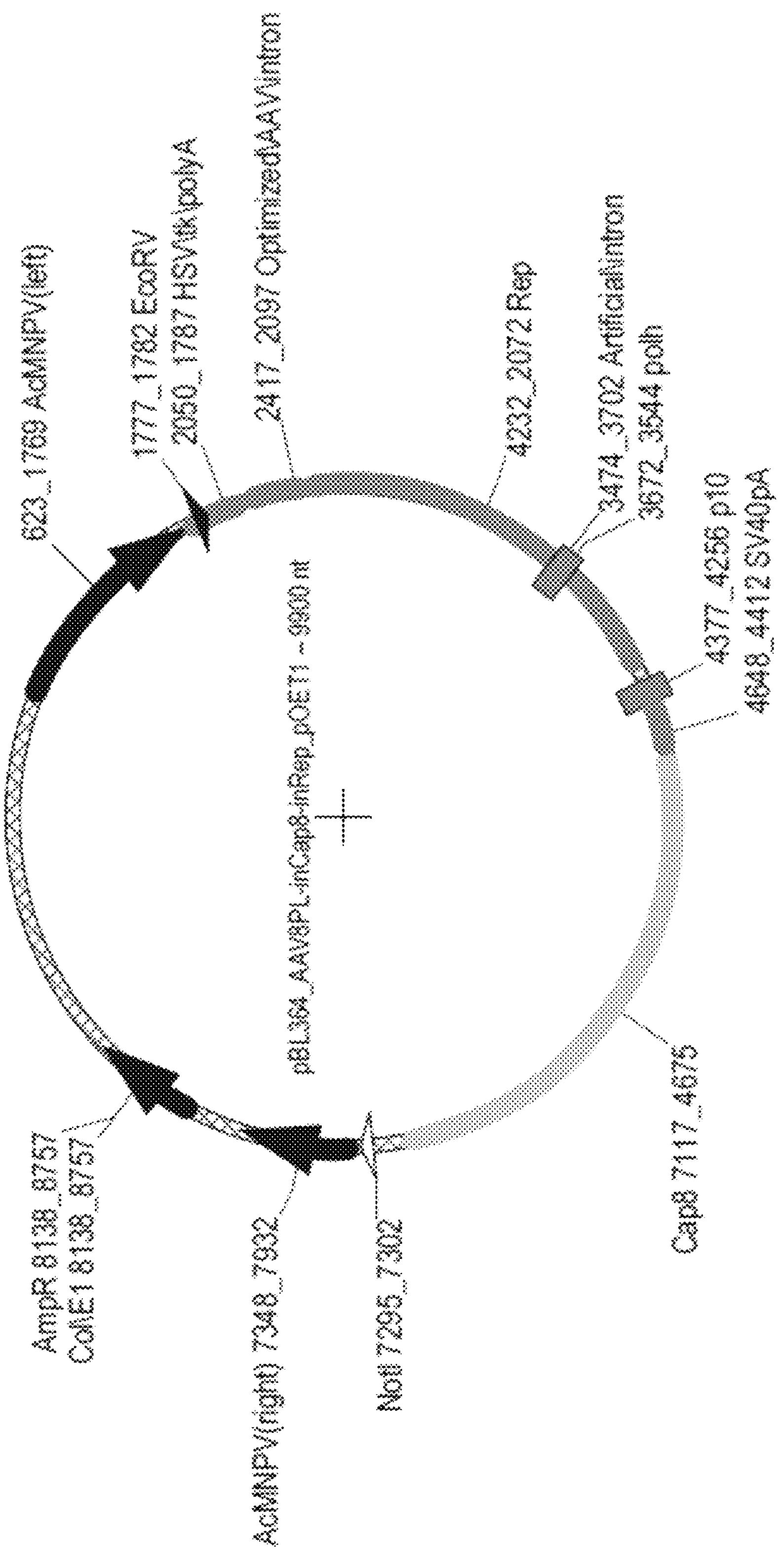
FIG. 11 is a vector map for the DNA construct designated BacAAV8-Rep-VPmod. This DNA construct was designed to express both AAV Rep proteins and the modified AAV8 capsid in insect cells. The vector backbone is a baculovirus vector pOET1 backbone (Oxford Expression Technologies) and was used to prepare AAV containing the modified AAV8 capsid protein in insect cells.
Figure 12:
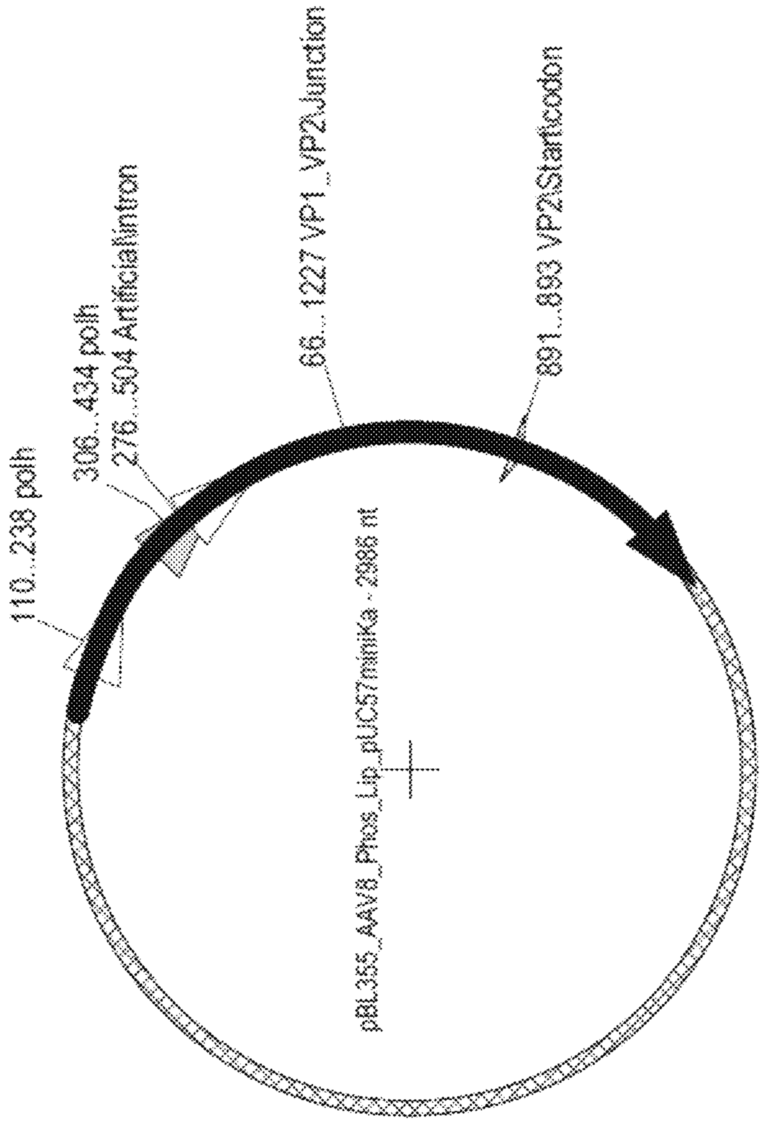
FIG. 12 is a vector map for the DNA construct designated AAV8-VPmod. This DNA construct contains a modified version of the AAV8 capsid gene which was used to prepare AAV8-Rep-VPmod (FIG. 13) and BacAAV8-Rep-VPmod (FIG. 11).
Figure 13:
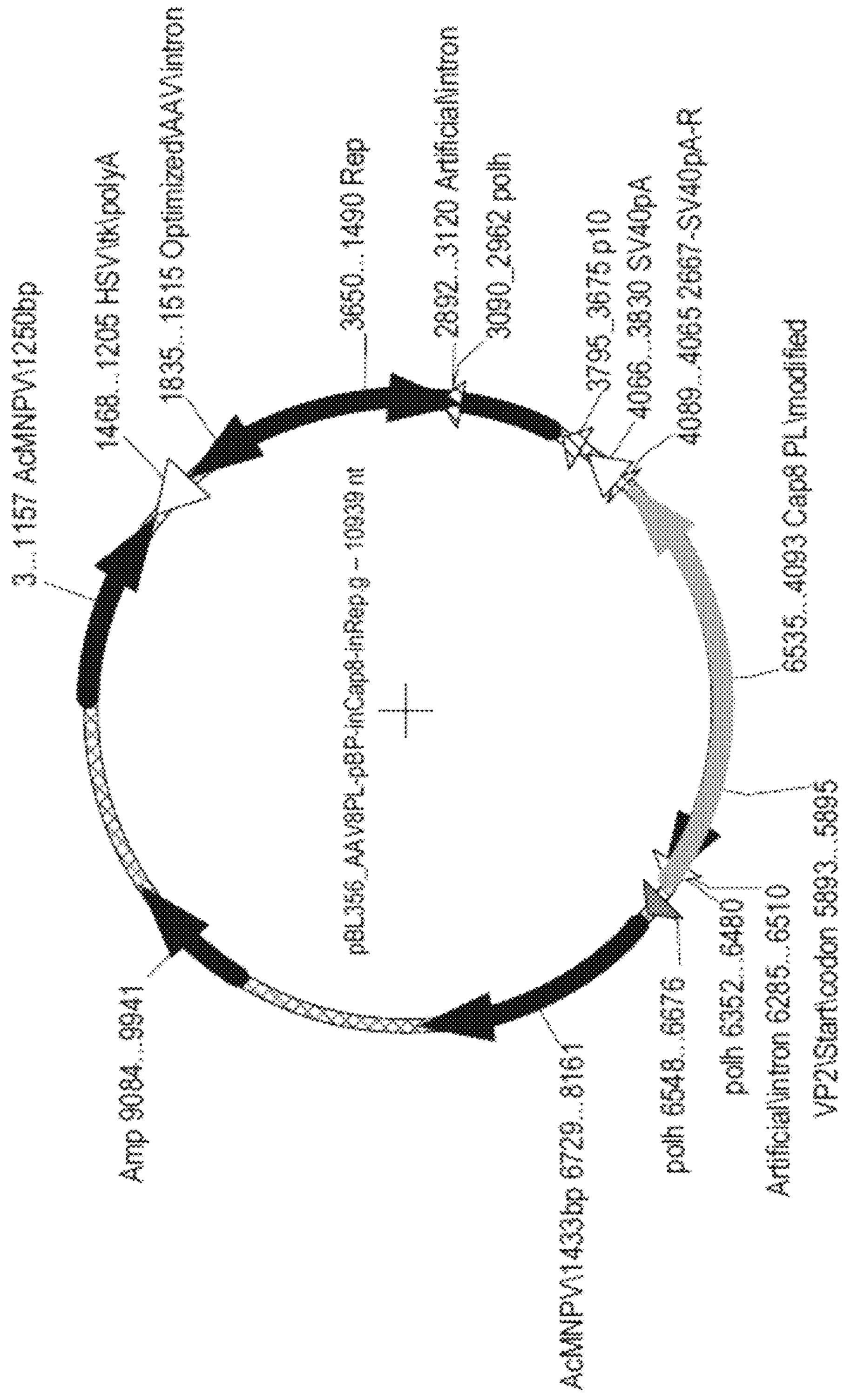
FIG. 13 is a vector map for the DNA construct designated wtAAV8-Rep/Cap. This DNA construct was designed to express AAV Rep proteins and a wt AAV8 capsid in insect cells and was used to prepare AAV containing the wtAAV8 capsid protein.

9.3 Production of a Baculovirus Vector Expressing Structural and Non-Structural AAV8 Proteins A baculovirus vector encoding the modified AAV8 capsid protein comprising subunits VP1, VP2 and VP3 and AAV8 non-structural proteins Rep78 and Rep52 was prepared (BacAAV8-Rep-VPmod, FIG. 11). Briefly, a DNA construct encoding the AAV8 capsid protein (VP1, VP2 and Vp3) with a modified VP1 subunit comprising the sequence set forth in SEQ ID NO: 94, and having flanking NotI and ApaI restriction sites, was synthesized at GenScript (AAV8-VPmod, FIG. 12). A wtAAV8-Rep/Cap plasmid (Virovek, Hayward, CA) encoding the non-structural proteins Rep78, Rep68, Rep52 and Rep40 as well as the Capsid Proteins VP1, VP2 and VP3 and the Assembly-Activating Protein (AAP) was used as a backbone to accept the AAV8-VPmod DNA construct. Both the AAV8-VPmod DNA construct and wtAAV8-Rep/Cap plasmid were digested with NotI and ApaI, after which the AAV8-VPmod DNA construct was then ligated into the wtAAV8-Rep/Cap plasmid backbone in place of the wt capsid protein encoding sequence to yield AAV8-Rep-VPmod (FIG. 13). The AAV8-Rep-VPmod intermediate was then cloned into the pOET1 baculovirus transfer vector (Oxford Expression Technologies). To facilitate this, an EcoRV site was inserted into AAV8-Rep-VPmod intermediate using the Quickchange technique to yield the AAV8-Rep-VPmod-EcoRV intermediate. The AAV8-Rep-VPmod-EcoRV intermediate and pOET1 were then digested with NotI and EcoRV and the insert was then ligated into the pOET1 backbone (Oxford Expression Technologies) generating the final AAV8-Rep-VPmod clone (BacAAV8-Rep-VPmod, FIG. 11).

9.4 Production of Baculovirus Vectors Expressing Gene of Interest (GOI)

Figure 14:
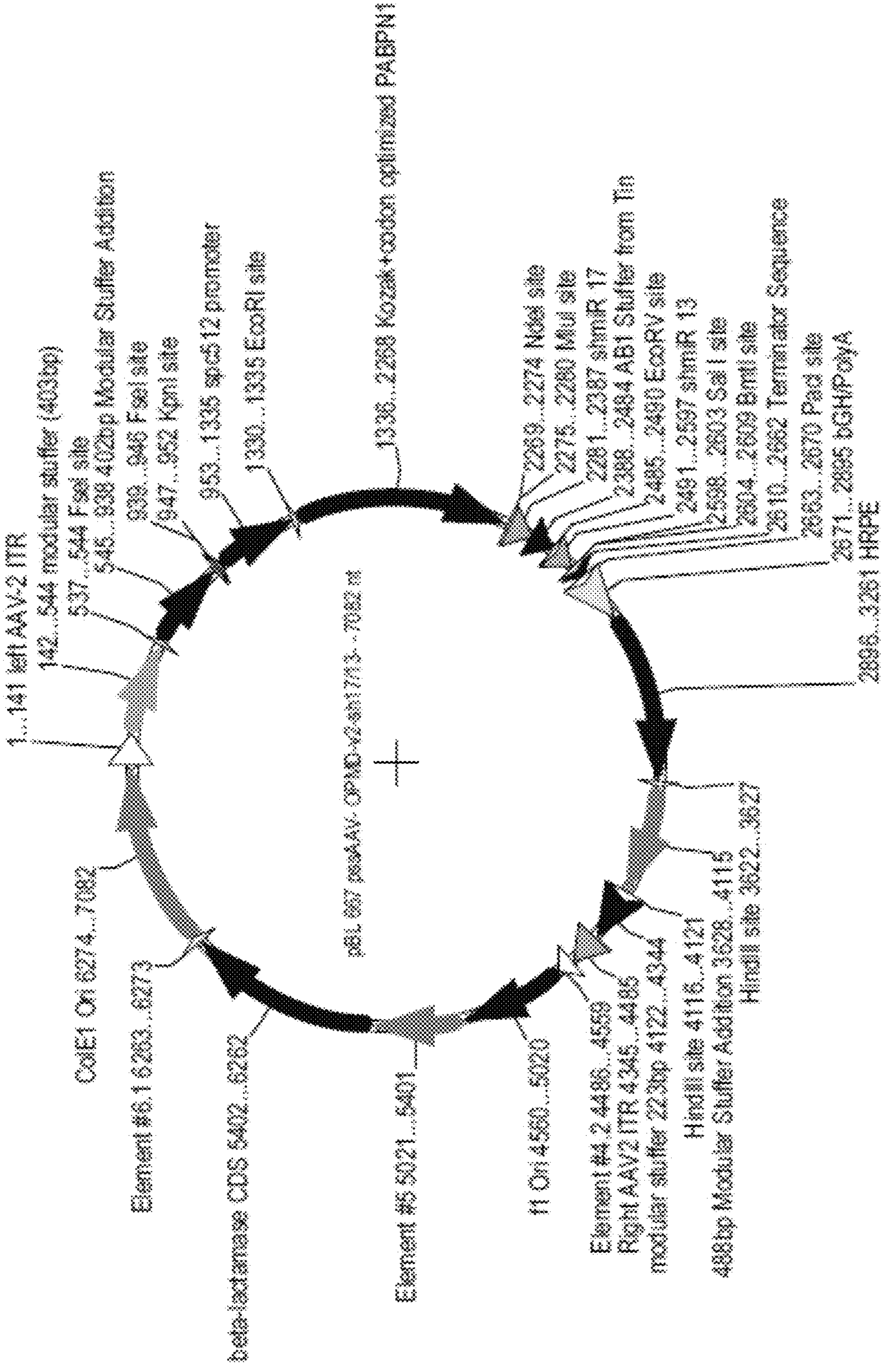
FIG. 14 is a vector map for the DNA construct designated AAV2-GOI. This DNA construct was designed to express two shmiRs flanked by AAV ITRs and was used to prepare BacAAV2-GOI (FIG. 15).
Figure 15:
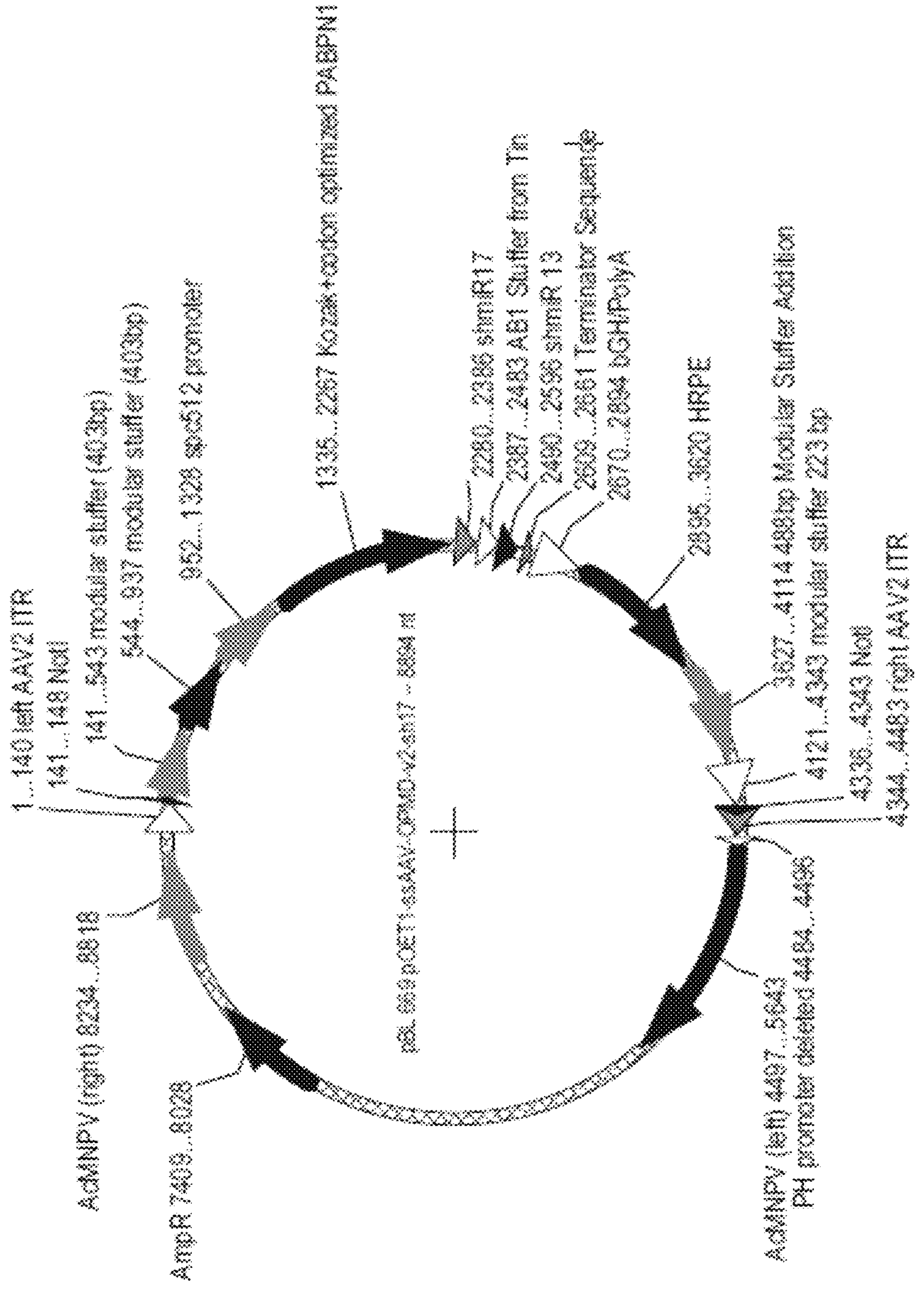
FIG. 15 is a vector map for the DNA construct designated BacAAV2-GOI. This DNA construct was designed to express two shmiRs flanked by AAV ITRs (AAV2-GOI) in the baculovirus vector pOET1 backbone (Oxford Expression Technologies). This construct was used to prepare AAV containing the modified AAV9 capsid protein expressing a GOI encoding two shmiRs.

Baculovirus vectors encoding a gene of interest (GOI) flanked by AAV2 Inverted Terminal Repeats (ITRs) were prepared. Briefly, in one instance a DNA construct encoding two shmiRs targeting a transcript of human PABPN1 flanked by AAV2 ITRs was cloned into the pOET1 baculovirus transfer vector (Oxford Expression Technologies) by digesting the AAV2-GOI construct (FIG. 14) and pOET1 (Oxford Expression Technologies) with NotI, and ligating the AAV2-GOI construct into the pOET1 backbone to generate the final clone (BacAAV2-GOI, FIG. 15). A second GOI was also prepared in an identical fashion to that described above, albeit encoding for three shmiRs targeting various regions of the HBV polymerase gene transcript.

9.5 Generation of P0 Baculovirus Stock

Baculovirus P0 stocks were generated using the Oxford Expression Technologies baculoCOMPLETE system (according to manufacturer's instructions). Briefly, 1 million Sf9 cells were seeded in a 6 well plate 1 hour prior to transfection and allowed to adhere to the plate. In 1 ml of TC100 medium, 500 ng of Bac-AAV2-GOI plasmids, BacAAV8-Rep-CapPL or BacAAV9-Rep-CapPL were mixed with 500 ng flash BAC DNA and baculoFECTIN transfection reagent (according to manufacturer's protocol). Following a 30-minute incubation at room temperature, the transfection mixture was added to the seeded Sf9 cells. The 6 well plate was incubated at 28° C. At 24 hours post transfection, 1 ml of Sf9 media was added to the cells. At 5 days post transfection, the media containing the P0 baculovirus stock was collected and stored at 4° C. P0 baculovirus were thus produced for BacAAV8-Rep-CapPL, BacAAV9-Rep-CapPL and Bac-AAV2-GOI.

9.6 AAV Prepared in Mammalian Cells

The functionality of AAV prepared in mammalian cells was compared to AAV prepared in insect cells as described above. To compare the biological activity (functionality) of the recombinant AAV prepared in mammalian and insect cells, mammalian cells were infected in vitro with various titres of viruses and expression of processed shmiRs quantified using qRT PCR assays.

For these experiments, recombinant AAV8 particles expressing 3 shmiRs targeting HBV polymerase gene transcripts were prepared in mammalian cells by a commercial supplier (Vector Biolabs; www.vectorbiolabs.com). Furthermore, recombinant AAV9 particles expressing 2 shmiRs targeting human PABPN1 were prepared by a second supplier in mammalian cells, namely Nationwide Children's hospital vector core (www.nationwidechildrens.org/research/resources-infrastructure/core-facilities/viralvector-core-clinical-manufacturing-facility).

The biological activity was assessed for (i) AAV8 with unmodified VP1 produced in mammalian cells (Vector Biolabs), (ii) AAV8 with modified VP1 (as described herein using BacAAV8-Rep-VPmod) produced by baculovirus in insect cells, and (iii) AAV8 with unmodified wt VP1 produced by baculovirus in insect cells using wtAAV8-Rep/Cap, (Ben10, Virovek, Hayward, CA), each encoding the 3 shmiRs targeting HBV polymerase gene (HBV shmiRs designated all-4_m3, shRNA8v2_p1 and All-9_p1). Briefly, JHU67 cells were infected with the modified or non-modified recombinant viral preparations described above at MOIs of 4×10e9, 8×10e9 and 1.6×10e10, and shmiR expression quantified for each of the three shmiRs 72 hrs after infection. To quantify expression of shmiRs, RNA was extracted from the infected cells using the Qiagen RNA mini kit (Qiagen). RNA was reverse transcribed using the Qiagen miScript kit (Qiagen). The cDNA was then used in a qPCR reaction with specific primers designed to amplify the shmiR targets to determine the total number of copies present in the sample.

Figure 16:
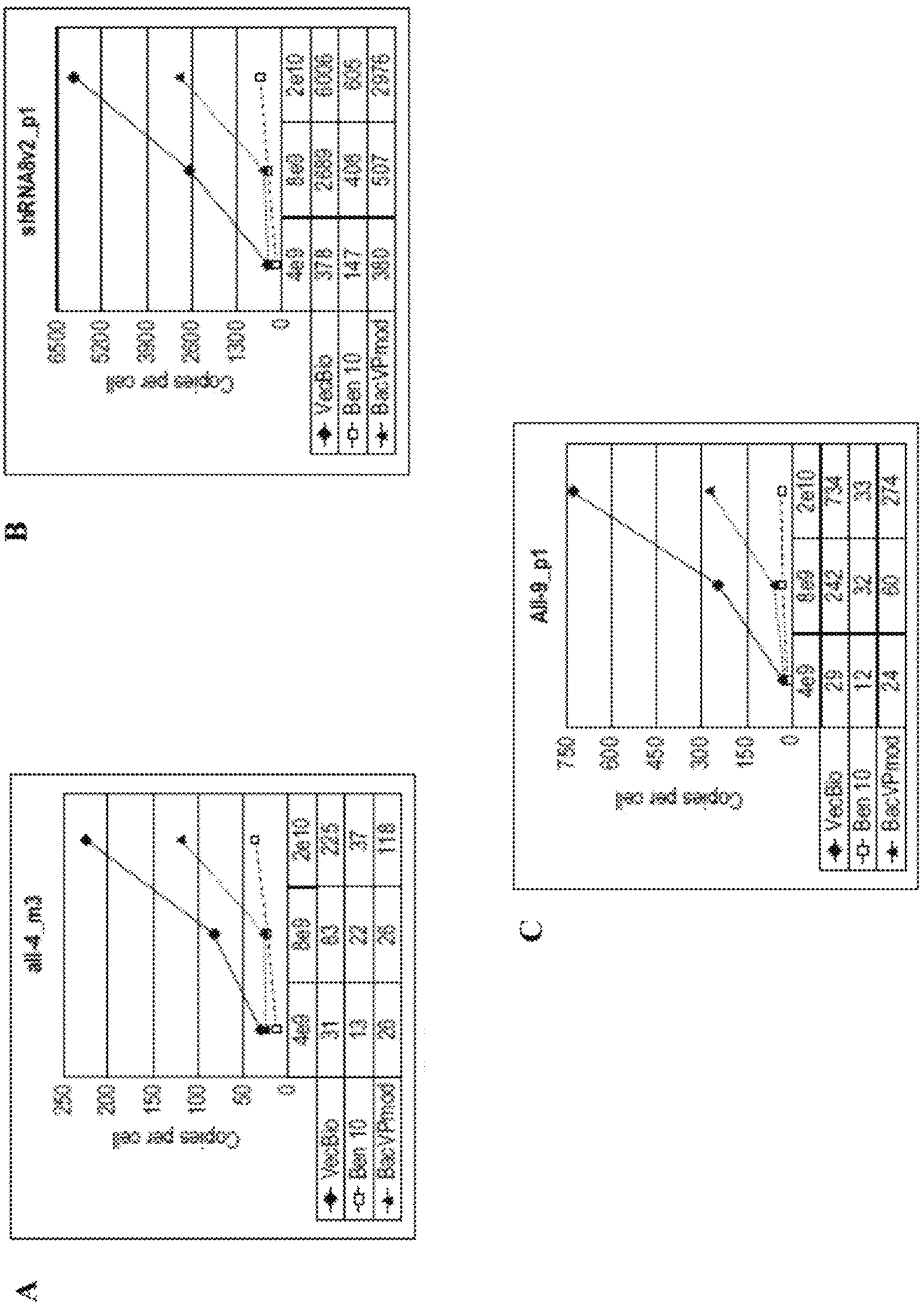
FIGS. 16A-16C show the total number of shmiR copies expressed per cell from JHU67 cells infected with 4×10e9, 8×10e9 and 1.6×10e10 AAV vector genomes of (i) AAV8 with unmodified VP1 produced in mammalian cells (VecBio), (ii) AAV8 with modified VP1 produced by baculovirus in insect cells (BacVPmod), and (iii) AAV8 with unmodified VP1 produced by baculovirus in insect cells (Ben10). AAV having the wildtype capsid produced in mammalian cells express high levels of shmiRs compared to AAV having the wildtype capsid produced in insect cells, where expression is nearly undetectable. AAV having the capsid with the modified VP1 produced in insect cells show a marked increase in expression, and therefore functionality, compared to AAV produced in insect using the unmodified wildtype capsid.

As shown in FIGS. 16A-16C, cells infected with AAV8 with unmodified wt VP1 prepared in mammalian cells produced readily detectable levels of shmiRs, whilst AAV8 with unmodified wt VP1 produced by baculovirus in insect cells produced little, if any, shmiRs. In contrast AAV8 with modified VP1 produced by baculovirus in insect cells produced relatively high levels of shmiRs, indicating an increase in functionality of these AAVs as compare to the AAV8 with unmodified wt VP1 produced by baculovirus in insect cells.

The biological activity was also assessed for (i) AAV9 with unmodified capsid protein produced in mammalian cells (Nationwide), and (ii) AAV9 with modified capsid protein using BACAAV9-Rep-VPmod (as described herein) produced by baculovirus in insect cells, each encoding 2 shmiRs targeting transcripts of human PABPN1 (designated sh13 and sh17). Briefly, C2C12 cells expressing the AAV internalization receptor were infected with 4×10e9, 8×10e9 and 1.6×10e10 vector genomes. Following a 72-hour incubation, cells were harvested, RNA extracted and shmiR expression quantified for the two shmiRs in accordance with the qPCR method described above.

Figure 17:
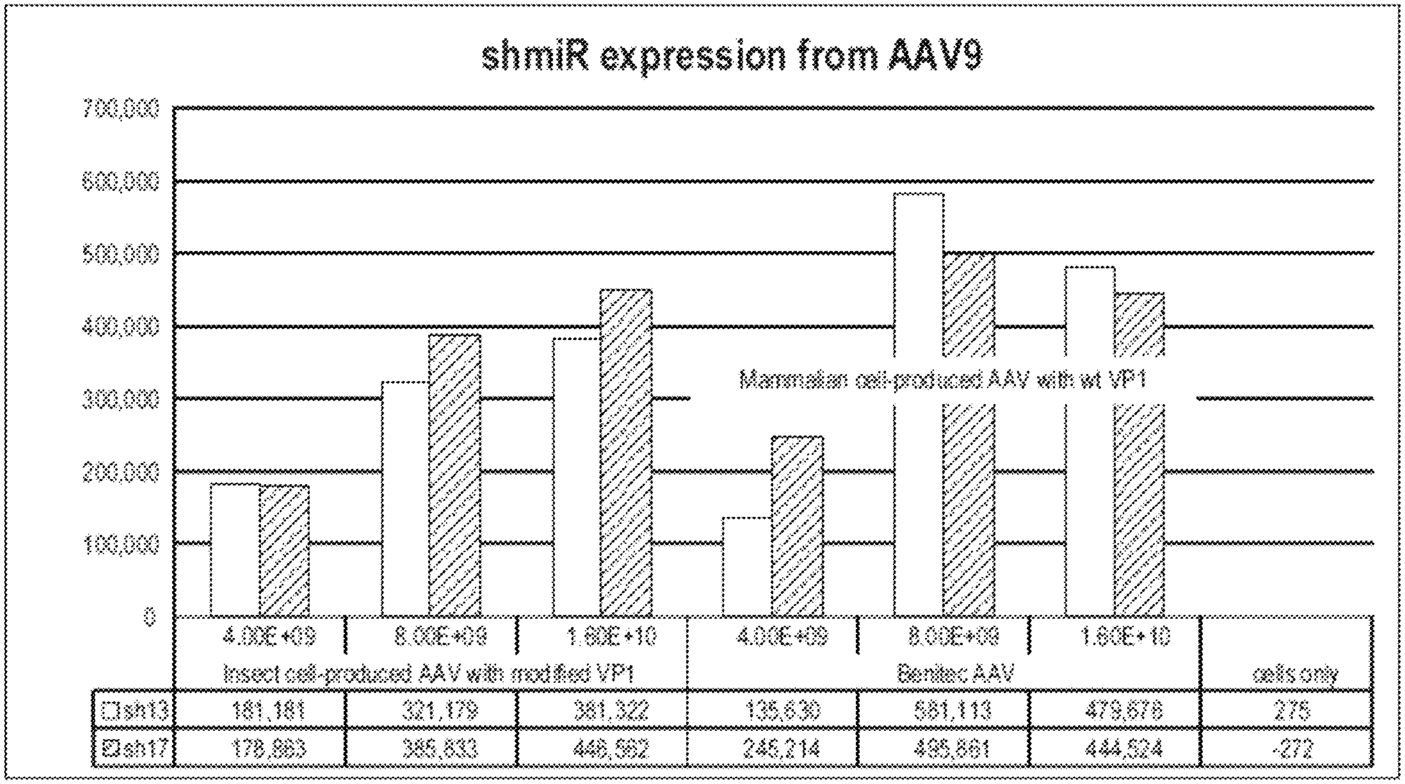
FIG. 17 shows the total number of shmiR copies expressed from C2C12 cells expressing the AAV Internalization Receptor (AAV-R) and infected with 4×10e9, 8×10e9 and 1.6×10e10 AAV vector genomes of (i) AAV9 with unmodified VP1 produced in mammalian cells, and (ii) AAV9 with modified VP1 produced by baculovirus in insect cells. Both recombinant viruses produced equivalent levels of shmiR, demonstrating equivalent functionality.

As shown in FIG. 17, the two preparations showed very similar levels of shmiR expression, indicating very similar viral functionality.

Although demonstrated in the context of AAV from serotypes 8 and 9, it is contemplated that modifying the VP1 subunit sequence of other AAV serotypes (other than serotype 2) in accordance with the approach described herein will restore functionality of AAV when produced from a baculovirus expression system in insect cells.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

We claim:

1. An adeno-associated virus (AAV) comprising:

(a) a viral capsid protein from AAV9 comprising a modified subunit 1 (VP1) sequence, wherein the modified VP1 sequence comprises any four or more of a serine at position 1, a glutamic acid at position 26, an arginine at position 40, an aspartic acid at position 43, a serine at position 44, and/or a lysine at position 64 relative to a corresponding wildtype AAV9 VP1 sequence set forth in SEQ ID NO: 87; and (b) a polynucleotide sequence comprising (i) a DNA-directed RNAi (ddRNAi) construct comprising a nucleic acid comprising a sequence which encodes a short hairpin micro-RNA (shmiR); and (ii) a PABPN1 construct comprising a nucleic acid comprising a sequence encoding a functional PABPN1 protein having a mRNA transcript which is not targeted by the shmiR(s) encoded by the ddRNAi construct.

2. The AAV of claim 1, wherein the modified VP1 sequence comprises a serine at position 1, a glutamic acid at position 26, an arginine at position 40, an aspartic acid at position 43, and a serine at position 44 relative to the wildtype AAV9 VP1 sequence set forth in SEQ ID NO: 87.

3. The AAV of claim 1, wherein the modified AAV9 VP1 sequence comprises the sequence set forth in SEQ ID NO: 88.

4. The AAV of claim 1, wherein the polynucleotide sequence at (b) comprises, in a 5' to 3' direction, the ddRNAi construct and the PABPN1 construct.

5. The AAV of claim 1, wherein the polynucleotide sequence at (b) comprises, in a 5' to 3' direction, the PABPN1 construct and the ddRNAi construct.

6. The AAV of claim 1, wherein the polynucleotide sequence at (b) comprises inverted terminal repeats (ITRs) from an AAV serotype and wherein the ITRs flank the sequence comprising the ddRNAi construct and PABPN1 construct, optionally wherein the ITRs are from an AAV2 serotype.

7. The AAV of claim 1, wherein:

the sequence encoding the functional PABPN1 protein is codon optimised such that its mRNA transcript is not targeted by the shmiRs of the ddRNAi construct; and/or the sequence encoding the functional PABPN1 protein is set forth in SEQ ID NO: 73.

8. The AAV of claim 1, wherein the ddRNAi construct and the sequence encoding the functional PABPN1 protein are operably-linked to a promoter positioned upstream of the ddRNAi construct and the sequence encoding the functional PABPN1 protein, optionally wherein the promoter is a muscle-specific promoter.

9. The AAV of claim 1, wherein the shmiR comprises:

an effector sequence of at least 17 nucleotides in length;

an effector complement sequence;

a stemloop sequence; and a primary micro RNA (pri-miRNA) backbone;

wherein the effector sequence is substantially complementary to a region of corresponding length in an RNA transcript set forth in any one of SEQ ID NOs: 1-13.

10. The AAV of claim 1, wherein the shmiR is selected from the group consisting of:

a shmiR comprising an effector sequence set forth in SEQ ID NO: 15 and an effector complement sequence set forth in SEQ ID NO: 14;

a shmiR comprising an effector sequence set forth in SEQ ID NO: 17 and an effector complement sequence set forth in SEQ ID NO: 16;

a shmiR comprising an effector sequence set forth in SEQ ID NO: 19 and an effector complement sequence set forth in SEQ ID NO: 18;

a shmiR comprising an effector sequence set forth in SEQ ID NO: 21 and an effector complement sequence set forth in SEQ ID NO: 20;

a shmiR comprising an effector sequence set forth in SEQ ID NO: 23 and an effector complement sequence set forth in SEQ ID NO: 22;

a shmiR comprising an effector sequence set forth in SEQ ID NO: 25 and an effector complement sequence set forth in SEQ ID NO: 24;

a shmiR comprising an effector sequence set forth in SEQ ID NO: 27 and an effector complement sequence set forth in SEQ ID NO: 26;

a shmiR comprising an effector sequence set forth in SEQ ID NO: 29 and an effector complement sequence set forth in SEQ ID NO: 28;

a shmiR comprising an effector sequence set forth in SEQ ID NO: 31 and an effector complement sequence set forth in SEQ ID NO: 30;

a shmiR comprising an effector sequence set forth in SEQ ID NO: 33 and an effector complement sequence set forth in SEQ ID NO: 32;

a shmiR comprising an effector sequence set forth in SEQ ID NO: 35 and an effector complement sequence set forth in SEQ ID NO: 34;

a shmiR comprising an effector sequence set forth in SEQ ID NO: 37 and an effector complement sequence set forth in SEQ ID NO: 36; and a shmiR comprising an effector sequence set forth in SEQ ID NO: 39 and an effector complement sequence set forth in SEQ ID NO: 38.

11. The AAV of claim 1, wherein the shmiR comprises, in a 5' to 3' direction:

(i) a 5' flanking sequence of the pri-miRNA backbone; the effector complement sequence; the stemloop sequence; the effector sequence; and a 3' flanking sequence of the pri-miRNA backbone; or (ii) a 5' flanking sequence of the pri-miRNA backbone; the effector sequence; the stemloop sequence; the effector complement sequence; and a 3' flanking sequence of the pri-miRNA backbone.

12. The AAV of claim 11, wherein:

(i) the stemloop sequence is the sequence set forth in SEQ ID NO: 40;

(ii) the pri-miRNA backbone is a pri-miR-30a backbone; and/or (iii) the 5' flanking sequence of the pri-miRNA backbone is set forth in SEQ ID NO: 41 and the 3' flanking sequence of the pri-miRNA backbone is set forth in SEQ ID NO: 42.

13. The AAV of claim 1, wherein the ddRNAi construct comprises at least two nucleic acids each encoding a shmiR, wherein each shmiR comprises an effector sequence which is substantially complementary to a RNA transcript corresponding to a PABPN1 protein which is causative of oculopharyngeal muscular dystrophy (OPMD), and wherein each shmiR comprises a different effector sequence.

14. The AAV of claim 1, wherein:

(i) the ddRNAi construct comprises at least two nucleic acids, each encoding a shmiR comprising an effector sequence which is substantially complementary to a region of corresponding length in an RNA transcript set forth in one of SEQ ID NOs: 1, 2, 4, 7, 9, 10 and 13;

(ii) the ddRNAi construct comprises at least two nucleic acids selected from the group consisting of:

a nucleic acid comprising or consisting of a DNA sequence encoding a shmiR comprising an effector sequence set forth in SEQ ID NO: 15 and an effector complement sequence set forth in SEQ ID NO: 14 (shmiR2);

a nucleic acid comprising or consisting of a DNA sequence encoding a shmiR comprising an effector sequence set forth in SEQ ID NO: 17 and an effector complement sequence set forth in SEQ ID NO: 16 (shmiR3);

a nucleic acid comprising or consisting of a DNA sequence encoding a shmiR comprising an effector sequence set forth in SEQ ID NO: 21 and an effector complement sequence set forth in SEQ ID NO: 20 (shmiR5);

a nucleic acid comprising or consisting of a DNA sequence encoding a shmiR comprising an effector sequence set forth in SEQ ID NO: 27 and an effector complement sequence set forth in SEQ ID NO: 26 (shmiR9);

a nucleic acid comprising or consisting of a DNA sequence encoding a shmiR comprising an effector sequence set forth in SEQ ID NO: 31 and an effector complement sequence set forth in SEQ ID NO: 30 (shmiR13);

a nucleic acid comprising or consisting of a DNA sequence encoding a shmiR comprising an effector sequence set forth in SEQ ID NO: 33 and an effector complement sequence set forth in SEQ ID NO: 32 (shmiR14); and a nucleic acid comprising or consisting of a DNA sequence encoding a shmiR comprising an effector sequence set forth in SEQ ID NO: 39 and an effector complement sequence set forth in SEQ ID NO: 38 (shmiR17); and/or (iii) the at least two nucleic acids are selected from the group consisting of:

a nucleic acid comprising or consisting of a DNA sequence set forth in SEQ ID NO: 56 (shmiR2);

a nucleic acid comprising or consisting of a DNA sequence set forth in SEQ ID NO: 57 (shmiR3);

a nucleic acid comprising or consisting of a DNA sequence set forth in SEQ ID NO: 59 (shmiR5);

a nucleic acid comprising or consisting of a DNA sequence set forth in SEQ ID NO: 62 (shmiR9);

a nucleic acid comprising or consisting of a DNA sequence set forth in SEQ ID NO: 64 (shmiR13);

a nucleic acid comprising or consisting of a DNA sequence set forth in SEQ ID NO: 65 (shmiR14); and a nucleic acid comprising or consisting of a DNA sequence set forth in SEQ ID NO: 68 (shmiR17).

15. The AAV of claim 14, wherein:

(i) the ddRNAi construct comprises at least two nucleic acids, each encoding a shmiR comprising an effector sequence which is substantially complementary to a region of corresponding length in an RNA transcript set forth in one of SEQ ID NOs: 2, 9, 10 and 13;

(ii) the ddRNAi construct comprises at least two nucleic acids selected from the group consisting of:

a nucleic acid comprising or consisting of a DNA sequence encoding a shmiR comprising an effector sequence set forth in SEQ ID NO: 17 and an effector complement sequence set forth in SEQ ID NO: 16 (shmiR3);

a nucleic acid comprising or consisting of a DNA sequence encoding a shmiR comprising an effector sequence set forth in SEQ ID NO: 31 and an effector complement sequence set forth in SEQ ID NO: 30 (shmiR13);

a nucleic acid comprising or consisting of a DNA sequence encoding a shmiR comprising an effector sequence set forth in SEQ ID NO: 33 and an effector complement sequence set forth in SEQ ID NO: 32 (shmiR14); and a nucleic acid comprising or consisting of a DNA sequence encoding a shmiR comprising an effector sequence set forth in SEQ ID NO: 39 and an effector complement sequence set forth in SEQ ID NO: 38 (shmiR17); and/or (iii) the ddRNAi construct comprises at least two nucleic acids, each selected from the group consisting of:

a nucleic acid comprising or consisting of a DNA sequence set forth in SEQ ID NO: 57 (shmiR3);

a nucleic acid comprising or consisting of a DNA sequence set forth in SEQ ID NO: 64 (shmiR13);

a nucleic acid comprising or consisting of a DNA sequence set forth in SEQ ID NO: 65 (shmiR14); and a nucleic acid comprising or consisting of a DNA sequence set forth in SEQ ID NO: 68 (shmiR17).

16. The AAV of claim 1, wherein said ddRNAi construct comprises:

(a) a nucleic acid comprising or consisting of a DNA sequence encoding a shmiR comprising an effector sequence set forth in SEQ ID NO: 31 and an effector complement sequence set forth in SEQ ID NO: 30 (shmiR13); and a nucleic acid comprising or consisting of a DNA sequence encoding a shmiR comprising an effector sequence set forth in SEQ ID NO: 39 and an effector complement sequence set forth in SEQ ID NO: 38 (shmiR17); and/or (b) a nucleic acid comprising or consisting of the DNA sequence set forth in SEQ ID NO: 64 (shmiR13); and a nucleic acid comprising or consisting of the DNA sequence set forth in SEQ ID NO: 68 (shmiR17).

17. A pharmaceutical composition comprising the AAV of claim 1 and one or more pharmaceutically acceptable carriers.

18. A method for treating a subject suffering from oculopharyngeal muscular dystrophy (OPMD) comprising administering to said subject the AAV of claim 1 or a pharmaceutical composition comprising the AAV of claim 1.

19. The method of claim 18, wherein the composition is administered by direct injection to a pharyngeal muscle of the subject.

20. The method of claim 19, wherein the pharyngeal muscle comprises one or more of an inferior constrictor muscle, a middle constrictor muscle, a superior constrictor muscle, a palatopharyngeus muscle, a salpingopharyngeus muscle, a stylopharyngeus muscle, or any combination thereof.

21. The AAV of claim 1, wherein the modified VP1 sequence comprises a glutamic acid at position 26, an arginine at position 40, an aspartic acid at position 43, and a serine at position 44 relative to the wildtype AAV9 VP1 sequence set forth in SEQ ID NO: 87.

22. The AAV of claim 21, wherein the modified VP1 sequence comprises the amino acid sequence set forth in SEQ ID NO: 87, with the exception of amino acid substitutions A26E, Q40R, K43D, and A44S relative to the amino acid sequence set forth in SEQ ID NO: 87.

23. An adeno-associated virus (AAV) comprising:

(a) a viral capsid protein from AAV9 comprising a modified subunit 1 (VP1) sequence comprising any four or more of a serine at position 1, a glutamic acid at position 26, an arginine at position 40, an aspartic acid at position 43, a serine at position 44, and/or a lysine at position 64 relative to a corresponding wildtype AAV9 VP1 sequence set forth in SEQ ID NO: 87; and (b) a polynucleotide sequence comprising: (i) a DNA-directed RNAi (ddRNAi) construct comprising: a nucleic acid comprising or consisting of a DNA sequence encoding a short hairpin micro-RNA (shmiR) comprising an effector sequence set forth in SEQ ID NO: 31 and an effector complement sequence set forth in SEQ ID NO: 30 (shmiR13); and a nucleic acid comprising or consisting of a DNA sequence encoding a shmiR comprising an effector sequence set forth in SEQ ID NO: 39 and an effector complement sequence set forth in SEQ ID NO: 38 (shmiR17); and (ii) a PABPN1 construct comprising a nucleic acid comprising a sequence encoding a functional PABPN1 protein, the sequence encoding the functional PABPN1 protein is codon optimized such that its mRNA transcript is not targeted by the shmiRs of the ddRNAi construct.

24. The AAV of claim 23, wherein:

(a) the ddRNAi construct comprises a nucleic acid comprising or consisting of the DNA sequence set forth in SEQ ID NO: 64 (shmiR13), and a nucleic acid comprising or consisting of the DNA sequence set forth in SEQ ID NO: 68 (shmiR17); and/or (b) the sequence encoding the functional PABPN1 protein is set forth in SEQ ID NO: 73.

25. The AAV of claim 23, wherein the modified VP1 sequence comprises a glutamic acid at position 26, an arginine at position 40, an aspartic acid at position 43, and a serine at position 44 relative to the wildtype AAV9 VP1 sequence set forth in SEQ ID NO: 87.

26. The AAV of claim 23, wherein the modified VP1 sequence comprises the amino acid sequence set forth in SEQ ID NO: 87, with the exception of amino acid substitutions A26E, Q40R, K43D, and A44S relative to the amino acid sequence set forth in SEQ ID NO: 87.

* * * * *

SEQUENCE LISTING

<160> NUMBER OF SEQ ID NOS: 98

<210> SEQ ID NO 1
<211> LENGTH: 28
<212> TYPE: RNA
<213> ORGANISM: Homo sapiens

<400> SEQUENCE: 1
gagaagcaga ugaauaugag uccaccuc 28

<210> SEQ ID NO 2
<211> LENGTH: 28
<212> TYPE: RNA
<213> ORGANISM: Homo sapiens

<400> SEQUENCE: 2
gaacgaggua gagaagcaga ugaauaug 28

<210> SEQ ID NO 3
<211> LENGTH: 28
<212> TYPE: RNA
<213> ORGANISM: Homo sapiens

<400> SEQUENCE: 3
gaagcugaga agcuaaagga gcuacaga 28

<210> SEQ ID NO 4
<211> LENGTH: 28
<212> TYPE: RNA
<213> ORGANISM: Homo sapiens

<400> SEQUENCE: 4
gggcuagagc gacaucaugg uauucccc 28

<210> SEQ ID NO 5
<211> LENGTH: 28
<212> TYPE: RNA
<213> ORGANISM: Homo sapiens

<400> SEQUENCE: 5
cugugugaca aauuuagugg ccauccca 28

<210> SEQ ID NO 6
<211> LENGTH: 28
<212> TYPE: RNA
<213> ORGANISM: Homo sapiens

<400> SEQUENCE: 6
gacuauggug caacagcaga agagcugg 28

<210> SEQ ID NO 7
<211> LENGTH: 28
<212> TYPE: RNA
<213> ORGANISM: Homo sapiens

<400> SEQUENCE: 7
cgagguagag aagcagauga auaugagu 28

<210> SEQ ID NO 8
<211> LENGTH: 28
<212> TYPE: RNA
<213> ORGANISM: Homo sapiens

<400> SEQUENCE: 8
cagugguuuu aacagcaggc cccggggu 28

<210> SEQ ID NO 9
<211> LENGTH: 28
<212> TYPE: RNA
<213> ORGANISM: Homo sapiens

<400> SEQUENCE: 9
agagcgacau caugguauuc cccuuacu 28

<210> SEQ ID NO 10
<211> LENGTH: 28
<212> TYPE: RNA
<213> ORGANISM: Homo sapiens

<400> SEQUENCE: 10
gguagagaag cagaugaaua ugagucca 28

<210> SEQ ID NO 11
<211> LENGTH: 28
<212> TYPE: RNA
<213> ORGANISM: Homo sapiens

<400> SEQUENCE: 11
auugaggaga agauggaggc ugaugccc 28

<210> SEQ ID NO 12
<211> LENGTH: 28
<212> TYPE: RNA
<213> ORGANISM: Homo sapiens

<400> SEQUENCE: 12
ggaggaagaa gcugagaagc uaaaggag 28

<210> SEQ ID NO 13
<211> LENGTH: 28
<212> TYPE: RNA
<213> ORGANISM: Homo sapiens

<400> SEQUENCE: 13
aacgagguag agaagcagau gaauauga 28

<210> SEQ ID NO 14
<211> LENGTH: 20
<212> TYPE: RNA
<213> ORGANISM: Artificial sequence
<220> FEATURE:
<223> OTHER INFORMATION: Effector sequence for shmiR2

<400> SEQUENCE: 14
agcagaugaa uaugagucca 20

<210> SEQ ID NO 15
<211> LENGTH: 21
<212> TYPE: RNA
<213> ORGANISM: Artificial sequence
<220> FEATURE:
<223> OTHER INFORMATION: Effector complement sequence for shmiR2

<400> SEQUENCE: 15
uggacucaua uucaucugcu u 21

<210> SEQ ID NO 16
<211> LENGTH: 20
<212> TYPE: RNA
<213> ORGANISM: Artificial sequence
<220> FEATURE:
<223> OTHER INFORMATION: Effector sequence for shmiR3

<400> SEQUENCE: 16
gagguagaga agcagaugaa 20

<210> SEQ ID NO 17
<211> LENGTH: 21
<212> TYPE: RNA
<213> ORGANISM: Artificial sequence
<220> FEATURE:
<223> OTHER INFORMATION: Effector complement sequence for shmiR3

<400> SEQUENCE: 17
uucaucugcu ucucuaccuc g 21

<210> SEQ ID NO 18
<211> LENGTH: 20
<212> TYPE: RNA
<213> ORGANISM: Artificial sequence
<220> FEATURE:
<223> OTHER INFORMATION: Effector sequence for shmiR4

<400> SEQUENCE: 18
cugagaagcu aaaggagcua 20

<210> SEQ ID NO 19
<211> LENGTH: 21
<212> TYPE: RNA
<213> ORGANISM: Artificial sequence
<220> FEATURE:
<223> OTHER INFORMATION: Effector complement sequence for shmiR4

<400> SEQUENCE: 19
uagcuccuuu agcuucucag c 21

<210> SEQ ID NO 20
<211> LENGTH: 20
<212> TYPE: RNA
<213> ORGANISM: Artificial sequence
<220> FEATURE:
<223> OTHER INFORMATION: Effector sequence for shmiR5

<400> SEQUENCE: 20
uagagcgaca ucaugguauu 20

<210> SEQ ID NO 21

<211> LENGTH: 21
<212> TYPE: RNA
<213> ORGANISM: Artificial sequence
<220> FEATURE:
<223> OTHER INFORMATION: Effector complement sequence for shmiR5

<400> SEQUENCE: 21
aauaccauga ugucgcucua g 21

<210> SEQ ID NO 22
<211> LENGTH: 20
<212> TYPE: RNA
<213> ORGANISM: Artificial sequence
<220> FEATURE:
<223> OTHER INFORMATION: Effector sequence for shmiR6

<400> SEQUENCE: 22
gugacaaauu uaguggccau 20

<210> SEQ ID NO 23
<211> LENGTH: 21
<212> TYPE: RNA
<213> ORGANISM: Artificial sequence
<220> FEATURE:
<223> OTHER INFORMATION: Effector complement sequence for shmiR6

<400> SEQUENCE: 23
auggccacua aauuugucac a 21

<210> SEQ ID NO 24
<211> LENGTH: 20
<212> TYPE: RNA
<213> ORGANISM: Artificial sequence
<220> FEATURE:
<223> OTHER INFORMATION: Effector sequence for shmiR7

<400> SEQUENCE: 24
auggugcaac agcagaagag 20

<210> SEQ ID NO 25
<211> LENGTH: 21
<212> TYPE: RNA
<213> ORGANISM: Artificial sequence
<220> FEATURE:
<223> OTHER INFORMATION: Effector complement sequence for shmiR7

<400> SEQUENCE: 25
cucuucugcu guugcaccau a 21

<210> SEQ ID NO 26
<211> LENGTH: 20
<212> TYPE: RNA
<213> ORGANISM: Artificial sequence
<220> FEATURE:
<223> OTHER INFORMATION: Effector sequence for shmiR9

<400> SEQUENCE: 26
guagagaagc agaugaauau 20

<210> SEQ ID NO 27
<211> LENGTH: 21
<212> TYPE: RNA
<213> ORGANISM: Artificial sequence
<220> FEATURE:
<223> OTHER INFORMATION: Effector complement sequence for shmiR9

<400> SEQUENCE: 27
auauucaucu gcuucucuac c 21

<210> SEQ ID NO 28
<211> LENGTH: 20
<212> TYPE: RNA
<213> ORGANISM: Artificial sequence
<220> FEATURE:
<223> OTHER INFORMATION: Effector sequence for shmiR11

<400> SEQUENCE: 28
gguuuuaaca gcaggccccg 20

<210> SEQ ID NO 29
<211> LENGTH: 21
<212> TYPE: RNA
<213> ORGANISM: Artificial sequence
<220> FEATURE:
<223> OTHER INFORMATION: Effector complement sequence for shmiR11

<400> SEQUENCE: 29
cggggccugc uguuaaaacc a 21

<210> SEQ ID NO 30
<211> LENGTH: 20
<212> TYPE: RNA
<213> ORGANISM: Artificial sequence
<220> FEATURE:
<223> OTHER INFORMATION: Effector sequence for shmiR13

<400> SEQUENCE: 30
cgacaucaug guauuccccu 20

<210> SEQ ID NO 31
<211> LENGTH: 21
<212> TYPE: RNA
<213> ORGANISM: Artificial sequence
<220> FEATURE:
<223> OTHER INFORMATION: Effector complement sequence for shmiR13

<400> SEQUENCE: 31
aggggaauac caugaugucg c 21

<210> SEQ ID NO 32
<211> LENGTH: 20
<212> TYPE: RNA
<213> ORGANISM: Artificial sequence
<220> FEATURE:
<223> OTHER INFORMATION: Effector sequence for shmiR14

<400> SEQUENCE: 32
gagaagcaga ugaauaugag 20

<210> SEQ ID NO 33
<211> LENGTH: 21
<212> TYPE: RNA
<213> ORGANISM: Artificial sequence
<220> FEATURE:
<223> OTHER INFORMATION: Effector complement sequence for shmiR14

<400> SEQUENCE: 33
cucauauuca ucugcuucuc u 21

<210> SEQ ID NO 34
<211> LENGTH: 20
<212> TYPE: RNA

<213> ORGANISM: Artificial sequence
<220> FEATURE:
<223> OTHER INFORMATION: Effector sequence for shmiR15

<400> SEQUENCE: 34
aggagaagau ggaggcugau 20

<210> SEQ ID NO 35
<211> LENGTH: 21
<212> TYPE: RNA
<213> ORGANISM: Artificial sequence
<220> FEATURE:
<223> OTHER INFORMATION: Effector complement sequence for shmiR15

<400> SEQUENCE: 35
aucagccucc aucuucuccu c 21

<210> SEQ ID NO 36
<211> LENGTH: 20
<212> TYPE: RNA
<213> ORGANISM: Artificial sequence
<220> FEATURE:
<223> OTHER INFORMATION: Effector sequence for shmiR16

<400> SEQUENCE: 36
gaagaagcug agaagcuaaa 20

<210> SEQ ID NO 37
<211> LENGTH: 21
<212> TYPE: RNA
<213> ORGANISM: Artificial sequence
<220> FEATURE:
<223> OTHER INFORMATION: Effector complement sequence for shmiR16

<400> SEQUENCE: 37
uuuagcuucu cagcuucuuc c 21

<210> SEQ ID NO 38
<211> LENGTH: 20
<212> TYPE: RNA
<213> ORGANISM: Artificial sequence
<220> FEATURE:
<223> OTHER INFORMATION: Effector sequence for shmiR17

<400> SEQUENCE: 38
agguagagaa gcagaugaau 20

<210> SEQ ID NO 39
<211> LENGTH: 21
<212> TYPE: RNA
<213> ORGANISM: Artificial sequence
<220> FEATURE:
<223> OTHER INFORMATION: Effector complement sequence for shmiR17

<400> SEQUENCE: 39
auucaucugc uucucuaccu c 21

<210> SEQ ID NO 40
<211> LENGTH: 18
<212> TYPE: RNA
<213> ORGANISM: Artificial sequence
<220> FEATURE:
<223> OTHER INFORMATION: Stem loop

<400> SEQUENCE: 40
acugugaagc agaugggu 18

<210> SEQ ID NO 41
<211> LENGTH: 26
<212> TYPE: RNA
<213> ORGANISM: Artificial sequence
<220> FEATURE:
<223> OTHER INFORMATION: 5' flanking sequence of the pri-miRNA backbone
<220> FEATURE:
<221> NAME/KEY: misc_feature
<222> LOCATION: (26)..(26)
<223> OTHER INFORMATION: n is u or a

<400> SEQUENCE: 41
gguauauugc uguugacagu gagcgn 26

<210> SEQ ID NO 42
<211> LENGTH: 22
<212> TYPE: RNA
<213> ORGANISM: Artificial sequence
<220> FEATURE:
<223> OTHER INFORMATION: 3' flanking sequence of the pri-miRNA backbone

<400> SEQUENCE: 42
cgccuacugc cucggacuuc aa 22

<210> SEQ ID NO 43
<211> LENGTH: 107
<212> TYPE: RNA
<213> ORGANISM: Artificial sequence
<220> FEATURE:
<223> OTHER INFORMATION: RNA sequence encoding shmiR2

<400> SEQUENCE: 43
gguauauugc uguugacagu gagcguagca gaugaauaug aguccaacug ugaagcagau 60
ggguuggacu cauauucauc ugcuucgccu acugccucgg acuucaa 107

<210> SEQ ID NO 44
<211> LENGTH: 107
<212> TYPE: RNA
<213> ORGANISM: Artificial sequence
<220> FEATURE:
<223> OTHER INFORMATION: RNA sequence encoding shmiR3

<400> SEQUENCE: 44
gguauauugc uguugacagu gagcgagagg uagagaagca gaugaaacug ugaagcagau 60
ggguuucauc ugcuucucua ccucgcgccu acugccucgg acuucaa 107

<210> SEQ ID NO 45
<211> LENGTH: 107
<212> TYPE: RNA
<213> ORGANISM: Artificial sequence
<220> FEATURE:
<223> OTHER INFORMATION: RNA sequence encoding shmiR4

<400> SEQUENCE: 45
gguauauugc uguugacagu gagcgacuga gaagcuaaag gagcuaacug ugaagcagau 60
ggguuagcuc cuuuagcuuc ucagccgccu acugccucgg acuucaa 107

<210> SEQ ID NO 46
<211> LENGTH: 107
<212> TYPE: RNA
<213> ORGANISM: Artificial sequence
<220> FEATURE:
<223> OTHER INFORMATION: RNA sequence encoding shmiR5

<400> SEQUENCE: 46
gguauauugc uguugacagu gagcgauaga gcgacaucau gguauuacug ugaagcagau 60
ggguaauacc augaugucgc ucuagcgccu acugccucgg acuucaa 107

<210> SEQ ID NO 47
<211> LENGTH: 107
<212> TYPE: RNA
<213> ORGANISM: Artificial sequence
<220> FEATURE:
<223> OTHER INFORMATION: RNA sequence encoding shmiR6

<400> SEQUENCE: 47
gguauauugc uguugacagu gagcgaguga caaauuuagu ggccauacug ugaagcagau 60
ggguauggcc acuaaauuug ucacacgccu acugccucgg acuucaa 107

<210> SEQ ID NO 48
<211> LENGTH: 107
<212> TYPE: RNA
<213> ORGANISM: Artificial sequence
<220> FEATURE:
<223> OTHER INFORMATION: RNA sequence encoding shmiR7

<400> SEQUENCE: 48
gguauauugc uguugacagu gagcgaaugg ugcaacagca gaagagacug ugaagcagau 60
gggucucuuc ugcuguugca ccauacgccu acugccucgg acuucaa 107

<210> SEQ ID NO 49
<211> LENGTH: 107
<212> TYPE: RNA
<213> ORGANISM: Artificial sequence
<220> FEATURE:
<223> OTHER INFORMATION: RNA sequence encoding shmiR9

<400> SEQUENCE: 49
gguauauugc uguugacagu gagcgaguag agaagcagau gaauauacug ugaagcagau 60
ggguauauuc aucugcuucu cuacccgccu acugccucgg acuucaa 107

<210> SEQ ID NO 50
<211> LENGTH: 107
<212> TYPE: RNA
<213> ORGANISM: Artificial sequence
<220> FEATURE:
<223> OTHER INFORMATION: RNA sequence encoding shmiR11

<400> SEQUENCE: 50
gguauauugc uguugacagu gagcgagguu uuaacagcag gccccgacug ugaagcagau 60
gggucggggc cugcuguuaa aaccacgccu acugccucgg acuucaa 107

<210> SEQ ID NO 51
<211> LENGTH: 107
<212> TYPE: RNA
<213> ORGANISM: Artificial sequence
<220> FEATURE:
<223> OTHER INFORMATION: RNA sequence encoding shmiR13

<400> SEQUENCE: 51
gguauauugc uguugacagu gagcgacgac aucaugguau uccccuacug ugaagcagau 60
ggguagggga auaccaugau gucgccgccu acugccucgg acuucaa 107

<210> SEQ ID NO 52
<211> LENGTH: 107

<212> TYPE: RNA
<213> ORGANISM: Artificial sequence
<220> FEATURE:
<223> OTHER INFORMATION: RNA sequence encoding shmiR14

<400> SEQUENCE: 52
gguauauugc uguugacagu gagcgugaga agcagaugaa uaugagacug ugaagcagau 60
gggucucaua uucaucugcu ucucucgccu acugccucgg acuucaa 107

<210> SEQ ID NO 53
<211> LENGTH: 107
<212> TYPE: RNA
<213> ORGANISM: Artificial sequence
<220> FEATURE:
<223> OTHER INFORMATION: RNA sequence encoding shmiR15

<400> SEQUENCE: 53
gguauauugc uguugacagu gagcgaagga gaagauggag gcugauacug ugaagcagau 60
ggguaucagc cuccaucuuc uccuccgccu acugccucgg acuucaa 107

<210> SEQ ID NO 54
<211> LENGTH: 107
<212> TYPE: RNA
<213> ORGANISM: Artificial sequence
<220> FEATURE:
<223> OTHER INFORMATION: RNA sequence encoding shmiR16

<400> SEQUENCE: 54
gguauauugc uguugacagu gagcgagaag aagcugagaa gcuaaaacug ugaagcagau 60
ggguuuuagc uucucagcuu cuucccgccu acugccucgg acuucaa 107

<210> SEQ ID NO 55
<211> LENGTH: 107
<212> TYPE: RNA
<213> ORGANISM: Artificial sequence
<220> FEATURE:
<223> OTHER INFORMATION: RNA sequence encoding shmiR17

<400> SEQUENCE: 55
gguauauugc uguugacagu gagcgaaggu agagaagcag augaauacug ugaagcagau 60
ggguauucau cugcuucucu accuccgccu acugccucgg acuucaa 107

<210> SEQ ID NO 56
<211> LENGTH: 107
<212> TYPE: DNA
<213> ORGANISM: Artificial sequence
<220> FEATURE:
<223> OTHER INFORMATION: DNA sequence encoding shmiR2

<400> SEQUENCE: 56
ggtatattgc tgttgacagt gagcgtagca gatgaatatg agtccaactg tgaagcagat 60
gggttggact catattcatc tgcttcgcct actgcctcgg acttcaa 107

<210> SEQ ID NO 57
<211> LENGTH: 107
<212> TYPE: DNA
<213> ORGANISM: Artificial sequence
<220> FEATURE:
<223> OTHER INFORMATION: DNA sequence encoding shmiR3

<400> SEQUENCE: 57
ggtatattgc tgttgacagt gagcgagagg tagagaagca gatgaaactg tgaagcagat 60
gggtttcatc tgcttctcta cctcgcgcct actgcctcgg acttcaa 107

<210> SEQ ID NO 58
<211> LENGTH: 107
<212> TYPE: DNA
<213> ORGANISM: Artificial sequence
<220> FEATURE:
<223> OTHER INFORMATION: DNA sequence encoding shmiR4

<400> SEQUENCE: 58
ggtatattgc tgttgacagt gagcgactga gaagctaaag gagctaactg tgaagcagat 60
gggttagctc ctttagcttc tcagccgcct actgcctcgg acttcaa 107

<210> SEQ ID NO 59
<211> LENGTH: 107
<212> TYPE: DNA
<213> ORGANISM: Artificial sequence
<220> FEATURE:
<223> OTHER INFORMATION: DNA sequence encoding shmiR5

<400> SEQUENCE: 59
ggtatattgc tgttgacagt gagcgataga gcgacatcat ggtattactg tgaagcagat 60
gggtaatacc atgatgtcgc tctagcgcct actgcctcgg acttcaa 107

<210> SEQ ID NO 60
<211> LENGTH: 107
<212> TYPE: DNA
<213> ORGANISM: Artificial sequence
<220> FEATURE:
<223> OTHER INFORMATION: DNA sequence encoding shmiR6

<400> SEQUENCE: 60
ggtatattgc tgttgacagt gagcgagtga caaatttagt ggccatactg tgaagcagat 60
gggtatggcc actaaatttg tcacacgcct actgcctcgg acttcaa 107

<210> SEQ ID NO 61
<211> LENGTH: 107
<212> TYPE: DNA
<213> ORGANISM: Artificial sequence
<220> FEATURE:
<223> OTHER INFORMATION: DNA sequence encoding shmiR7

<400> SEQUENCE: 61
ggtatattgc tgttgacagt gagcgaatgg tgcaacagca gaagagactg tgaagcagat 60
gggtctcttc tgctgttgca ccatacgcct actgcctcgg acttcaa 107

<210> SEQ ID NO 62
<211> LENGTH: 107
<212> TYPE: DNA
<213> ORGANISM: Artificial sequence
<220> FEATURE:
<223> OTHER INFORMATION: DNA sequence encoding shmiR9

<400> SEQUENCE: 62
ggtatattgc tgttgacagt gagcgagtag agaagcagat gaatatactg tgaagcagat 60
gggtatattc atctgcttct ctacccgcct actgcctcgg acttcaa 107

<210> SEQ ID NO 63
<211> LENGTH: 107
<212> TYPE: DNA
<213> ORGANISM: Artificial sequence
<220> FEATURE:
<223> OTHER INFORMATION: DNA sequence encoding shmiR11

<400> SEQUENCE: 63
ggtatattgc tgttgacagt gagcgaggtt ttaacagcag gccccgactg tgaagcagat 60
gggtcggggc ctgctgttaa aaccacgcct actgcctcgg acttcaa 107

<210> SEQ ID NO 64
<211> LENGTH: 107
<212> TYPE: DNA
<213> ORGANISM: Artificial sequence
<220> FEATURE:
<223> OTHER INFORMATION: DNA sequence encoding shmiR13

<400> SEQUENCE: 64
ggtatattgc tgttgacagt gagcgacgac atcatggtat tcccctactg tgaagcagat 60
gggtagggga ataccatgat gtcgccgcct actgcctcgg acttcaa 107

<210> SEQ ID NO 65
<211> LENGTH: 107
<212> TYPE: DNA
<213> ORGANISM: Artificial sequence
<220> FEATURE:
<223> OTHER INFORMATION: DNA sequence encoding shmiR14

<400> SEQUENCE: 65
ggtatattgc tgttgacagt gagcgtgaga agcagatgaa tatgagactg tgaagcagat 60
gggtctcata ttcatctgct tctctcgcct actgcctcgg acttcaa 107

<210> SEQ ID NO 66
<211> LENGTH: 107
<212> TYPE: DNA
<213> ORGANISM: Artificial sequence
<220> FEATURE:
<223> OTHER INFORMATION: DNA sequence encoding shmiR15

<400> SEQUENCE: 66
ggtatattgc tgttgacagt gagcgaagga gaagatggag gctgatactg tgaagcagat 60
gggtatcagc ctccatcttc tcctccgcct actgcctcgg acttcaa 107

<210> SEQ ID NO 67
<211> LENGTH: 107
<212> TYPE: DNA
<213> ORGANISM: Artificial sequence
<220> FEATURE:
<223> OTHER INFORMATION: DNA sequence encoding shmiR16

<400> SEQUENCE: 67
ggtatattgc tgttgacagt gagcgagaag aagctgagaa gctaaaactg tgaagcagat 60
gggttttagc ttctcagctt cttcccgcct actgcctcgg acttcaa 107

<210> SEQ ID NO 68
<211> LENGTH: 107
<212> TYPE: DNA
<213> ORGANISM: Artificial sequence
<220> FEATURE:
<223> OTHER INFORMATION: DNA sequence encoding shmiR17

<400> SEQUENCE: 68
ggtatattgc tgttgacagt gagcgaaggt agagaagcag atgaatactg tgaagcagat 60
gggtattcat ctgcttctct acctccgcct actgcctcgg acttcaa 107

<210> SEQ ID NO 69

<211> LENGTH: 2532
<212> TYPE: DNA
<213> ORGANISM: Artificial sequence
<220> FEATURE:
<223> OTHER INFORMATION: Double expression construct version 1 coding
for shmiR3, shmiR14 and codon optimized PABPN1

<400> SEQUENCE: 69
cgatcgcgcg cagatctgtc atgatgatcc tagcatgctg cccatgtaag gaggcaaggc 60
ctggggacac ccgagatgcc tggttataat taacccagac atgtggctgc cccccccccc 120
ccaacacctg ctgcctctaa aaataaccct gcatgccatg ttcccggcga agggccagct 180
gtcccccgcc agctagactc agcacttagt ttaggaacca gtgagcaagt cagcccttgg 240
ggcagcccat acaaggccat ggggctgggc aagctgcacg cctgggtccg ggtgggcac 300 ggtgcccggg caacgagctg aaagctcatc tgctctcagg ggcccctccc tggggacagc 360
ccctcctggc tagtcacacc ctgtaggctc ctctatataa cccaggggca caggggctgc 420
cctcattcta ccaccacctc cacagcacag acagacactc aggagccagc cagcgtcgat 480
cattgaagtt actattccga agttcctatt ctctagaatt cgccaccacg cgtggtatat 540
tgctgttgac agtgagcgag aggtagagaa gcagatgaaa ctgtgaagca gatgggtttc 600
atctgcttct ctacctcgcg cctactgcct cggacttcaa atcatctact ccatggccct 660
ctgcgtttgc tgaagacaga accgcaaagc aggacccgac aggattctcc ccgcctcttc 720
agagactatg tttacaagat atcggtatat tgctgttgac agtgagcgtg agaagcagat 780
gaatatgaga ctgtgaagca gatgggtctc atattcatct gcttctctcg cctactgcct 840
cggacttcaa gtcgacgcta gcaataaagg atcctttatt ttcattggat ccgtgtgttg 900 gtttttgtg tgcggttaat taaggtaccc gagctccacc gcggtggcgg ccgtccgccc 960
tcggcaccat cctcacgaca cccaaatatg gcgacgggtg aggaatggtg gggagttatt 1020
tttagagcgg tgaggaaggt gggcaggcag caggtgttgg cgctctaaaa ataactcccg 1080
ggagttattt ttagagcgga ggaatggtgg acacccaaat atggcgacgg ttcctcaccc 1140
gtcgccatat ttgggtgtcc gccctcggcc ggggccgcat tcctgggggc cgggcggtgc 1200
tcccgcccgc ctcgataaaa ggctccgggg ccggcggcgg cccacgagct acccggagga 1260
gcgggaggcg ccaagctcta gaactagtgg atcccccggg ctgcaggaat tcgatgccac 1320
catggccgct gccgccgctg ctgctgccgc agccggcgct gccggcggaa gaggcagcgg 1380
ccctggcaga cggcggcatc tggtccctgg cgccggaggg gaggccggcg aaggcgcccc 1440
tggcggagcc ggcgactacg gcaacggcct ggaaagcgag gaactggaac ccgaggaact 1500
gctgctggaa cctgagcccg agccagagcc cgaggaagag cccccctaggc caagagcccc 1560 ccctggcgcc ccaggaccag gaccaggctc tggggcacca ggctctcagg aagaggaaga 1620
agagcccggc ctcgtcgagg gagacccagg cgatggcgct atcgaagatc ccgagctgga 1680
agccatcaag gccagagtgc gggagatgga agaggaggcc gaaaaattga aagagctgca 1740
gaacgaagtc gaaaaacaaa tgaacatgtc ccccccctcct ggaaatgctg gccctgtgat 1800
catgagcatc gaggaaaaga tggaagccga cgcccggtct atctacgtgg gcaacgtgga 1860
ctacggcgcc accgccgaag aactggaagc ccactttcac ggctgtggca gcgtgaaccg 1920
ggtgaccatc ctgtgcgaca agttcagcgg ccaccccaag ggcttcgcct acatcgagtt 1980
cagcgacaaa gaaagcgtgc ggacctctct ggctctcgac gagtctctgt tcaggggaag 2040
gcagatcaag gtcatcccca agcggaccaa caggcccggc atcagcacca ccgacagagg 2100

```
cttccctagg gctaggtaca gagcccggac caccaactac aacagcagca gaagccggtt   2160

ctacagcggc ttcaattctc ggcctagagg cagagtgtac cggggcaggg ccagggccac   2220

ctcctggtac agcccctacg aacagaagct gatcagcgag gaagatctgt gatgagatat   2280

ctgatgacat atgacgcgtt taattaactg tgccttctag ttgccagcca tctgttgttt   2340

gcccctcccc cgtgccttcc ttgaccctgg aaggtgccac tcccactgtc ctttcctaat   2400

aaaatgagga aattgcatcg cattgtctga gtaggtgtca ttctattctg gggggtgggg   2460

tggggcagga cagcaagggg gaggattggg aagacaatag caggcatgct ggggatgcgg   2520

tgggctctat gg                                                       2532
```

<210> SEQ ID NO 70
<211> LENGTH: 2532
<212> TYPE: DNA
<213> ORGANISM: Artificial sequence
<220> FEATURE:
<223> OTHER INFORMATION: Double expression construct version 1 coding for shmiR17, shmiR13 and codon optimized PABPN1

<400> SEQUENCE: 70

```
cgatcgcgcg cagatctgtc atgatgatcc tagcatgctg cccatgtaag gaggcaaggc     60

ctggggacac ccgagatgcc tggttataat taacccagac atgtggctgc cccccccccc    120

ccaacacctg ctgcctctaa aaataaccct gcatgccatg ttcccggcga agggccagct    180

gtcccccgcc agctagactc agcacttagt ttaggaacca gtgagcaagt cagcccttgg    240

ggcagcccat acaaggccat ggggctgggc aagctgcacg cctgggtccg ggtgggcac    300

ggtgcccggg caacgagctg aaagctcatc tgctctcagg ggcccctccc tggggacagc    360

ccctcctggc tagtcacacc ctgtaggctc ctctatataa cccaggggca caggggctgc    420

cctcattcta ccaccacctc cacagcacag acagacactc aggagccagc cagcgtcgat    480

cattgaagtt actattccga agttcctatt ctctagaatt cgccaccacg cgtggtatat    540

tgctgttgac agtgagcgaa ggtagagaag cagatgaata ctgtgaagca gatgggtatt    600

catctgcttc tctacctccg cctactgcct cggacttcaa atcatctact ccatggccct    660

ctgcgtttgc tgaagacaga accgcaaagc aggacccgac aggattctcc ccgcctcttc    720

agagactatg tttacaagat atcggtatat tgctgttgac agtgagcgac gacatcatgg    780

tattccccta ctgtgaagca gatgggtagg ggaataccat gatgtcgccg cctactgcct    840

cggacttcaa gtcgacgcta gcaataaagg atcctttatt ttcattggat ccgtgtgttg    900

gtttttgtg tgcggttaat taaggtaccc gagctccacc gcggtggcgg ccgtccgccc    960

tcggcaccat cctcacgaca cccaaatatg gcgacgggtg aggaatggtg gggagttatt   1020

tttagagcgg tgaggaaggt gggcaggcag caggtgttgg cgctctaaaa ataactcccg   1080

ggagttattt ttagagcgga ggaatggtgg acacccaaat atggcgacgg ttcctcaccc   1140

gtcgccatat ttgggtgtcc gccctcggcc ggggccgcat tcctgggggc cgggcggtgc   1200

tcccgcccgc ctcgataaaa ggctccgggg ccggcggcgg cccacgagct acccggagga   1260

gcgggaggcg ccaagctcta gaactagtgg atcccccggg ctgcaggaat tcgatgccac   1320

catggccgct gccgccgctg ctgctgccgc agccggcgct gccggcggaa gaggcagcgg   1380

ccctggcaga cggcggcatc tggtccctgg cgccggaggg gaggccggcg aaggcgcccc   1440

tggcggagcc ggcgactacg gcaacggcct ggaaagcgag gaactggaac ccgaggaact   1500

gctgctggaa cctgagcccg agccagagcc cgaggaagag ccccctaggc caagagcccc   1560
```

```
ccctggcgcc ccaggaccag gaccaggctc tggggcacca ggctctcagg aagaggaaga   1620

agagcccggc ctcgtcgagg gagacccagg cgatggcgct atcgaagatc ccgagctgga   1680

agccatcaag gccagagtgc gggagatgga agaggaggcc gaaaaattga aagagctgca   1740

gaacgaagtc gaaaaacaaa tgaacatgtc ccccctcct ggaaatgctg gccctgtgat   1800

catgagcatc gaggaaaaga tggaagccga cgcccggtct atctacgtgg gcaacgtgga   1860

ctacggcgcc accgccgaag aactggaagc ccactttcac ggctgtggca gcgtgaaccg   1920

ggtgaccatc ctgtgcgaca agttcagcgg ccaccccaag ggcttcgcct acatcgagtt   1980

cagcgacaaa gaaagcgtgc ggacctctct ggctctcgac gagtctctgt tcaggggaag   2040

gcagatcaag gtcatcccca agcggaccaa caggcccggc atcagcacca ccgacagagg   2100

cttccctagg gctaggtaca gagcccggac caccaactac aacagcagca gaagccggtt   2160

ctacagcggc ttcaattctc ggcctagagg cagagtgtac cggggcaggg ccagggccac   2220

ctcctggtac agcccctacg aacagaagct gatcagcgag gaagatctgt gatgagatat   2280

ctgatgacat atgacgcgtt taattaactg tgccttctag ttgccagcca tctgttgttt   2340

gcccctcccc cgtgccttcc ttgaccctgg aaggtgccac tcccactgtc ctttcctaat   2400

aaaatgagga aattgcatcg cattgtctga gtaggtgtca ttctattctg gggggtgggg   2460

tggggcagga cagcaagggg gaggattggg aagacaatag caggcatgct ggggatgcgg   2520

tgggctctat gg                                                       2532


<210> SEQ ID NO 71
<211> LENGTH: 1943
<212> TYPE: DNA
<213> ORGANISM: Artificial sequence
<220> FEATURE:
<223> OTHER INFORMATION: Double expression construct version 2 coding
      for shmiR3, shmiR14 and codon optimized PABPN1

<400> SEQUENCE: 71

cgagctccac cgcggtggcg gccgtccgcc ctcggcacca tcctcacgac acccaaatat     60

ggcgacgggt gaggaatggt ggggagttat ttttagagcg gtgaggaagg tgggcaggca    120

gcaggtgttg gcgctctaaa aataactccc gggagttatt tttagagcgg aggaatggtg    180

gacacccaaa tatggcgacg gttcctcacc cgtcgccata tttgggtgtc cgccctcggc    240

cggggccgca ttcctggggg ccgggcggtg ctcccgcccg cctcgataaa aggctccggg    300

gccggcggcg gcccacgagc tacccggagg agcgggaggc gccaagctct agaactagtg    360

gatcccccgg gctgcaggaa ttcgatgcca ccatggccgc tgccgccgct gctgctgccg    420

cagccggcgc tgccggcgga agaggcagcg gccctggcag acggcggcat ctggtccctg    480

gcgccggagg ggaggccggc gaaggcgccc ctggcggagc cggcgactac ggcaacggcc    540

tggaaagcga ggaactggaa cccgaggaac tgctgctgga acctgagccc gagccagagc    600

ccgaggaaga gcccccctagg ccaagagccc cccctggcgc cccaggacca ggaccaggct    660

ctggggcacc aggctctcag gaagaggaag aagagcccgg cctcgtcgag ggagacccag    720

gcgatggcgc tatcgaagat cccgagctgg aagccatcaa ggccagagtg cgggagatgg    780

aagaggaggc cgaaaaattg aaagagctgc agaacgaagt cgaaaaacaa atgaacatgt    840

cccccctcc tggaaatgct ggccctgtga tcatgagcat cgaggaaaag atggaagccg    900

acgcccggtc tatctacgtg ggcaacgtgg actacggcgc caccgccgaa gaactggaag    960

cccactttca cggctgtggc agcgtgaacc gggtgaccat cctgtgcgac aagttcagcg   1020
```

gccaccccaa gggcttcgcc tacatcgagt tcagcgacaa agaaagcgtg cggacctctc 1080
tggctctcga cgagtctctg ttcaggggaa ggcagatcaa ggtcatcccc aagcggacca 1140
acaggcccgg catcagcacc accgacagag gcttccctag ggctaggtac agagcccgga 1200
ccaccaacta caacagcagc agaagccggt tctacagcgg cttcaattct cggcctagag 1260
gcagagtgta ccggggcagg gccagggcca cctcctggta cagcccctac tgatgacata 1320
tgacgcgtgg tatattgctg ttgacagtga gcgagaggta gagaagcaga tgaaactgtg 1380
aagcagatgg gtttcatctg cttctctacc tcgcgcctac tgcctcggac ttcaaatcat 1440
ctactccatg gccctctgcg tttgctgaag acagaaccgc aaagcaggac ccgacaggat 1500
tctccccgcc tcttcagaga ctatgtttac aagatatcgg tatattgctg ttgacagtga 1560
gcgtgagaag cagatgaata tgagactgtg aagcagatgg gtctcatatt catctgcttc 1620
tctcgcctac tgcctcggac ttcaagtcga cgctagcaat aaaggatcct ttattttcat 1680
tggatccgtg tgttggtttt ttgtgtgcgg ttaattaact gtgccttcta gttgccagcc 1740
atctgttgtt tgcccctccc ccgtgccttc cttgaccctg gaaggtgcca ctcccactgt 1800
cctttcctaa taaaatgagg aaattgcatc gcattgtctg agtaggtgtc attctattct 1860
ggggggtggg gtggggcagg acagcaaggg ggaggattgg gaagacaata gcaggcatgc 1920
tggggatgcg gtgggctcta tgg 1943

<210> SEQ ID NO 72
<211> LENGTH: 1943
<212> TYPE: DNA
<213> ORGANISM: Artificial sequence
<220> FEATURE:
<223> OTHER INFORMATION: Double expression construct version 2 coding for shmiR17, shmiR13 and codon optimized PABPN1

<400> SEQUENCE: 72
cgagctccac cgcggtggcg gccgtccgcc ctcggcacca tcctcacgac acccaaatat 60
ggcgacgggt gaggaatggt ggggagttat ttttagagcg gtgaggaagg tgggcaggca 120
gcaggtgttg gcgctctaaa aataactccc gggagttatt tttagagcgg aggaatggtg 180
gacacccaaa tatggcgacg gttcctcacc cgtcgccata tttgggtgtc cgccctcggc 240
cggggccgca ttcctggggg ccgggcggtg ctcccgcccg cctcgataaa aggctccggg 300
gccggcggcg gcccacgagc tacccggagg agcgggaggc gccaagctct agaactagtg 360
gatcccccgg gctgcaggaa ttcgatgcca ccatggccgc tgccgccgct gctgctgccg 420
cagccggcgc tgccggcgga agaggcagcg gccctggcag acggcggcat ctggtccctg 480
gcgccggagg ggaggccggc gaaggcgccc ctggcggagc cggcgactac ggcaacggcc 540
tggaaagcga ggaactggaa cccgaggaac tgctgctgga acctgagccc gagccagagc 600
ccgaggaaga gccccctagg ccaagagccc cccctggcgc cccaggacca ggaccaggct 660
ctggggcacc aggctctcag gaagaggaag aagagcccgg cctcgtcgag ggagacccag 720
gcgatggcgc tatcgaagat cccgagctgg aagccatcaa ggccagagtg cgggagatgg 780
aagaggaggc cgaaaaattg aaagagctgc agaacgaagt cgaaaaacaa atgaacatgt 840
ccccccctcc tggaaatgct ggccctgtga tcatgagcat cgaggaaaag atggaagccg 900
acgcccggtc tatctacgtg ggcaacgtgg actacggcgc caccgccgaa gaactggaag 960
cccactttca cggctgtggc agcgtgaacc gggtgaccat cctgtgcgac aagttcagcg 1020
gccaccccaa gggcttcgcc tacatcgagt tcagcgacaa agaaagcgtg cggacctctc 1080
tggctctcga cgagtctctg ttcaggggaa ggcagatcaa ggtcatcccc aagcggacca 1140
acaggcccgg catcagcacc accgacagag gcttccctag ggctaggtac agagcccgga 1200
ccaccaacta caacagcagc agaagccggt tctacagcgg cttcaattct cggcctagag 1260
gcagagtgta ccggggcagg gccagggcca cctcctggta cagcccctac tgatgacata 1320
tgacgcgtgg tatattgctg ttgacagtga gcgaaggtag agaagcagat gaatactgtg 1380
aagcagatgg gtattcatct gcttctctac ctccgcctac tgcctcggac ttcaaatcat 1440
ctactccatg gccctctgcg tttgctgaag acagaaccgc aaagcaggac ccgacaggat 1500
tctccccgcc tcttcagaga ctatgtttac aagatatcgg tatattgctg ttgacagtga 1560
gcgacgacat catggtattc ccctactgtg aagcagatgg gtaggggaat accatgatgt 1620
cgccgcctac tgcctcggac ttcaagtcga cgctagcaat aaaggatcct ttattttcat 1680
tggatccgtg tgttggtttt ttgtgtgcgg ttaattaact gtgccttcta gttgccagcc 1740
atctgttgtt tgcccctccc ccgtgccttc cttgaccctg gaaggtgcca ctcccactgt 1800
cctttcctaa taaaatgagg aaattgcatc gcattgtctg agtaggtgtc attctattct 1860
ggggggtggg gtggggcagg acagcaaggg ggaggattgg gaagacaata gcaggcatgc 1920
tggggatgcg gtgggctcta tgg 1943

<210> SEQ ID NO 73
<211> LENGTH: 921
<212> TYPE: DNA
<213> ORGANISM: Artificial sequence
<220> FEATURE:
<223> OTHER INFORMATION: Human codon-optimized PABPN1 cDNA sequence

<400> SEQUENCE: 73
atggccgctg ccgccgctgc tgctgccgca gccggcgctg ccggcggaag aggcagcggc 60
cctggcagac ggcggcatct ggtccctggc gccggagggg aggccggcga aggcgcccct 120
ggcggagccg gcgactacgg caacggcctg gaaagcgagg aactggaacc cgaggaactg 180
ctgctggaac ctgagcccga gccagagccc gaggaagagc cccctaggcc aagagccccc 240
cctggcgccc caggaccagg accaggctct ggggcaccag gctctcagga agaggaagaa 300
gagcccggcc tcgtcgaggg agacccaggc gatggcgcta tcgaagatcc cgagctggaa 360
gccatcaagg ccagagtgcg ggagatggaa gaggaggccg aaaaattgaa agagctgcag 420
aacgaagtcg aaaaacaaat gaacatgtcc ccccctcctg gaaatgctgg ccctgtgatc 480
atgagcatcg aggaaaagat ggaagccgac gcccggtcta tctacgtggg caacgtggac 540
tacggcgcca ccgccgaaga actggaagcc cactttcacg gctgtggcag cgtgaaccgg 600
gtgaccatcc tgtgcgacaa gttcagcggc caccccaagg gcttcgccta catcgagttc 660
agcgacaaag aaagcgtgcg gacctctctg gctctcgacg agtctctgtt caggggaagg 720
cagatcaagg tcatccccaa gcggaccaac aggcccggca tcagcaccac cgacagaggc 780
ttccctaggg ctaggtacag agcccggacc accaactaca acagcagcag aagccggttc 840
tacagcggct tcaattctcg gcctagaggc agagtgtacc ggggcagggc cagggccacc 900
tcctggtaca gcccctactg a 921

<210> SEQ ID NO 74
<211> LENGTH: 306
<212> TYPE: PRT
<213> ORGANISM: Artificial sequence
<220> FEATURE:
<223> OTHER INFORMATION: Human wildtype PABPN1 amino acid sequence

<400> SEQUENCE: 74

Met Ala Ala Ala Ala Ala Ala Ala Ala Ala Ala Gly Ala Ala Gly Gly
1 5 10 15

Arg Gly Ser Gly Pro Gly Arg Arg Arg His Leu Val Pro Gly Ala Gly
20 25 30

Gly Glu Ala Gly Glu Gly Ala Pro Gly Gly Ala Gly Asp Tyr Gly Asn
35 40 45

Gly Leu Glu Ser Glu Glu Leu Glu Pro Glu Glu Leu Leu Glu Pro
50 55 60

Glu Pro Glu Pro Glu Pro Glu Glu Glu Pro Pro Arg Pro Arg Ala Pro
65 70 75 80

Pro Gly Ala Pro Gly Pro Gly Pro Gly Ser Gly Ala Pro Gly Ser Gln
85 90 95

Glu Glu Glu Glu Glu Pro Gly Leu Val Glu Gly Asp Pro Gly Asp Gly
100 105 110

Ala Ile Glu Asp Pro Glu Leu Glu Ala Ile Lys Ala Arg Val Arg Glu
115 120 125

Met Glu Glu Glu Ala Glu Lys Leu Lys Glu Leu Gln Asn Glu Val Glu
130 135 140

Lys Gln Met Asn Met Ser Pro Pro Pro Gly Asn Ala Gly Pro Val Ile
145 150 155 160

Met Ser Ile Glu Glu Lys Met Glu Ala Asp Ala Arg Ser Ile Tyr Val
165 170 175

Gly Asn Val Asp Tyr Gly Ala Thr Ala Glu Glu Leu Glu Ala His Phe
180 185 190

His Gly Cys Gly Ser Val Asn Arg Val Thr Ile Leu Cys Asp Lys Phe
195 200 205

Ser Gly His Pro Lys Gly Phe Ala Tyr Ile Glu Phe Ser Asp Lys Glu
210 215 220

Ser Val Arg Thr Ser Leu Ala Leu Asp Glu Ser Leu Phe Arg Gly Arg
225 230 235 240

Gln Ile Lys Val Ile Pro Lys Arg Thr Asn Arg Pro Gly Ile Ser Thr
245 250 255

Thr Asp Arg Gly Phe Pro Arg Ala Arg Tyr Arg Ala Arg Thr Thr Asn
260 265 270

Tyr Asn Ser Ser Arg Ser Arg Phe Tyr Ser Gly Phe Asn Ser Arg Pro
275 280 285

Arg Gly Arg Val Tyr Arg Gly Arg Ala Arg Ala Thr Ser Trp Tyr Ser
290 295 300

Pro Tyr
305

<210> SEQ ID NO 75
<211> LENGTH: 314
<212> TYPE: PRT
<213> ORGANISM: Artificial sequence
<220> FEATURE:
<223> OTHER INFORMATION: Human wildtype PABPN1 amino acid sequence (with FLAG tag)

<400> SEQUENCE: 75

Met Ala Ala Ala Ala Ala Ala Ala Ala Ala Ala Gly Ala Ala Gly Gly
1 5 10 15

Arg Gly Ser Gly Pro Gly Arg Arg Arg His Leu Val Pro Gly Ala Gly
20 25 30

```
Gly Glu Ala Gly Glu Gly Ala Pro Gly Gly Ala Gly Asp Tyr Gly Asn
        35                  40                  45

Gly Leu Glu Ser Glu Glu Leu Glu Pro Glu Glu Leu Leu Leu Glu Pro
    50                  55                  60

Glu Pro Glu Pro Glu Pro Glu Glu Glu Pro Pro Arg Pro Arg Ala Pro
65                  70                  75                  80

Pro Gly Ala Pro Gly Pro Gly Pro Gly Ser Gly Ala Pro Gly Ser Gln
                85                  90                  95

Glu Glu Glu Glu Glu Pro Gly Leu Val Glu Gly Asp Pro Gly Asp Gly
            100                 105                 110

Ala Ile Glu Asp Pro Glu Leu Glu Ala Ile Lys Ala Arg Val Arg Glu
        115                 120                 125

Met Glu Glu Glu Ala Glu Lys Leu Lys Glu Leu Gln Asn Glu Val Glu
    130                 135                 140

Lys Gln Met Asn Met Ser Pro Pro Pro Gly Asn Ala Gly Pro Val Ile
145                 150                 155                 160

Met Ser Ile Glu Glu Lys Met Glu Ala Asp Ala Arg Ser Ile Tyr Val
                165                 170                 175

Gly Asn Val Asp Tyr Gly Ala Thr Ala Glu Glu Leu Glu Ala His Phe
            180                 185                 190

His Gly Cys Gly Ser Val Asn Arg Val Thr Ile Leu Cys Asp Lys Phe
        195                 200                 205

Ser Gly His Pro Lys Gly Phe Ala Tyr Ile Glu Phe Ser Asp Lys Glu
    210                 215                 220

Ser Val Arg Thr Ser Leu Ala Leu Asp Glu Ser Leu Phe Arg Gly Arg
225                 230                 235                 240

Gln Ile Lys Val Ile Pro Lys Arg Thr Asn Arg Pro Gly Ile Ser Thr
                245                 250                 255

Thr Asp Arg Gly Phe Pro Arg Ala Arg Tyr Arg Ala Arg Thr Thr Asn
            260                 265                 270

Tyr Asn Ser Ser Arg Ser Arg Phe Tyr Ser Gly Phe Asn Ser Arg Pro
        275                 280                 285

Arg Gly Arg Val Tyr Arg Gly Arg Ala Arg Ala Thr Ser Trp Tyr Ser
    290                 295                 300

Pro Tyr Asp Tyr Lys Asp Asp Asp Asp Lys
305                 310
```

<210> SEQ ID NO 76
<211> LENGTH: 314
<212> TYPE: PRT
<213> ORGANISM: Artificial sequence
<220> FEATURE:
<223> OTHER INFORMATION: Human codon-optimized PABPN1 amino acid sequence (with FLAG-tag)

<400> SEQUENCE: 76

```
Met Ala Ala Ala Ala Ala Ala Ala Ala Ala Ala Gly Ala Ala Gly Gly
1               5                   10                  15

Arg Gly Ser Gly Pro Gly Arg Arg Arg His Leu Val Pro Gly Ala Gly
            20                  25                  30

Gly Glu Ala Gly Glu Gly Ala Pro Gly Gly Ala Gly Asp Tyr Gly Asn
        35                  40                  45

Gly Leu Glu Ser Glu Glu Leu Glu Pro Glu Glu Leu Leu Leu Glu Pro
    50                  55                  60

Glu Pro Glu Pro Glu Pro Glu Glu Glu Pro Pro Arg Pro Arg Ala Pro
```

```
65                  70                  75                  80

Pro Gly Ala Pro Gly Pro Gly Pro Gly Ser Gly Ala Pro Gly Ser Gln
                85                  90                  95

Glu Glu Glu Glu Glu Pro Gly Leu Val Glu Gly Asp Pro Gly Asp Gly
            100                 105                 110

Ala Ile Glu Asp Pro Glu Leu Glu Ala Ile Lys Ala Arg Val Arg Glu
        115                 120                 125

Met Glu Glu Glu Ala Glu Lys Leu Lys Glu Leu Gln Asn Glu Val Glu
    130                 135                 140

Lys Gln Met Asn Met Ser Pro Pro Pro Gly Asn Ala Gly Pro Val Ile
145                 150                 155                 160

Met Ser Ile Glu Glu Lys Met Glu Ala Asp Ala Arg Ser Ile Tyr Val
                165                 170                 175

Gly Asn Val Asp Tyr Gly Ala Thr Ala Glu Glu Leu Glu Ala His Phe
            180                 185                 190

His Gly Cys Gly Ser Val Asn Arg Val Thr Ile Leu Cys Asp Lys Phe
        195                 200                 205

Ser Gly His Pro Lys Gly Phe Ala Tyr Ile Glu Phe Ser Asp Lys Glu
    210                 215                 220

Ser Val Arg Thr Ser Leu Ala Leu Asp Glu Ser Leu Phe Arg Gly Arg
225                 230                 235                 240

Gln Ile Lys Val Ile Pro Lys Arg Thr Asn Arg Pro Gly Ile Ser Thr
                245                 250                 255

Thr Asp Arg Gly Phe Pro Arg Ala Arg Tyr Arg Ala Arg Thr Thr Asn
            260                 265                 270

Tyr Asn Ser Ser Arg Ser Arg Phe Tyr Ser Gly Phe Asn Ser Arg Pro
        275                 280                 285

Arg Gly Arg Val Tyr Arg Gly Arg Ala Arg Ala Thr Ser Trp Tyr Ser
    290                 295                 300

Pro Tyr Asp Tyr Lys Asp Asp Asp Asp Lys
305                 310
```

<210> SEQ ID NO 77
<211> LENGTH: 20
<212> TYPE: DNA
<213> ORGANISM: Artificial sequence
<220> FEATURE:
<223> OTHER INFORMATION: wtPABPN1-Fwd primer

<400> SEQUENCE: 77
atggtgcaac agcagaagag 20

<210> SEQ ID NO 78
<211> LENGTH: 20
<212> TYPE: DNA
<213> ORGANISM: Artificial sequence
<220> FEATURE:
<223> OTHER INFORMATION: wtPABPN1-Rev primer

<400> SEQUENCE: 78
ctttgggatg gccactaaat 20

<210> SEQ ID NO 79
<211> LENGTH: 23
<212> TYPE: DNA
<213> ORGANISM: Artificial sequence
<220> FEATURE:
<223> OTHER INFORMATION: wtPABPN1-Probe

<400> SEQUENCE: 79
cggttgactg aaccacagcc atg 23

<210> SEQ ID NO 80
<211> LENGTH: 19
<212> TYPE: DNA
<213> ORGANISM: Artificial sequence
<220> FEATURE:
<223> OTHER INFORMATION: optPABPN1-For primer

<400> SEQUENCE: 80
accgacagag gcttcccta 19

<210> SEQ ID NO 81
<211> LENGTH: 21
<212> TYPE: DNA
<213> ORGANISM: Artificial sequence
<220> FEATURE:
<223> OTHER INFORMATION: optPABPN1-Rev primer

<400> SEQUENCE: 81
ttctgctgct gttgtagttg g 21

<210> SEQ ID NO 82
<211> LENGTH: 23
<212> TYPE: DNA
<213> ORGANISM: Artificial sequence
<220> FEATURE:
<223> OTHER INFORMATION: optPABPN1-Probe

<400> SEQUENCE: 82
tggtccgggc tctgtaccta gcc 23

<210> SEQ ID NO 83
<211> LENGTH: 21
<212> TYPE: DNA
<213> ORGANISM: Artificial sequence
<220> FEATURE:
<223> OTHER INFORMATION: shmiR3-Fwd primer

<400> SEQUENCE: 83
ttcatctgct tctctacctc g 21

<210> SEQ ID NO 84
<211> LENGTH: 21
<212> TYPE: DNA
<213> ORGANISM: Artificial sequence
<220> FEATURE:
<223> OTHER INFORMATION: shmiR13-Fwd primer

<400> SEQUENCE: 84
aggggaatac catgatgtcg c 21

<210> SEQ ID NO 85
<211> LENGTH: 21
<212> TYPE: DNA
<213> ORGANISM: Artificial sequence
<220> FEATURE:
<223> OTHER INFORMATION: shmiR14-Fwd primer

<400> SEQUENCE: 85
ctcatattca tctgcttctc t 21

<210> SEQ ID NO 86
<211> LENGTH: 21

<212> TYPE: DNA
<213> ORGANISM: Artificial sequence
<220> FEATURE:
<223> OTHER INFORMATION: shmiR17-Fwd primer

<400> SEQUENCE: 86
attcatctgc ttctctacct c 21

<210> SEQ ID NO 87
<211> LENGTH: 64
<212> TYPE: PRT
<213> ORGANISM: Adenoassociated virus serotype 9

<400> SEQUENCE: 87

Ala Arg Gly Leu Val Leu Pro Gly Tyr Lys Tyr Leu Gly Pro Gly Asn
1 5 10 15

Gly Leu Asp Lys Gly Glu Pro Val Asn Ala Ala Asp Ala Ala Ala Leu
20 25 30

Glu His Asp Lys Ala Tyr Asp Gln Gln Leu Lys Ala Gly Asp Asn Pro
35 40 45

Tyr Leu Lys Tyr Asn His Ala Asp Ala Glu Phe Gln Glu Arg Leu Lys
50 55 60

<210> SEQ ID NO 88
<211> LENGTH: 64
<212> TYPE: PRT
<213> ORGANISM: Artificial Sequence
<220> FEATURE:
<223> OTHER INFORMATION: Modified VP1 PL subsequence for AAV9

<400> SEQUENCE: 88

Ser Arg Gly Leu Val Leu Pro Gly Tyr Lys Tyr Leu Gly Pro Gly Asn
1 5 10 15

Gly Leu Asp Lys Gly Glu Pro Val Asn Glu Ala Asp Ala Ala Ala Leu
20 25 30

Glu His Asp Lys Ala Tyr Asp Arg Gln Leu Asp Ser Gly Asp Asn Pro
35 40 45

Tyr Leu Lys Tyr Asn His Ala Asp Ala Glu Phe Gln Glu Arg Leu Lys
50 55 60

<210> SEQ ID NO 89
<211> LENGTH: 736
<212> TYPE: PRT
<213> ORGANISM: Adenoassociated virus serotype 9

<400> SEQUENCE: 89

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Gln Pro
20 25 30

Lys Ala Asn Gln Gln His Gln Asp Asn Ala Arg Gly Leu Val Leu Pro
35 40 45

Gly Tyr Lys Tyr Leu Gly Pro Gly Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Lys Tyr Asn His Ala
85 90 95

Asp Ala Glu Phe Gln Glu Arg Leu Lys Glu Asp Thr Ser Phe Gly Gly
100 105 110

```
Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525
```

```
Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 90
<211> LENGTH: 736
<212> TYPE: PRT
<213> ORGANISM: Artificial Sequence
<220> FEATURE:
<223> OTHER INFORMATION: Modified AAV9 capsid VP1 (full length)

<400> SEQUENCE: 90

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ser Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160
```

-continued

```
Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
```

```
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 91
<211> LENGTH: 64
<212> TYPE: PRT
<213> ORGANISM: Adenoassociated virus serotype 8

<400> SEQUENCE: 91

Gly Arg Gly Leu Val Leu Pro Gly Tyr Lys Tyr Leu Gly Pro Phe Asn
1               5                   10                  15

Gly Leu Asp Lys Gly Glu Pro Val Asn Ala Ala Asp Ala Ala Ala Leu
            20                  25                  30

Glu His Asp Lys Ala Tyr Asp Gln Gln Leu Lys Ala Gly Asp Asn Pro
        35                  40                  45

Tyr Leu Arg Tyr Asn His Ala Asp Ala Glu Phe Gln Glu Arg Leu Gln
    50                  55                  60


<210> SEQ ID NO 92
<211> LENGTH: 64
<212> TYPE: PRT
<213> ORGANISM: Artificial Sequence
<220> FEATURE:
<223> OTHER INFORMATION: Modified VP1 PL subsequence for AAV8

<400> SEQUENCE: 92

Ser Arg Gly Leu Val Leu Pro Gly Tyr Lys Tyr Leu Gly Pro Phe Asn
1               5                   10                  15

Gly Leu Asp Lys Gly Glu Pro Val Asn Glu Ala Asp Ala Ala Ala Leu
            20                  25                  30

Glu His Asp Lys Ala Tyr Asp Arg Gln Leu Asp Ser Gly Asp Asn Pro
        35                  40                  45

Tyr Leu Arg Tyr Asn His Ala Asp Ala Glu Phe Gln Glu Arg Leu Lys
    50                  55                  60


<210> SEQ ID NO 93
<211> LENGTH: 738
<212> TYPE: PRT
<213> ORGANISM: Adenoassociated virus serotype 8

<400> SEQUENCE: 93
```

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
```

```
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu


<210> SEQ ID NO 94
<211> LENGTH: 738
<212> TYPE: PRT
<213> ORGANISM: Artificial Sequence
<220> FEATURE:
<223> OTHER INFORMATION: Modified AAV8 capsid VP1 (full length)

<400> SEQUENCE: 94

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Ser Arg Gly Leu Val Leu Pro
        35                  40                  45
```

```
Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Arg Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460
```

```
Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu
```

<210> SEQ ID NO 95
<211> LENGTH: 145
<212> TYPE: DNA
<213> ORGANISM: adeno-associated virus 2

<400> SEQUENCE: 95

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcct                                          145
```

<210> SEQ ID NO 96
<211> LENGTH: 145
<212> TYPE: DNA
<213> ORGANISM: adeno-associated virus 2

<400> SEQUENCE: 96

```
aggaacccct agtgatggag ttggccactc cctctctgcg cgctcgctcg ctcactgagg     60

ccgggcgacc aaaggtcgcc cgacgcccgg gctttgcccg ggcggcctca gtgagcgagc    120
```

gagcgcgcag agagggagtg gccaa 145

<210> SEQ ID NO 97
<211> LENGTH: 735
<212> TYPE: PRT
<213> ORGANISM: adeno-associated virus 2

<400> SEQUENCE: 97

Met Ala Ala Asp Gly Tyr Leu Pro Asp Trp Leu Glu Asp Thr Leu Ser
1 5 10 15

Glu Gly Ile Arg Gln Trp Trp Lys Leu Lys Pro Gly Pro Pro Pro Pro
20 25 30

Lys Pro Ala Glu Arg His Lys Asp Asp Ser Arg Gly Leu Val Leu Pro
35 40 45

Gly Tyr Lys Tyr Leu Gly Pro Phe Asn Gly Leu Asp Lys Gly Glu Pro
50 55 60

Val Asn Glu Ala Asp Ala Ala Ala Leu Glu His Asp Lys Ala Tyr Asp
65 70 75 80

Arg Gln Leu Asp Ser Gly Asp Asn Pro Tyr Leu Lys Tyr Asn His Ala
85 90 95

Asp Ala Glu Phe Gln Glu Arg Leu Lys Glu Asp Thr Ser Phe Gly Gly
100 105 110

Asn Leu Gly Arg Ala Val Phe Gln Ala Lys Lys Arg Val Leu Glu Pro
115 120 125

Leu Gly Leu Val Glu Glu Pro Val Lys Thr Ala Pro Gly Lys Lys Arg
130 135 140

Pro Val Glu His Ser Pro Val Glu Pro Asp Ser Ser Ser Gly Thr Gly
145 150 155 160

Lys Ala Gly Gln Gln Pro Ala Arg Lys Arg Leu Asn Phe Gly Gln Thr
165 170 175

Gly Asp Ala Asp Ser Val Pro Asp Pro Gln Pro Leu Gly Gln Pro Pro
180 185 190

Ala Ala Pro Ser Gly Leu Gly Thr Asn Thr Met Ala Thr Gly Ser Gly
195 200 205

Ala Pro Met Ala Asp Asn Asn Glu Gly Ala Asp Gly Val Gly Asn Ser
210 215 220

Ser Gly Asn Trp His Cys Asp Ser Thr Trp Met Gly Asp Arg Val Ile
225 230 235 240

Thr Thr Ser Thr Arg Thr Trp Ala Leu Pro Thr Tyr Asn Asn His Leu
245 250 255

Tyr Lys Gln Ile Ser Ser Gln Ser Gly Ala Ser Asn Asp Asn His Tyr
260 265 270

Phe Gly Tyr Ser Thr Pro Trp Gly Tyr Phe Asp Phe Asn Arg Phe His
275 280 285

Cys His Phe Ser Pro Arg Asp Trp Gln Arg Leu Ile Asn Asn Asn Trp
290 295 300

Gly Phe Arg Pro Lys Arg Leu Asn Phe Lys Leu Phe Asn Ile Gln Val
305 310 315 320

Lys Glu Val Thr Gln Asn Asp Gly Thr Thr Thr Ile Ala Asn Asn Leu
325 330 335

Thr Ser Thr Val Gln Val Phe Thr Asp Ser Glu Tyr Gln Leu Pro Tyr
340 345 350

Val Leu Gly Ser Ala His Gln Gly Cys Leu Pro Pro Phe Pro Ala Asp
355 360 365

```
Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735
```

<210> SEQ ID NO 98
<211> LENGTH: 921
<212> TYPE: RNA
<213> ORGANISM: homo sapien

<400> SEQUENCE: 98

```
auggcggcgg cggcggcggc ggcagcagca gcgggggcug cgggcggucg gggcuccggg     60
```

-continued

```
ccggggcggc ggcgccaucu ugugcccggg gccggugggg aggccgggga gggggccccg    120
gggggcgcag gggacuacgg gaacggccug gagucugagg aacuggagcc ugaggagcug    180
cugcuggagc ccgagccgga gcccgagccc gaagaggagc cgccccggcc ccgcgccccc    240
ccgggagcuc cgggcccugg gccugguucg ggagcccccg gcagccaaga ggaggaggag    300
gagccgggac uggucgaggg ugacccgggg gacggcgcca uugaggaccc ggagcuggaa    360
gcuaucaaag cucgagucag ggagauggag gaagaagcug agaagcuaaa ggagcuacag    420
aacgagguag agaagcagau gaauaugagu ccaccuccag gcaaugcugg cccggugauc    480
auguccauug aggagaagau ggaggcugau gcccguucca ucuauguugg caauguggac    540
uauggugcaa cagcagaaga gcuggaagcu cacuuucaug gcugugguuc agucaaccgu    600
guuaccauac ugugugacaa auuuaguggc caucccaaag gguuugcgua uauagaguuc    660
ucagacaaag agucagugag gacuuccuug gccuuagaug agucccuauu uagaggaagg    720
caaaucaagg ugaucccaaa acgaaccaac agaccaggca ucagcacaac agaccggggu    780
uuuccacgag cccgcuaccg cgcccggacc accaacuaca acagcucccg cucucgauuc    840
uacagugguu uuaacagcag gccccggggu cgcgucuaca ggggccgggc uagagcgaca    900
ucaugguauu ccccuuacua a                                              921
```